US008835111B2

(12) United States Patent
Arteta et al.

(10) Patent No.: US 8,835,111 B2
(45) Date of Patent: Sep. 16, 2014

(54) GENOTYPING TOOL FOR IMPROVING THE PROGNOSTIC AND CLINICAL MANAGEMENT OF MS PATIENTS

(75) Inventors: David Arteta, Derio (ES); Marta Artieda, Derio (ES); Diego Tejedor, Derio (ES); Antonio Martinez, Derio (ES); Laureano Simon, Derio (ES); Bart A. Crusius, Amsterdam (NL); Salvador Pena, Amsterdam (NL); Madeleine Sombekke, Amsterdam (NL); Bernard Uitdehaag, Amsterdam (NL); Chris Polman, Amsterdam (NL)

(73) Assignee: Brainco Biopharma S.L., Derio (ES)

( * ) Notice: Subject to any disclaimer, the term of this patent is extended or adjusted under 35 U.S.C. 154(b) by 10 days.

(21) Appl. No.: 13/255,871

(22) PCT Filed: Mar. 12, 2010

(86) PCT No.: PCT/GB2010/000466
§ 371 (c)(1),
(2), (4) Date: Nov. 23, 2011

(87) PCT Pub. No.: WO2010/103292
PCT Pub. Date: Sep. 16, 2010

(65) Prior Publication Data
US 2012/0065096 A1 Mar. 15, 2012

Related U.S. Application Data

(60) Provisional application No. 61/210,124, filed on Mar. 12, 2009.

(51) Int. Cl.
C12Q 1/68 (2006.01)
C12P 19/34 (2006.01)
A61K 39/395 (2006.01)

(52) U.S. Cl.
CPC ........ *C12Q 1/6883* (2013.01); *C12Q 2600/156* (2013.01); *C12Q 2600/172* (2013.01); *C12Q 2600/106* (2013.01)
USPC ......................... 435/6.1; 435/91.2; 424/146.1

(58) Field of Classification Search
None
See application file for complete search history.

(56) References Cited

U.S. PATENT DOCUMENTS

2004/0091915 A1 5/2004 Comings et al.
2006/0240463 A1 10/2006 Lancet et al.

FOREIGN PATENT DOCUMENTS

WO WO 03/095618 11/2003
WO WO 2005/054810 6/2005
WO WO 2008/010082 1/2008

OTHER PUBLICATIONS

Li K.-C. et al. Genome Biology 2007, 8:pp. R205, pp. 1-9.*
Pennisi E. Science; Sep. 18, 1998; 281, 5384, pp. 1787-1789.*
Wall J.D. et al. Nature Reviews—Genetics, vol. 4, Aug. 2003, pp. 587-597.*
Pal P. et al. The Prostate 69:1548-1556 (2009).*
Hegele R.A. Arterioscler Thromb Vasc Biol. 2002;22:1058-1061.*
dbSNP Submitted SNP(ss) Details: ss44018686, Jul. 18, 2005, from www.ncbi.nlm.nih.gov, pp. 1-4.*
dbSNP Submitted SNP(ss) Details: ss44004073, Jul. 18, 2005, from www.ncbi.nlm.nih.gov, pp. 1-2.*
dbSNP Submitted SNP(ss) Details: ss44029596, Jul. 18, 2005, from www.ncbi.nlm.nih.gov, pp. 1-7.*
Barcellos et al., "Linkage and Association with the *NOS2A* Locus on Chromosome 17q11 in Multiple Sclerosis," *Ann. Neurol.*, vol. 55, pp. 793-800, 2004.
Bennetts et al., "HLA-DMB Gene and HLA-DRA Promoter Region Polymorphisms in Australian Multiple Sclerosis Patients," *Human Immunology*, vol. 60, pp. 886-893, 1999.
Bugeja et al., "An investigation of NOS2A promoter polymorphisms in Australian multiple sclerosis patients," *European Journal of Human Genetics*, vol. 13, pp. 815-822, 2005.
Deluca et al., "An extremes of outcome strategy provides evidence that multiple sclerosis severity is determined by alleles at the *HLA-DRB1* locus," *Proc. Natl. Acad. Sci. USA*, vol. 104, No. 52, pp. 20896-20901, 2007.
Djuric et al., "Association of the MMP-3 5A/6A gene polymorphism with multiple sclerosis in patients from Serbia," *Journal of the Neurological Sciences*, vol. 267, pp. 62-65, 2008.
EBI Accession No. GSN:ANN35634, "CCL5 gene detecting probe 1, SEQ ID 83," 2007.
EBI Accession No. GSN:ANN35365, "CCL5 gene detecting probe 2, SEQ ID 2007 84," 2007.
Godde et al., "Association of the HLA region with multiple sclerosis as confirmed by a genome screen using >10,000 SNPs on DNA chips," *J. Mol. Med.*, vol. 83, pp. 486-494, 2005.

(Continued)

*Primary Examiner* — Stephen Kapushoc
(74) *Attorney, Agent, or Firm* — Klarquist Sparkman, LLP

(57) ABSTRACT

The invention relates to methods of evaluating MS severity based on analysis of single nucleotide polymorphisms (SNPs) and to products and kits for use in such methods. The methods include a method of assessing a multiple sclerosis disease severity phenotype in a human subject having multiple sclerosis, by determining the genotype of the subject at one or more positions of single nucleotide polymorphism (SNP) selected from: rs2107538, rs1137933, rs1318, rs2069763, rs423904, rs876493, rs10243024, rs10259085, rs1042173, rs10492503, rs10492972, rs12047808, rs12202350, rs12861247, rs13353224, rs1350666, rs1555322, rs1611115, rs17641078, rs1805009, rs2028455, rs2032893, rs2049306, rs2066713, rs2074897, rs2076530, rs2187668, rs2213584, rs2227139, rs2234978, rs2239802, rs2395182, rs260461, rs28386840, rs3087456, rs3135388, rs3741981, rs3756450, rs3781202, rs3787283, rs3808585, rs4128767, rs4404254, rs4473631, rs4680534, rs6077690, rs6457594, rs6570426, rs659366, rs6917747, rs7208257, rs7528684, rs7577925, rs762550, rs7956189, rs7995215, rs8049651, rs8702, rs9808753 and rs987107, and/or a SNP in linkage disequilibrium with any one of said SNPs.

10 Claims, 7 Drawing Sheets

(56) References Cited

OTHER PUBLICATIONS

Grossman et al., "Pharmacogenetics of glatiramer acetate therapy for multiple sclerosis reveals drug-response markers," *Pharmacogenetics and Genomics*, vol. 17, pp. 657-666, 2007.

Hoppenbrouwers et al., "Replication of CD58 and CLEC16A as genome-wide significant risk genes for multiple sclerosis," *Journal of Human Genetics*, vol. 54, pp. 676-680, 2009.

International Multiple Sclerosis Genetics Consortium, "Risk Alleles for Multiple Sclerosis Identified by a Genomewide Study," *The New England Journal of Medicine*, vol. 357, No. 9, pp. 851-862, 2007.

Manna et al., "Preliminary evidences of a NOS2A protective effect from Relapsing—Remitting Multiple Sclerosis," *Journal of the Neurological Sciences*, vol. 264, pp. 112-117, 2008.

Motsinger et al., "Complex gene—gene interactions in multiple sclerosis: a multifactorial approach reveals associations with inflammatory genes," *Neurogenetics*, vol. 8, pp. 11-20, 2007.

Otaegui et al., "UCP2 and mitochondrial haplogroups as a multiple sclerosis risk factor," *Multiple Sclerosis* 13:454-458, 2007.

Schreiber et al., "Disease severity in Danish multiple sclerosis patients evaluated by MRI and three genetic markers (HLA-DRB1*1501, CCR5 deletion mutation, apolipoprotein E)," *Multiple Sclerosis*, vol. 8, pp. 295-298, 2002.

Sombekke et al.,"*HLA-DRB1*1501* and Spinal Cord Magnetic Resonance Imaging Lesions in Multiple Sclerosis," *Arch. Neurol.*, vol. 66, No. 12, pp. 1531-1536, 2009.

Swanberg et al.,"*MHC2TA* is associated with differential MHC molecule expression and susceptibility to rheumatoid arthritis, multiple sclerosis and myocardial infarction," *Nature Genetics*, vol. 37, No. 5, pp. 486-494, 2005.

Van Veen et al., "CCL5 and CCR5 genotypes modify clinical, radiological and pathological features of multiple sclerosis," *Journal of Neuroimmunology*, vol. 190, pp. 157-164, 2007.

Vogler et al., "Association of a common polymorphism in the promoter of UCP2 with susceptibility to multiple sclerosis," *J. Mol. Med.* 83:806-811, 2005.

Yu et al., "Association of UCP2-866 G/A polymorphism with chronic inflammatory diseases," *Genes and Immunity*, Advance online publication doi:10.1038/gene.2009.29, 2009 (5 pages).

Zhernakova et al., "Genetic variants of RANTES are associated with serum RANTES level and protection for type 1 diabetes," *Genes and Immunity*, vol. 7, pp. 544-549, 2006.

Zivadinov et al., "HLA-DRB1*1501,-DQB1*0301,-0302,-DQB1*0602, and-DQB1*0603 Alleles are associated with more severe disease outcome on MRI in patients with multiple sclerosis," *International Review of Neurobiology*, vol. 79, pp. 521-535, 2007.

Zivkovic et al., "The tag SNP for HLA-DRB1*1501, rs3135388, is significantly associated with multiple sclerosis susceptibility: Cost-effective high-throughput detection by real-time PCR," *Clinica Chimica Acta*, vol. 406, pp. 27-30, 2009.

Aulchenko et al., "Genetic Variation in the *KIF1B* Locus Influences Susceptibility to Multiple Sclerosis," *Nat. Genet.*, vol. 40, pp. 1402-1403, 2008.

Bakker et al., "A High Resolution HLA and SNP Haplotype Map for Disease Association Studies in the Extended Human MHC," *Nat. Genet.*, vol. 38, pp. 1166-1172, 2006.

Baranzini et al., "Genome-wide association analysis of susceptibility and clinical phenotype in multiple sclerosis," *Human Molecular Genetics*, vol. 18, pp. 767-778, 2008.

Cénit et al., "Glypican 5 is an interferon-beta response gene: a replication study," *Multiple Sclerosis*, vol. 15, pp. 913-917, 2009.

Cree et al., "A major histocompatibility class I locus contributes to multiple sclerosis susceptibility independently from HLA-DRB1*15:01," *PloS One* vol. 25, e11296, 2010 (10 pages).

Cunningham et al., "Pharmacogenomics of responsiveness to interferon IFN-β treatment in multiple sclerosis: a genetic screen of 100 type 1 interferon-inducible genes," *Clin. Pharmacol. Ther.*, vol. 78, pp. 635-646, 2005.

Dema et al., "Autoimmune disease association signals in *CIITA* and *KIAA0350* are not involved in celiac disease susceptibility," *Tissue Antigens*, vol. 73, pp. 326-329, 2009.

Fedetz et al., "Multiple sclerosis association study with the TENR-IL2-IL21 region in a Spanish population," *Tissue Antigens*, vol. 74, pp. 244-247, 2009.

International Multiple Sclerosis Genetics Consortium., "IL12A, MPHOSPH9/CDK2AP1 and RGS1 are novel multiple sclerosis susceptibility loci," *Genes Immun.*, vol. 11, pp. 397-405, 2010.

Matesanz et al., "The high producer variant of the Fc-receptor like-3 (*FCRL3*) gene is involved in protection against multiple sclerosis," *J. Neuroimmunol.*, vol. 195, pp. 146-150, 2008.

Matiello et al., "HLA-DRB1*1501 tagging rs3135388 polymorphism is not associated with neuromyelitis optica," *Multiple Sclerosis*, vol. 16, pp. 981-994, 2010.

Orozco et al., "Analysis of a Functional *BTNL2* Polymorphism in Type 1 Diabetes, Rheumatoid Arthritis, and Systemic Lupus Erythematosus," *Human Immunol.*, vol. 66, pp. 1235-1241, 2005.

Stokkers et al., "Five genetic markers in the interleukin 1 family in relation to inflammatory bowel disease," *Gut*, vol. 43, pp. 33-39, 1998.

Strange et al., "The multiple sclerosis severity score: associations with MC1R single nucleotide polymorphisms and host response to ultraviolet radiation," *Multiple Sclerosis*, vol. 16, pp. 1109-1116, 2010.

Szolnoki et al., "A cytoskeleton motor protein genetic variant may exert a protective effect on the occurrence of multiple sclerosis: the Janus face of the kinesin light-chain 1 56836CC genetic variant," *Neuromol. Med.*, vol. 9, pp. 335-339, 2007.

Wellcome Trust Case Control Consortium., "Genome-wide association study of 14,000 cases of seven common diseases and 3,000 shared controls," *Nature*, vol. 447, pp. 661-678, 2007.

Zhang et al., "Two genes encoding immune-regulatory molecules (*LAG3* and *IL7R*) confer susceptibility to multiple sclerosis," *Genes Immun.*, vol. 6, pp. 145-152, 2005.

\* cited by examiner

US 8,835,111 B2

GENOTYPING TOOL FOR IMPROVING THE PROGNOSTIC AND CLINICAL MANAGEMENT OF MS PATIENTS

CROSS REFERENCE TO RELATED APPLICATIONS

This is the U.S. National Stage of International Application No. PCT/GB2010/000466, filed Mar. 12, 2010, which was published in English under PCT Article 21(2), which in turn claims the benefit of U.S. Provisional Application No. 61/210,124, filed Mar. 12, 2009, which is incorporated herein in its entirety.

FIELD OF THE INVENTION

The invention relates to methods and products, in particular microarrays, for in vitro genotyping of multiple sclerosis (MS) associated genetic variations and to methods for assessment of MS disease severity.

BACKGROUND OF THE INVENTION

Multiple Sclerosis is an autoimmune chronic inflammatory disease, characterized by a progressive demyelination of the central nervous system. While its origin still remains unknown, its multifactorial etiology is well known, consisting of a clear genetic component regulated by several environmental factors.

Clinical evolution of MS is very heterogeneous, and there are different phenotypes present. These range from a very severe form where patients worsen rapidly (known as primary progressive MS), to a more benign form, where the patient practically recovers completely after each disease relapse (known as relapsing remitting MS). Nowadays, disease diagnostics is clinically based, relying on three main points: clinical history, neurologic exploration and use of several techniques (Magnetic Resonance Imaging, analysis of cerebrospinal fluid and evoked potentials).

Currently there is no treatment that will cure MS. MS therapies aim at controlling symptoms and maintaining patient's quality of life. With such treatments, the number of relapses is controlled to a certain level, allowing partial prevention of consequences that may cause such relapses. The primary aims of therapy are returning function after an attack, preventing new attacks, and preventing disability. As with any medical treatment, medications used in the management of MS have several adverse effects. Disease-modifying treatments reduce the progression rate of the disease, but do not stop it. As multiple sclerosis progresses, the symptomatology tends to increase. The disease is associated with a variety of symptoms and functional deficits that result in a range of progressive impairments and disability.

Management of these deficits is therefore very important. Both drug therapy and neurorehabilitation have shown to ease the burden of some symptoms, though neither influences disease progression. As for any patient with neurologic deficits, a multidisciplinary approach is key to limiting and overcoming disability; however, there are particular difficulties in specifying a 'core team' because people with MS may need help from almost any health profession or service at some point. Similarly, for each symptom there are different treatment options. Treatments should therefore be individualized depending both on the patient and the physician.

SUMMARY OF THE INVENTION

Aspects of the invention relate to methods of analyzing a patient's genotype, for example through analysis of SNPs, optionally combined with clinical-environmental data, for prognosis and treatment management of MS patients, leading to personalized medicine. Accordingly, in a first aspect the present invention provides a method of assessing a MS disease severity phenotype in a human subject having or suspected of having MS, the method comprising determining the genotype of the subject at one or more positions of single nucleotide polymorphism (SNP) selected from those listed in Table 10 and/or a SNP in linkage disequilibrium with any one of said SNPs. The SNPs may be as disclosed in the NCBI dbSNP build 131, *Homo sapiens* genome build 37.1 and/or NCBI dbSNP build 129, *Homo sapiens* build 36.3. The presence of one or more "risk alleles" as identified in Table 10 at one or more of the SNPs indicates that the subject has a higher probability of having a greater severity of MS. In some cases, the method of this and other aspects of the invention comprises determining that the subject does have at least one risk allele at at least one of said SNPs. In other cases, the subject may be determined to be free from said risk alleles at at least one of said SNPs. In some cases, the method of this and other aspects of the invention, the presence of:

the TT genotype at rs2107538;
the GG genotype at rs1137933;
the AA genotype at rs1318;
the GG genotype at rs2069763;
the CC genotype at rs423904;
the AA genotype at rs876493;
the GG genotype at rs10243024;
the GG genotype at rs10259085;
the AA genotype at rs1042173;
the TT genotype at rs10492503;
the GG genotype at rs10492972;
the GG genotype at rs12047808;
the AA genotype at rs12202350;
the GG genotype at rs12861247;
the AA genotype at rs13353224;
the GG genotype at rs1350666;
the AA genotype at rs1555322;
the AA genotype at rs1611115;
the GG genotype at rs17641078;
the GG genotype at rs1805009;
the GG genotype at rs2028455;
the AA genotype at rs2032893;
the AA genotype at rs2049306;
the AA genotype at rs2066713;
the AA genotype at rs2074897;
the GG genotype at rs2076530;
the AA genotype at rs2187668;
the AA genotype at rs2213584;
the CC genotype at rs2227139;
the TT genotype at rs2234978;
the GG genotype at rs2239802;
the GG genotype at rs2395182;
the AA genotype at rs260461;
the AA genotype at rs28386840;
the GG genotype at rs3087456;
the AA genotype at rs3135388;
the AA genotype at rs3741981;
the AA genotype at rs3756450;
the CT genotype at rs3781202;
the AA genotype at rs3787283;
the AA genotype at rs3808585;
the GG genotype at rs4128767;
the GG genotype at rs4404254;
the CC genotype at rs4473631;
the AA genotype at rs4680534;
the TT genotype at rs6077690;

the AA genotype at rs6457594;
the TT genotype at rs6570426;
the CC genotype at rs659366;
the GG genotype at rs6917747;
the AA genotype at rs7208257;
the GG genotype at rs7528684;
the AA genotype at rs7577925;
the AA genotype at rs762550;
the GG genotype at rs7956189;
the GG genotype at rs7995215;
the AA genotype at rs8049651;
the GG genotype at rs8702;
the GG genotype at rs9808753; and/or
the AA genotype at rs987107 is indicative of the subject having, or having a high probability of having, a more severe multiple sclerosis disease phenotype.

In some cases, a more severe multiple sclerosis disease phenotype may be a phenotype selected from: a multiple sclerosis severity score (MSSS) of 2.5 or greater; an increase in size and/or distribution of T2 brain lesions; an increased number of focal lesions in the spinal cord; an increased T2 lesion load in the brain; and the presence of diffuse abnormalities in the spinal cord. Optionally, the method of this and other aspects of the invention may comprise determining the genotype of the subject at 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more of said SNPs. Optionally, the method of the invention further comprises the measurement of at least one clinical variable, such as a clinical variable is selected from: age of the subject at onset of multiple sclerosis, gender of the subject and type of multiple sclerosis at onset of multiple sclerosis. The method of the invention may, in some cases, comprise determining the genotype of the subject at a specific combination or sub-set of SNPs selected from those listed in Table 10, such as the first 2, first 3, first 4, first 5 or first 6. Accordingly, in some cases, the method of the invention comprises determining the genotype of the subject at: at least rs2107538, rs1137933 and rs1318; at least rs2107538, rs1137933, rs1318, rs2069763, rs423904 and rs876493. In some cases, the method of the invention comprises determining the genotype of the subject at substantially all of the SNPs listed in Table 10. In some cases, the method of the invention comprises determining the genotype of the subject at only the SNPs listed in Table 10 and/or only SNPs in linkage disequilibrium with one or more of the SNPs listed in Table 10.

In certain cases, the method of the invention comprises determining the genotype of the subject at a sub-set of SNPs of those listed in Table 10, which sub-set is indicative of a particular MS disease severity phenotype. Methods for assessing particular MS disease severity phenotypes, such as a multiple sclerosis severity score (MSSS) of 2.5 or greater; an increase in size and/or distribution of T2 brain lesions; an increased number of focal lesions in the spinal cord; an increased T2 lesion load in the brain; and the presence of diffuse abnormalities in the spinal cord, may be combined to yield assessment of multiple specific MS disease severity phenotypes or performed independently.

In particular, the method of the invention may be for assessing multiple sclerosis severity score (MSSS), such as whether or not the subject has an MSSS score of 2.5 or greater, wherein the method comprises determining the genotype of the subject at at least 2 of the following positions of SNP: rs423904, rs876493, rs1137933, rs1318, rs2069763, rs2107538, rs3756450, rs12047808, rs10259085, rs1042173, rs6077690, rs1611115, rs4473631, rs2032893, rs2066713, rs260461, rs3787283, rs6917747, rs2049306, rs12861247, rs4404254, rs4680534, rs17641078, rs2187668, rs7528684, rs7577925, rs1805009, rs3741981, rs12202350, rs28386840, rs2028455, rs10492503, rs8049651, rs13353224, rs1555322, rs10243024 and rs6570426, wherein the presence of one or more of the risk alleles shown in Table 10 at one or more of said SNPs is indicative of having an MSSS score of 2.5 or greater. For example, the method may comprise determining the genotype of the subject at at least the following positions of SNP: rs2107538, rs1137933, rs1318, rs2069763, rs423904 and rs876493. Methods for assessing multiple sclerosis severity score (MSSS) of a subject may advantageously combine genotyping SNPs as specified above with determining at least 1, 2 or 3 clinical variables selected from: age of the subject at onset of multiple sclerosis, gender of the subject and type of multiple sclerosis at onset of multiple sclerosis. Thus, the method of the invention may comprise assessment of MSSS score utilising a model which combines the SNPs and clinical variables shown in Table 3, Table 3B and/or Table 3C, optionally employing the respective coefficient for each SNP and/or clinical variable shown in column "B" of said table or tables In certain cases, the method of this and other aspects of the invention may be for assessing the probability of increased size and/or distribution of T2 brain lesions in the subject, wherein the method comprises determining the genotype of the subject at at least 2, 3 or 4 of the following positions of SNP: rs2213584, rs2227139, rs2076530 rs876493, rs9808753, rs2074897, rs762550, rs2234978, rs3781202.

In certain cases, the method of this and other aspects of the invention may be for assessing the probability of increased T2 lesion load in the brain, wherein the method comprises determining the genotype of the subject at at least 1, 2, 3 or 4 of the following positions of SNP: rs2107538, rs12861247, rs2074897 and rs7995215, such as determining the genotype of the subject at: rs12861247, rs2074897 and rs7995215.

In certain cases, the method of this and other aspects of the invention may be for assessing an increased number of focal lesions in the spinal cord, wherein the method comprises determining the genotype of the subject at at least 1, 2, 3 or 4 of the following positions of SNP: rs3135388, rs2395182, rs2239802, rs2227139, rs2213584, rs3087456, rs10492972, rs12202350, rs8049651, rs8702 and rs987107, such as determining the genotype of the subject at: rs3135388, rs3087456 and rs2227139.

In certain cases, the method of this and other aspects of the invention may be for assessing the presence of diffuse abnormalities in the spinal cord, wherein the method comprises determining the genotype of the subject at at least 1, 2, 3 or 4 of the following positions of SNP: rs1350666, rs3808585, rs4128767, rs6457594, rs7208257 and rs7956189.

The method in accordance with this and other aspects of the invention may, in some cases, be carried out in vitro using a nucleic acid-containing sample that has been obtained from the subject. In some cases the genotype of the subject at said one or more positions of SNP may be determined indirectly by determining the genotype of the subject at a position of SNP that is in linkage disequilibrium with said one or more positions of SNP, while in some cases the genotype of the subject at said one or more positions of SNP may be determined directly by identifying one or both alleles at said one or more positions of SNP.

In accordance with the method of this and other aspects of the invention, determining the genotype of the subject at said one or more positions of SNP may comprise:
(i) extracting and/or amplifying DNA from a sample that has been obtained from the subject;
(ii) contacting the DNA with an array comprising a plurality of probes suitable for determining the identity of at least one allele at a position of SNP as listed in Table 10, for example using one or more probes selected from those listed in Table 7. In some cases, the array may be a DNA microarray or a bead array.

In accordance with the method of this and other aspects of the invention the method may comprise amplifying DNA from a sample that has been obtained from the subject, wherein said amplifying comprises contacting the DNA with at least one forward primer as listed in Table 8 and at least one reverse primer as listed in Table 9.

In a further aspect, the present invention provides an array of probes for use in a method according to the invention, wherein the array comprises:

at least 5, 10, 15, 20, 50 or more nucleic acid probes suitable for determining the identity of at least one allele at a position of SNP as listed in Table 10; and a solid support on which said probes are immobilised, wherein said probes comprise at least 50%, at least 60%, at least 70%, at least 80%, at least 90%, at least 95%, at least 99% of the total number of nucleic acid probes in the array, or essentially all of the nucleic acid probes in the array. The probes suitable for determining the identity of at least one allele at a position of SNP may be selected from the probes listed in Table 7.

In a further aspect, the present invention provides methods of evaluating disease severity in a patient having multiple sclerosis, including obtaining a DNA sample from the patient, and determining the presence or absence of two or more single nucleotide polymorphisms (SNPs) associated with severity of the disease, wherein the presence of two or more SNPs associated with severity of the disease indicates a likelihood of increased disease severity. In some embodiments the two or more SNPs associated with the disease comprise SNPs in PNMT, IL1R, CCL5, IL2, PITPNC1 or NOS2A. In certain embodiments the two or more SNPs are selected from those listed in Table 10. In certain embodiments, the two or more SNPs associated with the disease are selected from the group consisting of 2073 Intron2 C/T (rs423904), rs876493, rs1137933, rs1318, rs2069763 and rs2107538. In certain embodiments the two or more SNPs associated with the disease are selected from the group consisting of rs3135388, rs2395182, rs2239802, rs2227139, rs2213584, rs3087456 and rs2107538.

The presence or absence of two or more SNPs associated with severity of the disease can be determined by any method known in the art such as a gene chip, bead array, RFLP analysis, and/or sequencing. In some embodiments the two or more SNPs associated with the disease comprise SNPs in PNMT, IL1R, CCL5, IL2, PITPNC1 or NOS2A. In certain embodiments the two or more SNPs associated with the disease are selected from the group consisting of, rs876493, rs1137933, rs1318, rs2069763 and rs2107538. In certain embodiments the two or more SNPs associated with the disease are selected from the group consisting of rs1137933, rs1318, rs2069764 and rs2107538.

Aspects of the invention relate to SNPs associated with increased T2 lesion load in the brain. In some embodiments the SNP is associated with an increased number of focal spinal cord abnormalities. In some embodiments the two or more SNPs are in linkage disequilibrium. In certain embodiments the two or more SNPs are in linkage disequilibrium with SNPs selected from the group consisting of rs2239802, rs2213584, rs3135388, 2213584 rs2227139, rs1137933, rs1318, rs2069764 and rs2107538.

In some embodiments methods described herein further include the measurement of one or more clinical variables such as age of onset, gender, and/or type of onset of disease.

In some embodiments disease severity is based on an MS severity scale such as the Multiple Sclerosis Severity Score (MSSS) test, the Kurtzke Expanded Disability Status Scale (EDSS), or the Multiple Sclerosis Functional Composite (MSFC) measure.

In some embodiments the presence or absence of at least 6 SNPs is determined. In certain embodiments the two or more SNPs are selected from the group consisting of 2073 Intron2 C/T (rs423904), rs876493, rs1137933, rs1318, rs2069763, rs2107538, rs3135388, rs2395182, rs2239802, rs2227139, rs2213584 and rs3087456. In certain embodiments at least one of the SNPs is in linkage disequilibrium with a SNP selected from the group consisting of 2073 Intron2 C/T (rs423904), rs876493, rs1137933, rs1318, rs2069763, rs2107538, rs3135388, rs2395182, rs2239802, rs2227139, rs2213584 and rs3087456. In some embodiments methods described herein include use of one or more probe sets listed in Table 7. In some embodiments methods described herein include at least one forward primer from Table 8 and one reverse primer from Table 9.

Aspects of the invention relate to methods of designing a treatment regimen for a patient having multiple sclerosis, including obtaining a DNA sample from the patient, determining the presence or absence of two or more single nucleotide polymorphisms (SNPs) associated with severity of the disease, wherein the presence of two or more SNPs associated with severity of the disease indicates a likelihood of increased disease severity, and designing the treatment regimen based on the presence or absence of the SNPs associated with the disease. In some embodiments the treatment regimen comprises early or elevated doses of glatiramer acetate, vitamin D, interferon beta-1a or -1b, natalizumab, mitoxantrone, and/or corticosteroids.

Aspects of the invention relate to methods of treating a patient having a prognosis of increased disease severity, comprising early or elevated doses of glatiramer acetate, vitamin D, interferon beta-1 a or -1 b, natalizumab, mitoxantrone, and/or corticosteroids.

Aspects of the invention relate to methods of identifying SNPs associated with severity of symptoms in multiple sclerosis, including obtaining a DNA sample from a patient having multiple sclerosis, identifying SNPs in the DNA, wherein the SNPs comprise two or more of the SNPs listed in Table 1, performing an MRI on the patient to determine spatial distribution of T2 brain lesions, T2 lesion load, presence of diffuse abnormalities and/or number of spinal cord lesions, comparing identified SNPs with the spatial distribution of T2 brain lesions, T2 lesion load, presence of diffuse abnormalities and/or number of spinal cord lesions, and identifying the SNPs that correlate with spatial distribution of T2 brain lesion, T2 lesion load, presence of diffuse abnormalities and/or number of spinal cord lesions, wherein the SNPs that correlate with spatial distribution of T2 brain lesions, T2 lesion load, presence of diffuse abnormalities and/or number of spinal cord lesions, are SNPs associated with severity of symptoms in multiple sclerosis. In some embodiments at least one of the SNPs is in linkage disequilibrium with a SNP listed in Table 1. In some embodiments identifying SNPs associated with severity of symptoms in multiple sclerosis further comprises consideration of clinical data.

Aspects of the invention relate to methods of evaluating disease severity, as measured using the Multiple Sclerosis Severity Score (MSSS) test, the Kurtzke Expanded Disability Status Scale (EDSS), and/or the Multiple Sclerosis Functional Composite measure (MSFC), in a patient having multiple sclerosis, the method including obtaining a DNA sample from the patient, and determining the presence or absence of two or more single nucleotide polymorphisms (SNPs), wherein said SNPs comprise two or more of the SNPs listed in Table 1, and wherein the presence of said two or more SNPs indicates a likelihood of increased disease severity. In some embodiments evaluating disease severity further comprises consideration of clinical data. In some embodiments at least one of the SNPs is in linkage disequilibrium with a SNP listed in Table 1.

Aspects of the invention relate to methods of evaluating the severity of spinal cord lesions in a patient having multiple sclerosis, the method including obtaining a DNA sample from the patient, and determining the presence or absence of two or more single nucleotide polymorphisms (SNPs) associated with spinal cord lesions, wherein the presence of two or more SNPs associated with spinal cord lesions indicates a likelihood of increased disease severity. In some embodiments the two or more SNPs are selected from the group consisting of rs3135388, rs2395182, rs2239802, rs2227139, rs2213584 and rs3087456. In certain embodiments one of the SNPs is rs3135388. In some embodiments the two or more SNPs are selected from the group consisting of 2073 Intron2 C/T (rs423904), rs876493, rs1137933, rs1318, rs2069763, rs2107538, rs3135388, rs2395182, rs2239802, rs2227139, rs2213584 and rs3087456. In certain embodiments at least one of the SNPs is in linkage disequilibrium with a SNP selected from the group consisting of 2073 Intron2 C/T (rs423904), rs876493, rs1137933, rs1318, rs2069763, rs2107538, rs3135388, rs2395182, rs2239802, rs2227139, rs2213584 and rs3087456.

Aspects of the invention relate to method of prognosing the likelihood of T2 lesions and/or T2 lesion load in a patient having multiple sclerosis, the method including obtaining a DNA sample from the patient, and determining the presence or absence of SNP rs2107538, wherein the presence of SNP rs2107538 indicates a likelihood of T2 lesions and/or T2 lesion load in the patient.

Aspects of the invention relate to methods where determining the presence or absence of SNPs includes (a) providing, for each genetic variation to be genotyped, at least 2 oligonucleotide probe pairs, wherein: (i) one pair consists of probes 1 and 2, and the other pair consists of probes 3 and 4; (ii) one probe in each pair is capable of hybridising to genetic variation A and the other probe in each pair is capable of hybridising to genetic variation B; (iii) each probe is provided in replicates; and (iv) the probe replicates are each coupled to a solid support; (c) amplifying and detectably labelling the target DNA; (d) contacting the target DNA with the probes under conditions which allow hybridisation to occur, thereby forming detectably labeled nucleic acid-probe hybridisation complexes, (e) determining the intensity of detectable label at each probe replica position, thereby obtaining a raw intensity value; (f) optionally amending the raw intensity value to take account of background noise, thereby obtaining a clean intensity value for each replica; and (g) applying a suitable algorithm to the intensity data from (e) or (f), thereby determining the genotype with respect to each genetic variation, wherein application of the algorithm comprises calculating an average intensity value from the intensity values for each of the replicas of each probe and wherein the algorithm uses three Fisher linear functions that characterize each of the three possible genotypes AA, AB or BB for the genetic variation.

Aspects of the invention relate to kits for evaluating severity of disease in a subject having multiple sclerosis, the kit including: (i) at least one set of probes listed in table 7; optionally (ii) instruction for genotyping analysis as described in claim H1; and optionally (iii) instructions for determining the severity MS phenotype from the outcomes.

Aspects of the invention relate to PCR amplification kits comprising at least one pair of PCR primers from tables 8 and 9, a thermostable polymerase, dNTPs, a suitable buffer, and optionally instructions for use.

Further aspects of the invention relate to a computational method of deriving a probability function for use in determining an MS severity phenotype in a subject, including applying a probability function such as stepwise multiple logistic regression analysis to outcome data and phenotype data obtained from a suitable study population of individuals, wherein each individual is of known clinically determined phenotype with respect to the Multiple Sclerosis severity phenotype, thereby deriving a probability function which produces a statistically significant separation between individuals of different phenotype in the population; wherein: (i) the phenotype data comprises the known clinically determined phenotype of each individual; (ii) the outcomes data for each individual comprises the genotype of the individual at each SNP in a set of SNPs; and wherein: (a) the probability function is for distinguishing or differentially diagnosing MS severity phenotype, and the set of SNPs is selected from the set of MS severity phenotype discriminating SNPs in Table 3; (b) the probability function is for prognosing MS disease severity phenotype and the set of SNPs is selected from the set of MS disease severity discriminating SNPs in Table 3; and/or (c) the probability function is for prognosing MS disease severity phenotype and the set of SNPs is selected from the set of MS disease severity discriminating SNPs in Table 10.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 1:
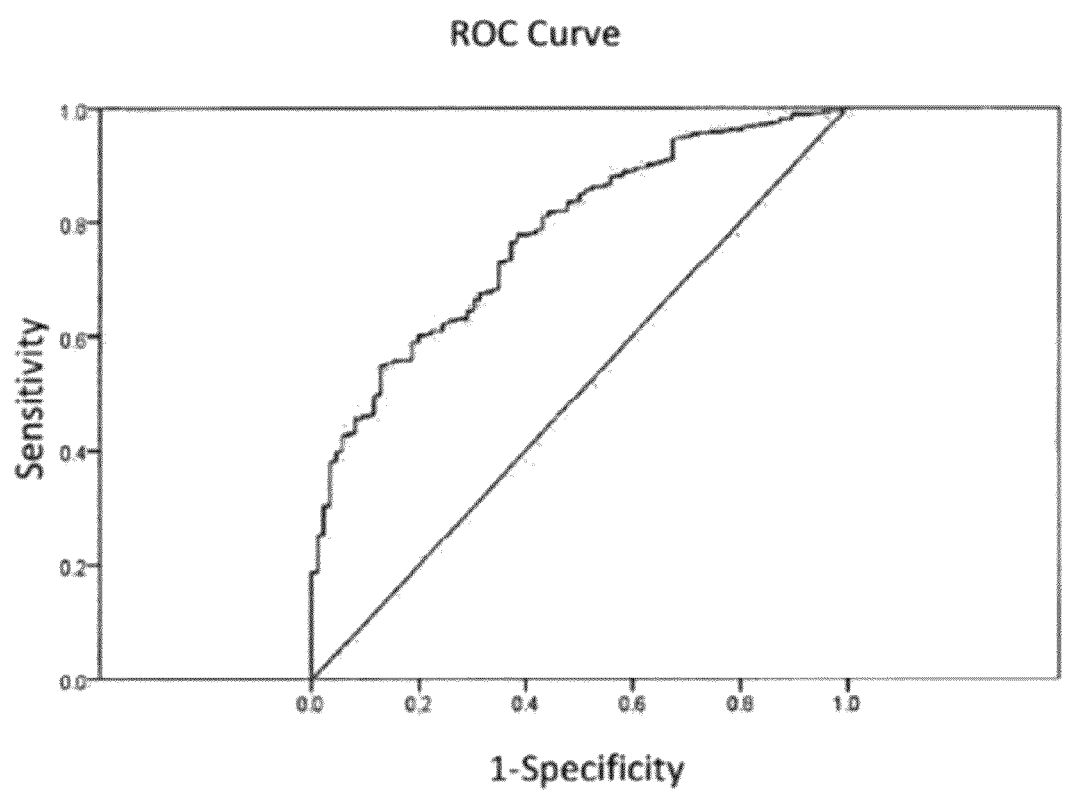
FIG. 1 is a graph showing a ROC (receiver operating characteristic) curve obtained for the model MSSS<2.5 versus≥2.5, showing the relationship between sensitivity (y-axis) and percentage (x-axis).

The Sequence Listing is submitted as an ASCII text file in the form of the file named Sequence_Listing.txt, which was created on Sep. 9, 2011, and is 173,767 bytes, which is incorporated by reference herein.

DETAILED DESCRIPTION

Multiple Sclerosis (MS) is a multifocal inflammatory demyelinating disease of the central nervous system (CNS), characterized by inflammation, demyelination and axonal loss resulting in a highly variable clinical presentation. Most patients suffer from relapsing-remitting (RR) MS, experiencing waves of inflammation leading to alternating periods of disability (relapses) and stable disease (remissions). The RRMS phase usually leads to progressive and irreversible disability (the secondary progressive [SP] phase). For a subset of patients, the disease is progressive from onset (primary progressive [PP] MS). Treatment decisions are based on the occurrence of relapses, and the development of white matter lesions visible on MRI. Brain lesion volume and distribution however are highly variable among MS patients, and correlate only moderately with disability. As treatment guidelines would strongly benefit from a better understanding of this variability, the present invention is drawn to methods of genetic screening and predicting severity of disease using genetic information that correlates with increased numbers of lesions in the brain, optic nerve, or spinal cord.

Aspects of the invention relate at least in part to the surprising discovery that MS severity can be associated (e.g., statistically) with one or more genetic markers. As used herein, a genetic marker refers to a DNA sequence that has a known location on a chromosome. Several non-limiting examples of classes of genetic markers include RFLP (restriction fragment length polymorphism), AFLP (amplified fragment length polymorphism), RAPD (random amplification of polymorphic DNA), VNTR (variable number tandem repeat), microsatellite polymorphism, SNP (single nucleotide polymorphism), STR (short tandem repeat), and SFP (single feature polymorphism).

In some embodiments, genetic markers associated with the invention are SNPs. As used herein a SNP or "single nucleotide polymorphism" refers to a specific site in the genome where there is a difference in DNA base between individuals. In some embodiments the SNP is located in a coding region of a gene. In other embodiments the SNP is located in a noncoding region of a gene. In still other embodiments the SNP is located in an intergenic region. It should be appreciated that SNPs exhibit variability in different populations. In some embodiments, a SNP associated with the invention may occur at higher frequencies in some ethnic populations than in others. In some embodiments, SNPs associated with the invention are SNPs that are linked to MS. In certain embodiments a SNP associated with the invention is a SNP associated with a gene that is linked to MS. A SNP that is linked to MS may be identified experimentally. In other embodiments a SNP that is linked to MS may be identified through accessing a database containing information regarding SNPs. Several non-limiting examples of databases from which information on SNPs or genes that are associated with human disease can be retrieved include: NCBI resources, The SNP Consortium LTD, NCBI dbSNP database, International HapMap Project, 1000 Genomes Project, Glovar Variation Browser, SNPStats, PharmGKB, GEN-SniP, and SNPedia. In some embodiments, SNPs associated with the invention comprise two or more of the SNPs listed in Table 1 and/or Table 10. In some embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 SNPs are evaluated in a patient sample. In some embodiments, multiple SNPs are evaluated simultaneously while in other embodiments SNPS are evaluated separately.

SNPs are identified herein using the rs identifier numbers in accordance with the NCBI dbSNP database, which is publically available at: http://www.ncbi.nlm.nih.gov/projects/SNP/. As used herein, rs numbers refer to the dbSNP build 129, *Homo sapiens* build 36.3 available from 14 Apr. 2008 and/or dbSNP build 131, *Homo sapiens* build 37.1 available from 2 Feb. 2010. Except where indicated otherwise, the rs identifiers are identical for dbSNP build 129, *Homo sapiens* build 36.3 and dbSNP build 131, *Homo sapiens* build 37.1.

In some embodiments, SNPs in linkage disequilibrium with the SNPs associated with the invention are useful for obtaining similar results. As used herein, linkage disequilibrium refers to the non-random association of SNPs at two or more loci. Techniques for the measurement of linkage disequilibrium are known in the art. As two SNPs are in linkage disequilibrium if they are inherited together, the information they provide is correlated to a certain extent. SNPs in linkage disequilibrium with the SNPs included in the models can be obtained from databases such as HapMap or other related databases, from experimental setups run in laboratories or from computer-aided in-silico experiments. Determining the genotype of a subject at a position of SNP as specified herein, e.g. as specified by NCBI dbSNP rs identifier, may comprise directly genotyping, e.g. by determining the identity of the nucleotide of each allele at the locus of SNP, and/or indirectly genotyping, e.g. by determining the identity of each allele at one or more loci that are in linkage disequilibrium with the SNP in question and which allow one to infer the identity of each allele at the locus of SNP in question with a substantial degree of confidence. In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 90%, at least 95% or at least 99% certainty.

As used herein MS or multiple sclerosis refers to a progressive neurodegenerative disease involving demyelination of nerve cells. Several non-limiting classifications of MS include: relapsing-remitting (RRMS) (typically characterized by partial or total recovery after attacks (also called exacerbations, relapses, or flares)), secondary progressive MS (SPMS) (generally characterized by fewer relapses, with an increase in disability and symptoms), and primary progressive MS (PPMS) (generally characterized by progression of symptoms and disability without remission).

Some non-limiting examples of symptoms of MS include: fatigue (also referred to as MS lassitude), muscle fatigue, paresthesias, difficulty in walking and/or balance problems, abnormal sensations such as numbness, prickling, or "pins and needles", pain, bladder dysfunction, bowel dysfunction, changes in cognitive function (including problems with memory, attention, concentration, judgment, and problem-solving), dizziness and vertigo, emotional problems (e.g., depression), sexual dysfunction, and vision problems. In some embodiments, symptoms of MS can include partial or complete paralysis (such as blurred or double vision, red-green color distortion, or blindness in one eye), headache, hearing loss, itching, seizures, spasticity, speech and swallowing disorders, and tremors. In some embodiments, clinical symptoms of MS can include increased CD4:CD8 cell ratio compared to normal, decreased number of CD14+ cells compared to normal, increased expression of HLA-DR on CD14+ cells compared to normal CD14+ cells, increased levels of activated monocytes or macrophages compared to normal, the presence of proliferating macrophages, and decreased serum IgG and/or IgM compared to normal, where "normal" as used in this context refers to a subject who does not have MS.

Previous studies have explored patterns of spatial lesion distribution in MS patients. Without wishing to be bound by any theory, one potential factor underlying differences in lesion burden and spatial lesion distribution among MS patients may be found in pathological and immunological heterogeneity: studies on spatial lesion distribution throughout the brain demonstrated differences in lesion distribution across disease types and across lesion types. These findings of distinct lesion distributions across patient subgroups and lesion types suggest that different subtypes of pathology exist in MS based at least in part on different immunological mechanisms. For example, periventricular predilection of MS lesions may be caused at least in part by differences in the vasculature compared to other regions, making this location vulnerable to pathological changes. Without wishing to be bound by any theory, enhanced lesions in peripheral as opposed to central brain regions may be caused, at least in part, by central lesions developing from progressive gliosis and peripheral lesions being more inflammatory. As lesions in different locations may have different immunological backgrounds, they may warrant different treatment mechanisms. Results described herein suggest that differences in immunological backgrounds of lesion formation among MS patients may be driven by genetic predisposition.

Aspects of the invention relate to a large-scale study investigating the genetic influences on different phenotypes of MS (disease severity, subtype, MRI characteristics, response to treatment). Described herein is an investigation into the correlation between genetic background and spatial lesion distribution in a large cohort of MS patients using a variety of SNPs.

Aspects of the invention relate to evaluating the severity of MS in a patient. One symptom associated with MS is the presence of demyelination (lesions or plaques) in the brain and/or spinal cord of a patient. It should be appreciated that regions of demyelination may be detected through any means known to one of ordinary skill in the art. In some embodiments, lesions are detected through MRI. In some embodiments treatment decisions regarding a patient with MS, are based on the occurrence of relapses and the development of white matter lesions visible on MRI. Brain lesion volume and distribution, however, are highly variable among MS patients and correlate only moderately with disability. Treatment guidelines would benefit from a better understanding of this variability. Differences in genetic background may lead to different lesion distribution, which in turn may lead to a different clinical expression of the disease. Thus, the correlations revealed herein, between the presence of specific genetic markers and the presence of lesions offer important applications for screening of patients who have or are at risk of MS, diagnostic and prognostics for MS patients, as well as development of appropriate therapeutic approaches. As used herein, the term disease severity refers to the evaluation of a patient's disability using the tests listed above or other similar tests known in the art. An assessment of disease severity in some embodiments includes determining rapidity of development of disability, disease duration, rate of progression or relapse of symptoms, and symptoms such as changes in sensation, fatigue, pain, muscle weakness and/or spasm, problems in speech, visual problems, difficulty in moving, difficulties with coordination and balance, bladder and bowel difficulties and cognitive impairment.

Several methods have been established for assessing the severity of MS based on analysis of clinical factors such as those in Table 2, below. Non-limiting examples of tests used to assess the severity of MS include the Kurtzke Expanded Disability Status Scale (EDSS), the Multiple Sclerosis Functional Composite measure (MSFC), and the Multiple Sclerosis Severity Score (MSSS). The MSSS test relates scores on the Expanded Disability Status Scale (EDSS) to the distribution of disability in patients with comparable disease durations. Effectively the MSSS assigns to each EDSS its median decile score within this distribution. For example, an MSSS of 5.0 indicates the disease is progressing at the median rate. A patient whose MSSS is 9.0 is a fast progressor, progressing faster than 90% of patients. A patient whose MSSS is 1.0 is a slow progressor, progressing faster than just 10% of patients. In some embodiments, based on the MSSS test a patient may be assigned a median docile score of 1, 2, 3, 4, 5, 6, 7, 8, 9, or 9.5, including any intermediate values. In some embodiments, based on a test such as the MSSS test, MS patients are allocated into severe and benign subgroups. In some embodiments, MS patients are classified into different categories of severity based on a test such as MSSS. In some embodiments MS patient may be classified as relapsing-remitting (RRMS), secondary progressive MS (SPMS), and primary progressive MS (PPMS).

The invention in one aspect presents a model for assessing the strength of the disability, or the severity of the form of MS, according to the MSSS scale, using SNP analysis, thus allowing differential treatment management for a given patient. Results described herein generate a model from the analysis of 605 MS patients and 700 MS patients (see Example section). In some aspects, the invention evaluates differences between patients that have an MSSS score of less than 2.5 versus patients that have an MSSS score 2.5 or greater. Aspects of the invention relate to using genetic markers that are correlated to certain degrees of MS severity as predictive of MS severity and as indicators of recommended therapeutic approaches. In some embodiments, methods described herein relate to screening a patient for one or more risk factors associated with MS. In some embodiments the presence of two or more of the SNPs described herein indicate a more severe form of MS.

The invention in one aspect relates to correlating specific SNPs or combinations of SNPs with the presence and/or severity of lesions in the brain and/or spinal cord. The SNPs or combinations of SNPs that are correlated to the presence and/or severity of lesions in the brain and/or spinal cord can be used as predictive, diagnostic or prognostic indicators of the presence and/or severity of lesions in the brain and/or spinal cord. The detection of such SNPs, indicating the presence of lesions in the brain and/or spinal cord may in some embodiments be used as an indicator of the severity of MS.

Aspects of the invention relate to determining the presence of SNPs through obtaining a patient DNA sample and evaluating the patient sample for the presence of two or more SNPs. It should be appreciated that a patient DNA sample can be extracted, and a SNP can be detected in the sample, through any means known to one of ordinary skill in art. Some non-limiting examples of known techniques include detection via restriction fragment length polymorphism (RFLP) analysis, planar microarrays, bead arrays, sequencing, single strand conformation polymorphism analysis (SSCP), chemical cleavage of mismatch (CCM), and denaturing high performance liquid chromatography (DHPLC).

In some embodiments, a SNP is detected through PCR amplification and sequencing of the DNA region comprising the SNP. In some embodiments SNPs are detected using microarrays. Microarrays for detection of genetic polymorphisms, changes or mutations (in general, genetic variations) such as a SNP in a DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary, to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

In some embodiments, detection of genetic variation such as the presence of a SNP involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele. In some embodiments, the amplification reaction and/or extension reaction is carried out on the microarray or bead itself.

In some embodiments, methods described herein may involve hybridization. For differential hybridization based methods there are a number of methods for analysing hybridization data for genotyping:

Increase in hybridization level: The hybridization levels of probes complementary to the normal and mutant alleles are compared.

Decrease in hybridization level: Differences in the sequence between a control sample and a test sample can be identified by a decrease in the hybridization level of the totally complementary oligonucleotides with a reference sequence. A loss approximating 100% is produced in mutant homozygous individuals while there is only an approximately 50% loss in heterozygotes. In Microarrays for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. However it should be appreciated that the oligonucleotide can be any length that is appropriate as would be understood by one of ordinary skill in the art. The increased number of oligonucleotides used to reconstruct the sequence reduces errors derived from fluctuation of the hybridization level. However, the exact change in sequence cannot be identified with this method; in some embodiments this method is combined with sequencing to identify the mutation.

Where amplification or extension is carried out on the microarray or bead itself, three methods are presented by way of example:

In the Minisequencing strategy, a mutation specific primer is fixed on the slide and after an extension reaction with fluorescent dideoxynucleotides, the image of the Microarray is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of Microarrays with oligonucleotides complementary to these sequences or "tags" allows the capture of the resultant products of the extension. Examples of this include the high density Microarray "Flexflex" (Affymetrix).

For cost-effective genetic diagnosis, in some embodiments, the need for amplification and purification reactions presents disadvantages for the on-chip or on-bead extension/amplification methods compared to the differential hybridization based methods. However the techniques may still be used to detect and diagnose conditions according to the invention.

Typically, Microarray or bead analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Genome Research; 11:1913-1925 (2001). Methods of genotyping using microarrays and beads are known in the art.

Some non-limiting examples of genotyping and data analysis can be found in co-pending patent application U.S. Ser. No. 11/813,646 (WO 2006/075254), which is hereby incorporated by reference. In some embodiments the genotypes are determined as follows: The signal from the probes which detect the different genetic variations is determined with a scanner. The scanner software executes a function to subtract the local background noise from the absolute signal intensity value obtained for each probe. Next, the replicates for each of the 4 probes that are used to characterize each genetic variation are grouped. The average intensity value for each of 4 probes is calculated using the average collated from the replicates in order to identify abnormal values (outliers) that can be excluded from further consideration. Once the average intensity value for each of the probes is known then two ratios are calculated (ratio 1 and ratio 2):

$$\text{Ratio 1} = \frac{\text{Average intensity for probe 1}}{\text{Average intensity for probe 1} + \text{Average intensity for probe 2}}$$

$$\text{Ratio 2} = \frac{\text{Average intensity for probe 3}}{\text{Average intensity for probe 3} + \text{Average intensity for probe 4}}$$

wherein probe 1 detects (is capable of specifically hybridising to) genetic variation A (e.g. a normal allele), probe 2 detects (is capable of specifically hybridising to) genetic variation B (e.g. a mutant allele), probe 3 detects (is capable of specifically hybridising to) genetic variation A (e.g. a normal allele) and probe 4 detects (is capable of specifically hybridising to) genetic variation B (e.g. a mutant allele).

These ratios are substituted in three Fisher linear functions which characterize each one of the three possible genotypes:

| | |
|---|---|
| AA | Function 1 |
| AB | Function 2 |
| BB | Function 3 |

The function which presents the highest absolute value determines the genotype of the patient.

The Fisher linear functions are obtained by analyzing 3 subjects for each of the three possible genotypes of the genetic variation (AA, AB, BB). With the results, ratios 1 and 2 are calculated for the SNPs analyzed and for the 3 subjects. These ratios are classification variables for the three groups to create the linear functions, with which the discriminatory capacity of the two pairs of designed probes is evaluated. If the discriminatory capacity is not 100%, the probes are redesigned. New subjects characterized for each of the three genotypes make up new ratios 1 and 2 to perfect the linear functions and in short, to improve the discriminatory capacity of the algorithm based on these three functions.

When using a fluorescent laser, to obtain reliable results it is preferable that ratios 1 and 2 are within the range of the ratios used to build the groups.

Again when a fluorescent scanner is used in the experiment, for a complete hybridization to be considered reliable preferably the ratio of probe fluorescence intensity to background noise of all the beads DNA array probes is above 15. Likewise, the average of all the ratios is preferably above 0.6 and the negative control is preferably less than or equal to 3 times the background noise.

In summary, four probes are presented in the hybridization analysis for detection of each mutation. Two of the probes detect one genetic variation (A) and the other two the other genetic variation (B). The examined base is located in the central position of the probes.

A subject homozygous for the genetic variation A will not show genetic variation B. Consequently, the probes which detect genetic variation B will show a hybridization signal significantly less than that shown by variation A and vice versa. In this case the ratios 1 and 2 will show 1 and the subjects will be assigned as homozygous AA by the software analysis.

On the other hand, a heterozygous subject for the determined genetic variation shows both the genetic variations. Therefore, the probes which detect them show an equivalent hybridization signal. The ratios 1 and 2 will show 0.5 and the subject will be assigned as heterozygous AB the software analysis as described.

In one aspect of the invention, DNA polymorphisms are selected based on their association with the etiology of MS, such as those shown in Table 1 below:

TABLE 1

| Gene | RefSNP accession I.D. |
|---|---|
| ACCN1 | rs28936 |
| ACE | rs4343 |
| ADAMTS14 | rs4747075 |
| ADAMTS14 | rs7081273 |
| ADAMTS14 | rs4746060 |
| ALK | rs7577363 |
| ANKRD15 | rs10975200 |
| Apo I/Fas | rs1800682 |
| Apo I/Fas | rs3781202 |
| Apo I/Fas | rs2234978 |
| BDNF | rs6265 |
| BTNL2 | rs2076530 |
| C10orf27 | rs2254174 |
| C10orf27 | rs12221473 |
| C10orf27 | rs12221474 |
| C10orf27 | rs2791196 |
| CACNG4 | rs4790896 |
| CBLB | rs12487066 |
| CCL11 | rs17735961 |
| CCL14 | rs854682 |
| CCL17 | rs223828 |
| CCL2 | rs1024610 |
| CCL22 | rs4359426 |
| CCL23 | rs1003645 |
| CCL23 | rs854655 |
| CCL5 | rs2107538 |
| CCL5 | rs2280788 |
| CCR5 | rs333 |
| CD14 | rs2569190 |
| CD226 | rs763361 |
| CD24 | rs8734 |
| CD58 | rs12044852 |
| CNTF | rs1800169 |
| CRYAB | rs14133 |
| CRYAB | rs762550 |
| CRYAB | rs2234702 |
| CTLA4 | rs231775 |
| CTLA4 | rs5742909 |
| CTSS | rs1136774 |
| CTSS | rs3754212 |
| CXLCL10 | rs3921 |
| CXLCL10 | rs8878 |
| DBC1 | rs10984447 |
| DRB1 | rs3135388 |
| EBF | rs1368297 |
| EVI5 | rs10735781 |
| EVI5 | rs6680578 |
| FAM69A | rs11164838 |
| FAM69A | rs7536563 |
| GABBRA1 | rs1805057 |
| GLO1 | rs2736654 |
| GR | rs6189 |
| GR | rs6190 |
| HELZ | rs2363846 |
| HFE | rs1800562 |
| HLA | rs2395166 |
| HLA | rs2213584 |
| HLA | rs2227139 |
| HLA | rs3135388 |
| HLA | rs9268458 |
| HLA | rs6457594 |
| HLA-DRA | rs2395182 |
| HLA-DRA | rs2239802 |
| ICOS | rs4404254 |
| ICOS | rs10932036 |
| ICOS | rs4675379 |
| IFI30 | rs11554159 |
| IFNAR | rs1012334 |
| IFNAR1 | rs2257167 |
| IFNG | rs1861494 |
| IFNG | rs2069727 |
| IFNG | rs2430561 |
| IFNG | rs3181034 |
| IFNG | rs7954499 |
| IFNGR2 | rs9808753 |
| IKBL | rs3130062 |
| IL10 | rs1800871 |
| IL10 | rs1800872 |

TABLE 1-continued

| Gene | RefSNP accession I.D. |
|---|---|
| IL10 | rs1800896 |
| IL1A | rs1800587 |
| IL1B | rs1799916 |
| IL1B | rs1143627 |
| IL1B | rs1143634 |
| IL1RN | 2073 Intron2 C/T (rs423904) |
| IL1RN | rs419598 |
| IL2 | rs2069763 |
| IL2 | rs2069762 |
| IL23R | rs7517847 |
| IL23R | rs11209026 |
| IL2RA | rs12722489 |
| IL2RA | rs2104282 |
| IL4R | rs1801275 |
| IL5RA | rs2290608 |
| IL7R | rs11567685 |
| IL7R | rs7718919 |
| IL7R | rs11567686 |
| IL7R | rs6897932 |
| IL7R | rs3194051 |
| IL7R | rs987106 |
| IL7R | rs987107 |
| IL7R | rs11567685 |
| IL7R | rs7718919 |
| IL7R | rs11567686 |
| IL8 | rs4073 |
| IRF1 | rs2070721 |
| IRF5 | rs3807306 |
| IRF5 | rs4728142 |
| IRF5 | 5 bp insertion-deletion polymorphism located in the promoter and first intron of the IRF5 gene |
| IRF-5 | rs10954213 |
| IRF-5 | rs2004640 |
| IRF-5 | rs2280714 |
| IRF-5 | rs3757385 |
| ITGA4 | rs1449263 |
| KCNH7 | rs2068330 |
| KIAA0350 | rs6498169 |
| KLC1 | rs8702 |
| KLRB1 | rs4763655 |
| LAG3 | rs1922452 |
| LAG3 | rs870849 |
| LAG3 | rs951818 |
| LAG3 | rs19922452 |
| LMP7 | rs2071543 |
| MBP | rs470929 |
| MC1R | rs1805009 |
| MC1R | rs1805006 |
| MEFV | rs28940577 |
| MGC33887 | rs987931 |
| MHC2TA | rs4774 |
| MHC2TA | rs3087456 |
| MOG | rs2857766 |
| MOG | rs3130250 |
| MOG | rs3130253 |
| MxA | rs2071430 |
| NDUFA7 | rs2288414 |
| NDUFA7 | rs561 |
| NDUFS5 | rs2889683 |
| NDUFS5 | rs6981 |
| NDUFS7 | rs2074897 |
| NOS2A | rs1137933 |
| NOS2A | rs2779248 |
| NOTCH4 | rs367398 |
| NR4A2 | rs1405735 |
| OAS1 | rs10774071 |
| OAS1 | rs3741981 (rs1131454 in version. 37.1) |
| PD-1 | rs11568821 |
| PDE4B | rs1321172 |
| PITPNC1 | rs1318 |
| PITPNC1 | rs2365403 |
| PNMT | rs876493 |
| PON | rs854560 |
| PPARG | rs1801282 |
| PRKCA | rs7220007 |
| PRKCA | rs887797 |
| PRKCA | rs2078153 |
| PRKCA | rs3890137 |
| PTPN22 | rs2476601 |
| PTPRC | rs17612648 |
| PTPRC | rs4915154 |
| PVRL2 | rs394221 |
| RPL5 | rs6604026 |
| SELE | rs1805193 |
| SELE | rs5361 |
| SPARCL1 | rs1049544 |
| Spp1 | rs1126616 |
| Spp1 | rs1126772 |
| Spp1 | rs2853744 |
| Spp1 | rs9138 |
| Spp1 | rs4754 |
| STAT1 | rs1547550 |
| STAT1 | rs2066802 |
| TAC1 | rs2072100 |
| TAC1 | rs7793277 |
| TGFB1 | rs1800469 |
| TGFB1 | rs1800470 |
| TGFB1 | rs1800471 |
| TGFB1 | rs1982073 |
| TNF-alpha | rs1800629 |
| TRAIL | rs1131568 |
| TRIF (TICAM1) | rs1046673 |
| TRIF (TICAM1) | rs2292151 |
| UCP2 | rs659366 |
| VDR | rs10735810 |
| VDR | rs1544410 |
| VDR | rs731236 |

Each individual in the study population is tested to determine an outcome for each of the discriminating variables for the particular phenotype. This provides a number of outcomes for each individual. Testing, e.g. genotyping, may be carried out by any of the methods described herein, e.g. by microarray analysis as described herein. Testing is typically ex vivo, carried out on a suitable sample obtained from an individual.

Multiple genotype-phenotype associations may then be analysed using stepwise multivariate logistic regression analysis, using as the dependent variable the clinically determined MS phenotype and as independent variables the outcomes of the informative variables. The goodness of fit of the models obtained may be evaluated using Hosmer-Lemeshow statistics and their accuracy assessed by calculating the area under the curve (AUC) of the Receiver Operating Characteristic curve (ROC) with 95% confidence intervals (see, e.g. (Janssens A C J W et al., 2006)).

Mean probability function values for each of the alternative phenotypes in the population can be compared using a t test. In general the probability functions are able to distinguish between the different phenotypes in the study population in a statistically significant way, for example, at p≤0.05 in a t-test. Thus the probability functions produce a statistically significant separation between individuals of different phenotype in the population.

In some embodiments, the presence of two or more genetic markers in a sample from an MS patient is compared to the presence of two or more genetic markers in a control sample. In some embodiments a control sample is a sample from an individual who does not have MS. In other embodiments a control sample is a sample from an individual who has MS. In certain embodiments, a control sample is a sample from an individual who has MS of a specified classification or degree of severity. It will be understood that the interpretation of a comparison between a test sample and a control sample will depend on the nature of both samples. One possible measurement of the level of expression of genetic markers in a sample is the absolute number of genetic markers identified in a sample. Another measurement of the level of expression of genetic markers in a sample is a measurement of the specific combination of genetic markers in a sample.

In some embodiments, a control value may be a predetermined value, which can take a variety of forms. It can be a single cut-off value, such as a median or mean. It can be established based upon comparative groups, such as in groups not having MS, or groups have specified classifications or levels of severity of MS. For example, in some embodiments, a control sample that is taken from an individual who does not have MS, may be considered to exhibit control or normal patterns of expression of genetic markers for MS. In some embodiments where severity of MS is being assessed, a control sample that is taken from an individual that has a specified classification or level of severity of MS, such as a mild form of MS, may be considered to exhibit a normal or control pattern of expression of markers for MS. In some embodiments a control sample will be from an individual who is of the same ethnic background, gender, age, MS classification and/or MS disease duration as the individual who is being screened and/or diagnosed.

Based at least in part on results of correlations and methods discussed herein, predetermined values can be arranged. For example, test samples and subjects from which the samples were extracted can be divided into groups such as low-severity, medium-severity, and high-severity groups based on the presence of two or more genetic markers that are correlated to MS severity. In some embodiments the classification of a sample and subject into a group can be used to aid or assist in screening, diagnosis, prognosis or development of a treatment strategy for a given subject.

Described herein are correlations between the presence of specific genetic markers and the severity of symptoms of MS in a patient. Such correlations and methods for detecting such correlations have widespread applications for MS patients. In some embodiments methods described herein are used to screen patients who have or are at risk of having MS. In some embodiments, evaluation of the presence of two or more SNPs in a patient will be used to assist in the diagnosis or to indicate or evaluate the severity of MS in the patient. In some embodiments, genetic information obtained from methods described herein will be combined with other clinical data to assess the severity of MS in a given patient.

In some embodiments, the identification of two or more SNPs in a DNA sample from an MS patient will be used to initiate or change a treatment regimen for the patient. For example, in some embodiments, detection of two or more SNPs that are associated with increased severity of MS may cause a physician to change the treatment strategy of an MS patient in order to target a more severe form of the disease, or advise a patient that they may benefit from a change in treatment strategy. In some embodiments, detection of two or more SNPs that are associated with increased severity of MS may cause a physician to monitor an MS patient more closely or rigorously. In some embodiments, detection of two or more SNPs that are associated with increased severity of MS may cause a physician to recommend or advise that a patient undergo genetic counseling.

In some aspects of the invention measurement of clinical variables comprises part of the severity prediction model along with the genetic variables in Table 1, above. Some non-limiting examples are age at onset, gender of patient studied, and type of onset of the disease (e.g. progressive or relapsing) (see Table 2). Age at onset refers to the age in years at which the patient was diagnosed with MS. In the present models this measure has been treated as a continuous variable, which is included in the logistic regression function of the models. Thus an outcome for this variable is age of patient when diagnosed for MS.

Gender refers to the gender of the patient diagnosed with MS. In the present models this measure has been treated as a categorical variable, with levels "male" and "female", which is included in the logistic regression function of the models. Thus an outcome for this variable is gender of patient diagnosed with MS. If the gender is male, this is coded as (1), and if the gender is female, this is coded as (0).

Type of onset refers to the type of onset of disease, progressive or relapsing, for the studied patient diagnosed with MS. In the present models this measure has been treated as a categorical variable, which is included in the logistic regression function of the models. Thus an outcome for this variable is age of patient when diagnosed for MS. If the type of onset is progressive, this is coded as (1), and if the type of onset is relapsing, this is coded as (0).

TABLE 2

Clinical Variables

| Variable | Variable Type |
|---|---|
| Age at onset (Age_at_onset) | Continuous variable |
| Gender | Categorical variable |
| Onset type (Onsettype_cod) | Categorical variable |

In embodiments comprising methods of evaluation of MS severity in a patient, the method typically comprises determining or obtaining for the subject, an outcome for each of the variables listed in Table 2. In some embodiments, use of the results of the measurements of these variables, along with the variables in Table 1, allows prognosis of MS severity phenotype in a Dutch population with an LR+ of 8.4. Details for the calculation of a probability function using these variables are given in Table 3.

Preferably the number and combination of variables such as SNPs used to construct a model for predicting a phenotype according to the invention, is such that the model allows prediction to be made with an LR+ value of at least 1.5, such as at least 2, 3, 4, 5, 6, 7, 8, 9, or 10. Calculation of LR+ values is described herein.

Once an outcome is determined for each of the variables for prediction of a given phenotype, these outcomes are used in or inserted in a suitable probability function (for prediction of that phenotype), as described herein and a probability function value is calculated. Outcomes may be codified for use in the probability function and calculation of the probability function value. The probability function value is then compared with probability function values obtained for a population of individuals of known (clinically determined) phenotype. The risk of the subject having or developing the particular phenotype is thereby determined.

The sensitivity, specificity, and positive likelihood ratio (LR+=sensitivity/(1−specificity)) may be computed by means of ROC curves. Preferably the model has an LR+ value of at least 1.5, for example, at least 2, 3, 4, 5, 6, 7, 8, 9 or 10.

Also within the scope of the invention are kits and instructions for their use. In some embodiments kits associated with the invention are kits for identifying two or more SNPs within a patient sample. In some embodiments a kit may contain primers for amplifying a specific genetic locus. In some embodiments, a kit may contain a probe for hybridizing to a specific SNP. A kit of the invention can include a description of use of the contents of the kit for participation in any biological or chemical mechanism disclosed herein. A kit can include instructions for use of the kit components alone or in combination with other methods or compositions for assisting in screening or diagnosing a sample and/or determining a treatment strategy for MS.

The kits described herein may also contain one or more containers, which may contain a composition and other ingredients as previously described. The kits also may contain instructions for mixing, diluting, and/or administering or applying the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition (e.g., a primer) provided is a dry powder, the composition may be reconstituted by the addition of a suitable solvent, which may also be provided. In embodiments where liquid forms of the composition are used, the liquid form may be concentrated or ready to use. The solvent will depend on the composition and the mode of use or administration. Suitable solvents for drug compositions are well known, for example as previously described, and are available in the literature. The solvent will depend on the composition and the mode of use or administration.

As used herein, the term "subject" refers to a human or non-human mammal or animal. Non-human mammals include livestock animals, companion animals, laboratory animals, and non-human primates. Non-human subjects also specifically include, without limitation, chickens, horses, cows, pigs, goats, dogs, cats, guinea pigs, hamsters, mink, and rabbits. In some embodiments of the invention, a subject is a patient. As used herein, a "patient" refers to a subject who is under the care of a physician or other health care worker, including someone who has consulted with, received advice from or received a prescription or other recommendation from a physician or other health care worker. A patient is typically a subject having or at risk of having MS.

The term "treatment" or "treating" is intended to relate to prophylaxis, amelioration, prevention and/or cure of a condition (e.g., MS). Treatment after a condition (e.g., MS) has started aims to reduce, ameliorate or altogether eliminate the condition, and/or its associated symptoms, or prevent it from becoming worse. Treatment of subjects before a condition (e.g., MS) aims to reduce the risk of developing the condition and/or lessen its severity if the condition does develop. As used herein, the term "prevent" refers to the prophylactic treatment of a subject who is at risk of developing a condition (e.g., MS) resulting in a decrease in the probability that the subject will develop the disorder, and to the inhibition of further development of an already established disorder.

Treatment for MS varies with the stage of the disease and the clinical presentation of the patient. In general it is advantageous to begin treatment early in the course of the disease. Goals for treatment may include slowing the progression of the disease, reducing the number of the attacks, and improving recovery from attacks. Corticosteroids such as Methylprednisolone (Solu-Medrol®, Medrol, Depo-Medrol), and Prednisone (Deltasone®, Liquid Pred, Orasone, Prednicen-M) are used to treat exacerbations of MS. In some embodiments Methylpredisone is given intravenously for 2-7 days, followed by a course of Prednisone. Corticosteroids may be used only for very severe attacks, as the effects vary and there are numerous reported side effects.

In some embodiments an MS patient is treated with therapies that can modify the course of the disease. Certain immune modulatory therapies are thought to slow the progression of MS by tempering the immune system's attack on the central nervous system. Some non-limiting examples include Interferon beta-1a, Interferon beta-1b, and Glatiramer acetate. Some examples of Interferon beta-1a include Avonex® and Rebif®. Avonex® is typically administered by intramuscular injection once weekly, whereas Rebif® is typically administered subcutaneously 3 times per week, at a dose of 22 or 44 mcg. Interferon beta-1b, e.g. Betaseron, is in some embodiments given by subcutaneous injection ever other day. Patients treated with interferon may experience fewer relapses or faster recovery from attacks, and an overall slowing of the progression of the disease. Glatiramer acetate, e.g. Copaxone®, is a synthetic amino acid that modifies actions of the immune system that may affect the progression of MS. It has been shown to reduce the frequency of exacerbations and the level of disability. In some embodiments this medication is given subcutaneously daily.

Other immune modulatory therapies include Natalizumab (Tysabri®), a monoclonal antibody against VLA-4, Mitoxantrone (Novantrone®), a chemotherapy drug. Natalizumab is administered via monthly intravenous injections and has been shown to reduce the frequency of clinical relapses and delay the progression of physical disability. Mitoxantrone is used for reducing neurologic disability and/or the frequency of clinical relapses. In some embodiments vitamin D is used as a treatment.

Other treatments for relief from complications of the disease are aimed at specific to symptoms, such as muscle spasticity, weakness, eye problems, fatigue, emotional outbursts, pain, bladder dysfunction, constipation, sexual dysfunction, and tremors.

EXAMPLES

In multiple sclerosis (MS), the total volume of spinal and brain lesions and their spatial distribution are highly variable. Elucidating this variability may contribute to understanding clinical heterogeneity in MS.

Materials and Methods

Study Participants:
Patients were selected retrospectively from natural history studies conducted at the MS Center at the VU University Medical Center in Amsterdam. Patients were selected for the availability of DNA material, as well as spinal cord and brain MRI, which fulfilled certain standardization requirements and were performed less than two years apart. The study was carried out with the approval of the Medical Ethical Committee of the VUmc and informed consent was obtained from all participants. Patients, all diagnosed with MS ascertained by Poser or McDonald criteria (Poser et al., Ann. Neurol 1983; 3:227-231; Polman C H et al., Ann. Neurol. 2005; 6:840-846). For the patients included in the analysis, clinical data were collected including age, gender, type of disease onset, age at onset, disease course and duration of disease. Disability status was determined for all subjects by using Kurtzke's Expanded Disability Status Scale (EDSS) and when available Multiple Sclerosis Functional Composite scale (MSFC).

Selection of SNPs:
Polymorphisms were selected based on published involvement in MS pathogenesis, prognosis and response to treatment. The polymorphisms were confirmed and associated to an identifier by using dbsnp database (www.ncbi.nlm.nih.gov/SNP). Nucleotide sequences for the design of allele-specific probes and PCR primers where retrieved in the SNPper database (http://snpper.chip.org/bio). Sequence specific probes and primers were designed by using the software Primer3 freely available at http://frodo.wi.mit.edu/. Some non-limiting examples of probes and primers useful in the instant invention can be found in Tables 7-9.

If a polymorphism was not present in the database, position and sequences were established by performing a blast search (http://www.ncbi.nlm.nih.gov.catalog.llu.edu/BLAST/) using the data available in the literature.

Genotyping

Genomic DNA was isolated from anti-coagulated blood with DNAzol reagent (Molecular Research Center, Inc., Cincinnati, Ohio).

Genotyping was carried out using a newly developed low-density DNA microarray based on allele-specific probes. The design, fabrication, validation and analysis of the arrays were performed following the procedure described by Tejedor et al. (2005), *Clin. Chem.*, Vol. 51(7), pp. 1137-1144, with minor modifications.

Brain MRI

Scans were acquired either on 1.0 Tesla or 1.5 Tesla (Siemens) scanners with standard head coils, using standard 2D conventional or fast spin-echo PD- and T2-weighted images (TR: 2200-3000 ms, TE: 20-30 & 80-100 ms) with a slice thicknesses of 3-5 mm, a maximum gap between slices of 0.5 mm, and an in-plane resolution of 1×1 mm$^2$. Lesions were identified by an expert reader and then outlined on the corresponding PD image using home-developed semi-automated seed-growing software based on a local thresholding technique. Lesion areas were multiplied with the interslice distance to obtain total T2 brain lesion volume for each patient.

Spinal Cord MRI:

Spinal cord scanning included a cardiac-triggered sagittal PD and T2-weighted dual-echo spin echo sequence with a slice-thickness of 3 mm covering the whole spinal cord (TR: 2500-3000 ms, TE: 20-30 & 80-100 ms) with an in plane resolution of 1×1 mm. From this sequence the number of focal abnormalities and the presence of diffuse abnormalities were scored by one experienced reader (CL). Diffuse abnormalities were defined as areas with poorly delineated areas of increased signal intensity compared to signal intensity of spinal CSF on intermediate-weighted images.

Statistical Methods for MRI Data:

First the association between the brain parameter (T2 lesion load) and spinal cord parameters (number of focal lesions, presence of diffuse abnormalities) were tested per SNP and per clinical variable. The non-parametric Kruskal-Wallis test and ChiSquare test were used appropriately, applying the False Discovery Rate (FDR) according to Benjamini and Hochberg (Benjamini, Y, 1995, J. R. Stat. Soc. B Met 289) to correct for multiple testing. The corrected number represents the expected proportion false discoveries for a given p-value cut-off. The cut-off point after FDR correction of p<0.05 was used. Pearson's correlation coefficient was used to test the correlations between two scaled variables. All analyses were performed using SPSS (version 15; SPSS Inc., Chicago, Ill., USA).

Statistical Methods for Regression and Association Analysis:

First the association between MS severity score, the brain parameter (T2 lesion load) and spinal cord parameters (number of focal lesions, presence of diffuse abnormalities) were tested per SNP and per clinical variable and statistically significant associations between particular genotypes and particular phenotypes are identified. Methods for determining statistical significance are known in the art. Models were created by means of multivariate logistic and/or linear regression, for categorical or continuous dependent variables respectively, with clinically determined disease phenotypes as dependent variables and the SNPs and clinical variables as independent variables or regressors. To evaluate the impact of the regressors included in the prognosis of the analysed phenotypes, the sensitivity, specificity and positive likelihood ratio (LR+=sensitivity/(1−specificity)) were computed by means of Receiver Operating Characteristic curves. In the case of multiple linear regression, the impact of the regressors the corrected R square was computed. All analyses were performed using the Statistical Package for the Social Sciences (SPSS) version 15 and HelixTree (Golden Helix, Inc., Bozeman, Mont.).

Example 1

Identification of Polymorphisms Associated with Increased MSSS Score

The invention presents a model for predicting the probability of having a stronger disability, as measured by the MSSS scale, thus allowing differential treatment management for a given patient. This model was obtained from the analysis of 605 MS patients. The invention evaluates differences between patients that have an MSSS score of less than 2.5 versus patients that have an MSSS score of 2.5 or greater.

Table 3 (shown below) shows the six SNPs (rs876493, rs1137933, rs1318, rs2069763, rs2107538 and 2073 Intron2 C/T (rs423904)) with the associated genotypes and the three clinical variables (age at onset, gender and onset type) and the associated levels, together with their significance (Sig.), the coefficients in the model (B) and their odds ratios (OR) with lower and upper bound confidence intervals (I.C 95.0% for OR) used to compute the model for the prediction of the MSSS<2.5 versus≥2.5 phenotype. This model provides the probability to develop a severe form of MS.

TABLE 3

Regression Analysis

| Variable name | Genotype/ Variable level | Sig. | B | OR | I.C. 95% for OR Lower bound | Upper bound |
|---|---|---|---|---|---|---|
| IL1RN 2073 Intron2 C/T (rs423904) | CC vs CT/TT | 0.064 | −0.469 | 0.625 | 0.381 | 1.028 |
| PNMT rs876493 | AA/AG vs GG | 0.025 | −0.65 | 0.522 | 0.295 | 0.923 |
| Age_at_onset | | 0.004 | 0.048 | 1.049 | 1.016 | 1.083 |
| gender | 0 = female vs 1 = male | 0.017 | 0.684 | 1.982 | 1.127 | 3.485 |
| Onsettype_cod | 0 = relapsing vs 1 = progressive | 0.021 | 1.466 | 4.331 | 1.244 | 15.082 |

TABLE 3-continued

Regression Analysis

| Variable name | Genotype/Variable level | Sig. | B | OR | I.C. 95% for OR Lower bound | Upper bound |
|---|---|---|---|---|---|---|
| NOS2A rs1137933 | GG vs AG/AA | 0.005 | −0.715 | 0.489 | 0.298 | 0.803 |
| PITPNC1 rs1318 | AA vs AG/GG | 0.002 | −0.775 | 0.461 | 0.28 | 0.759 |
| IL2 rs2069763 | GG vs GT/TT | 0.001 | −0.922 | 0.398 | 0.23 | 0.688 |
| CCL5 rs2107538 | CC vs CT/TT | 0.023 | 0.649 | 1.914 | 1.092 | 3.355 |

FIG. 1 shows a ROC (receiver operating characteristic) curve obtained for the model MSSS<2.5 versus≥2.5 that allows the estimation of its discriminatory power. The ROC curve was calculated in order to maximize the specificity, thus reducing at the same time the "false" positive rate. A specificity of 95.3% with a sensibility of 39.7% is the cut-off for this model regarding the phenotype MSSS<2.5 versus≥2.5. This model shows a positive likelihood ratio (LR+) value of 8.4.

Additional MS patients have been recruited increasing the MS cohort to 700 MS patients. In a first stage of analysis, feature selection was employed to identify the most important and predictive features in the model to be analyzed. This approach of variable filtering is based on the marginal association between each variable (SNP or clinical variable) and phenotype, as variables are typically filtered on the basis of a p-value cut-off from a univariate analysis. For the selection of variables, HelixTree® software (Golden Helix, Inc., Bozeman, Mont., USA) was used to calculate allelic association between different groups. In Table 3A, SNPs associated with MSSS score at a significance level of p<0.1 set as the decision threshold are shown.

TABLE 3A

Table showing the 37 SNPs associated with MSSS score at the selected significance level

| Rs-number SNP | Gene | Sig. p-value |
|---|---|---|
| rs3756450 | LOC728594 | 0.00436 |
| rs12047808 | C1orf125 | 0.00883 |
| rs10259085 | C1GALT1 | 0.00949 |
| rs1042173 | SLC6A4 | 0.01142 |
| rs1318 | PITPNC1 | 0.01426 |
| rs6077690 | SNAP25 | 0.02478 |
| rs1611115 | DBH | 0.02577 |
| rs2107538 | CCL5 | 0.03258 |
| rs4473631 | MORF4 | 0.03348 |
| rs2032893 | SLC1A3 | 0.03470 |
| rs2066713 | SLC6A4 | 0.03744 |
| rs260461 | ZNF544 | 0.03924 |
| rs3787283 | SNAP25 | 0.03976 |
| rs1137933 | NOS2A | 0.04094 |
| rs6917747 | IGF2R | 0.04710 |
| rs2049306 | CSMD1 | 0.04909 |

TABLE 3A-continued

Table showing the 37 SNPs associated with MSSS score at the selected significance level

| Rs-number SNP | Gene | Sig. p-value |
|---|---|---|
| rs12861247 | STS | 0.05177 |
| rs4404254 | ICOS | 0.05585 |
| rs4680534 | IL12A | 0.05729 |
| rs17641078 | DMRT2 | 0.05833 |
| rs2187668 | HLA-DQA1 | 0.06045 |
| rs7528684 | FCRL3 | 0.06099 |
| rs876493 | PNMT | 0.06135 |
| rs7577925 | FLJ34870 | 0.06232 |
| rs1805009 | MC1R | 0.06375 |
| rs423904 | IL1RN | 0.06449 |
| rs3741981 (rs1131454 in version. 37.1) | OAS1 | 0.06993 |
| rs2069763 | IL2 | 0.07750 |
| rs12202350 | IGF2R | 0.07981 |
| rs28386840 | SLC6A2 | 0.08145 |
| rs2028455 | LOC647094 | 0.08244 |
| rs10492503 | GPC5 | 0.08486 |
| rs8049651 | GRIN2A | 0.08826 |
| rs13353224 | DSEL | 0.08906 |
| rs1555322 | MMP24 | 0.09161 |
| rs10243024 | MET | 0.09398 |
| rs6570426 | LOC729293 | 0.09635 |

A Multivariate prognostic model was then constructed for dichotomous MSSS with the cut-off point of 2.5 using logistic regression model, using SPSS version 15.0 (SPSS Inc. Headquarters, Chicago, Ill., USA) and R packages Design (Harrell, 2001) and Stats (R Development Core Team, 2008). The model was developed including information for the clinical variables available.

Figure 5:
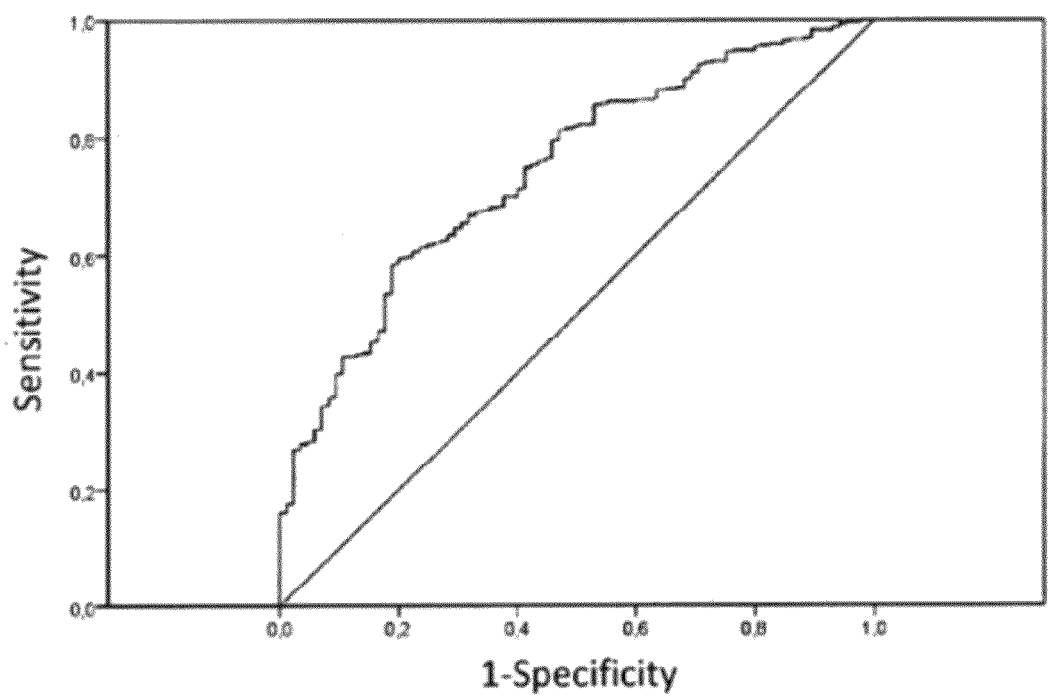
FIG. 5 is a graph showing a ROC (receiver operating characteristic) curve obtained for the model MSSS<2.5 versus≥2.5, showing the relationship between sensitivity (y-axis) and percentage (x-axis), as further described in Table 3B.
Figure 6:
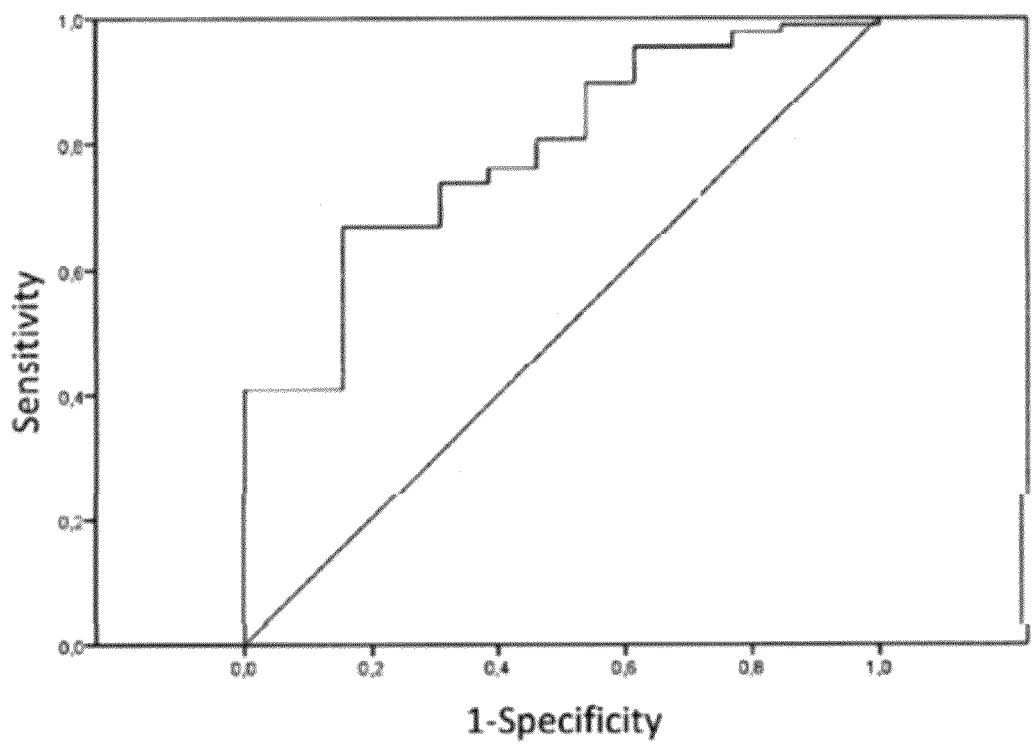
FIG. 6 is a graph showing a ROC (receiver operating characteristic) curve obtained for the model MSSS<2.5 versus≥2.5, showing the relationship between sensitivity (y-axis) and percentage (x-axis), as further described in Table 3B.

85% of the cohort was selected at random as exploratory cohort (n=595) and the 15% of the cohort as replication cohort (n=105). The model obtained with the exploratory cohort (Table 3B) included the same variables as the one obtained from the analysis of 605 MS patients (Table 3). The model showed in Table 3B was validated in the replication cohort (AUC exploratory cohort=0.743 (0.691-0.796) (FIG. 5) versus AUC replication cohort=0.787 (0.667-0906) (FIG. 6), differences between both ROC curves not statistically significant).

TABLE 3B

Regression Analysis

| Variable name | Genotype/Variable level | Sig. | B | OR | I.C. 95% for OR Lower bound | Upper bound |
|---|---|---|---|---|---|---|
| IL1RN 2073 Intron2 C/T (rs423904) | CC vs CT/TT | 0.056 | −0.482 | 0.618 | 0.377 | 1.012 |
| PNMT rs876493 | AA/AG vs GG | 0.071 | −0.531 | 0.588 | 0.331 | 1.046 |
| Age_at_onset | | 0.069 | 0.028 | 1.029 | 0.998 | 1.061 |

TABLE 3B-continued

Regression Analysis

| Variable name | Genotype/Variable level | Sig. | B | OR | I.C. 95% for OR | |
| --- | --- | --- | --- | --- | --- | --- |
| | | | | | Lower bound | Upper bound |
| gender | 0 = female vs 1 = male | 0.01 | 0.743 | 2.102 | 1.194 | 3.703 |
| Onsettype_cod | 0 = relapsing vs 1 = progressive | 0.006 | 1.71 | 5.529 | 1.616 | 18.917 |
| NOS2A rs1137933 | GG vs AG/AA | 0.018 | −0.593 | 0.553 | 0.339 | 0.901 |
| PITPNC1 rs1318 | AA vs AG/GG | 0.026 | −0.561 | 0.571 | 0.349 | 0.934 |
| IL2 rs2069763 | GG vs GT/TT | 0.009 | −0.709 | 0.492 | 0.288 | 0.839 |
| CCL5 rs2107538 | CC vs CT/TT | 0.031 | 0.606 | 1.832 | 1.058 | 3.173 |

The model obtained from the analysis of the 700 MS patients is showed in Table 3C. The model includes the same variables that the obtained from the analysis of 605 MS patients (Table 3) and from the analysis of the exploratory cohort or 595 MS patients (Table 3B).

TABLE 3C

Regression Analysis

| Variable name | Genotype/Variable level | Sig. | B | OR | I.C. 95% for OR | |
| --- | --- | --- | --- | --- | --- | --- |
| | | | | | Lower bound | Upper bound |
| IL1RN 2073 Intron2 C/T (rs423904) | CC vs CT/TT | .084 | −.404 | .668 | .422 | 1.056 |
| PNMT rs876493 | AA/AG vs GG | .053 | −.533 | .587 | .342 | 1.006 |
| Age_at_onset | | .015 | .036 | 1.036 | 1.007 | 1.066 |
| gender | 0 = female vs 1 = male | .017 | .634 | 1.884 | 1.119 | 3.173 |
| Onsettype_cod | 0 = relapsing vs 1 = progressive | .005 | 1.758 | 5.801 | 1.714 | 19.638 |
| NOS2A rs1137933 | GG vs AG/AA | .005 | −.649 | .522 | .331 | .824 |
| PITPNC1 rs1318 | AA vs AG/GG | .025 | −.527 | .590 | .373 | .935 |
| IL2 rs2069763 | GG vs GT/TT | .001 | −.818 | .441 | .267 | .730 |
| CCL5 rs2107538 | CC vs CT/TT | .015 | .643 | 1.902 | 1.132 | 3.196 |

Figure 7:
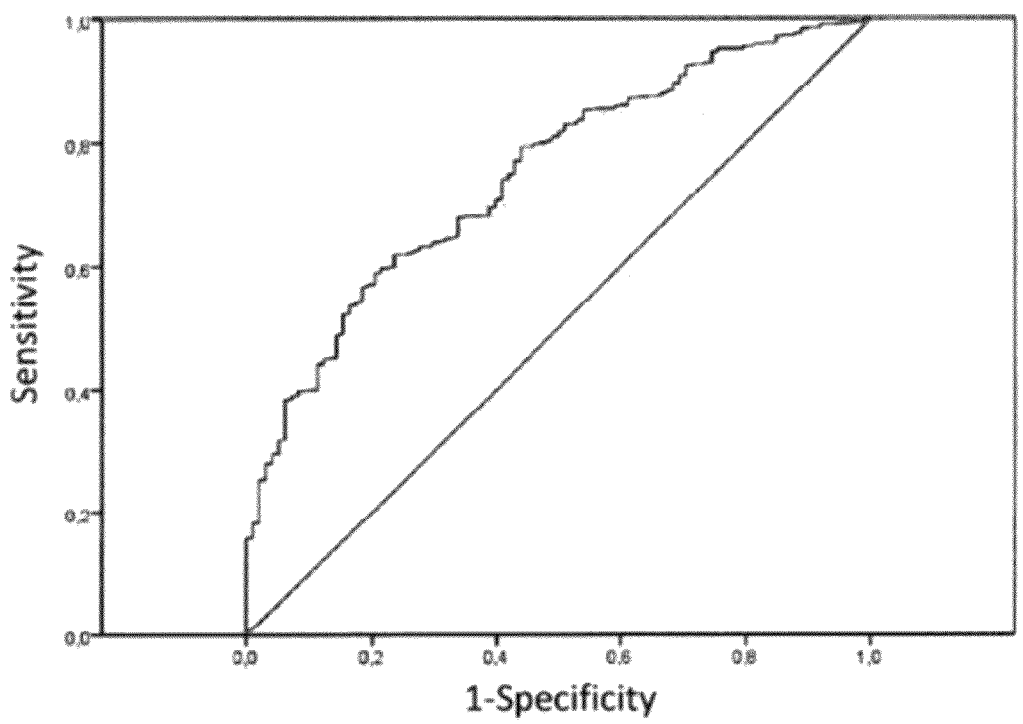
FIG. 7 is a graph showing a ROC (receiver operating characteristic) curve obtained for the model MSSS<2.5 versus≥2.5, showing the relationship between sensitivity (y-axis) and percentage (x-axis), as further described in Table 3C.

The ROC curve area obtained for the model MSSS≥2.5 vs MSSS<2.5 analysing the 700 MS patients is 0.749 (95% CI 0.700-0.797) (FIG. 7). A specificity of 95% with a sensitivity of 32% is the cut-off for this model. The model shows a positive likelihood ratio (LR+) value of 6.2.

Example 2

Identification of SNPs Associated with T2 Brain Lesions

Figure 2:
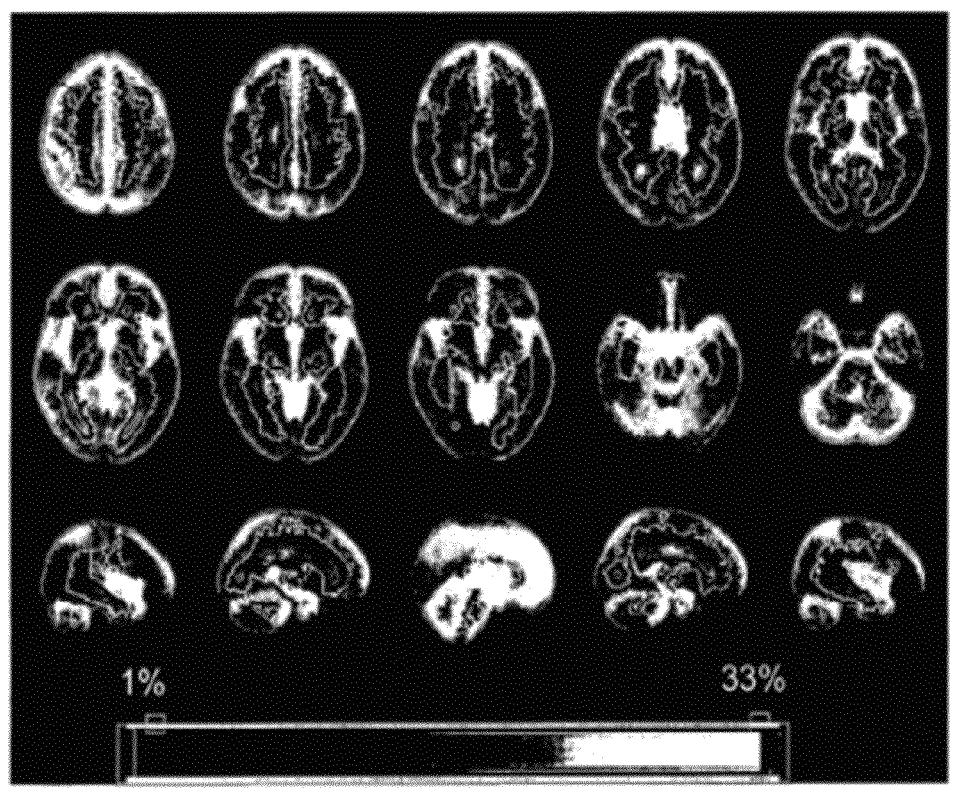
FIG. 2 depicts MRI data maps showing mean lesion frequency map of the patient sample (n=208). Lesion frequency across the patient sample is shown for every voxel on axial and sagittal slices. The colour bar indicates lesion frequency; voxels with a lesion frequency<1% are not shown; peak frequency was 32%.

In order to determine whether certain SNPs are associated with increasing size and distribution of T2 brain lesions, analysis was performed on a group of 208 MS patients with MRI data collected. The MRI data show spatial distribution of T2 brain lesions. FIG. 2 shows lesion frequency across the patient sample.

Figure 3:
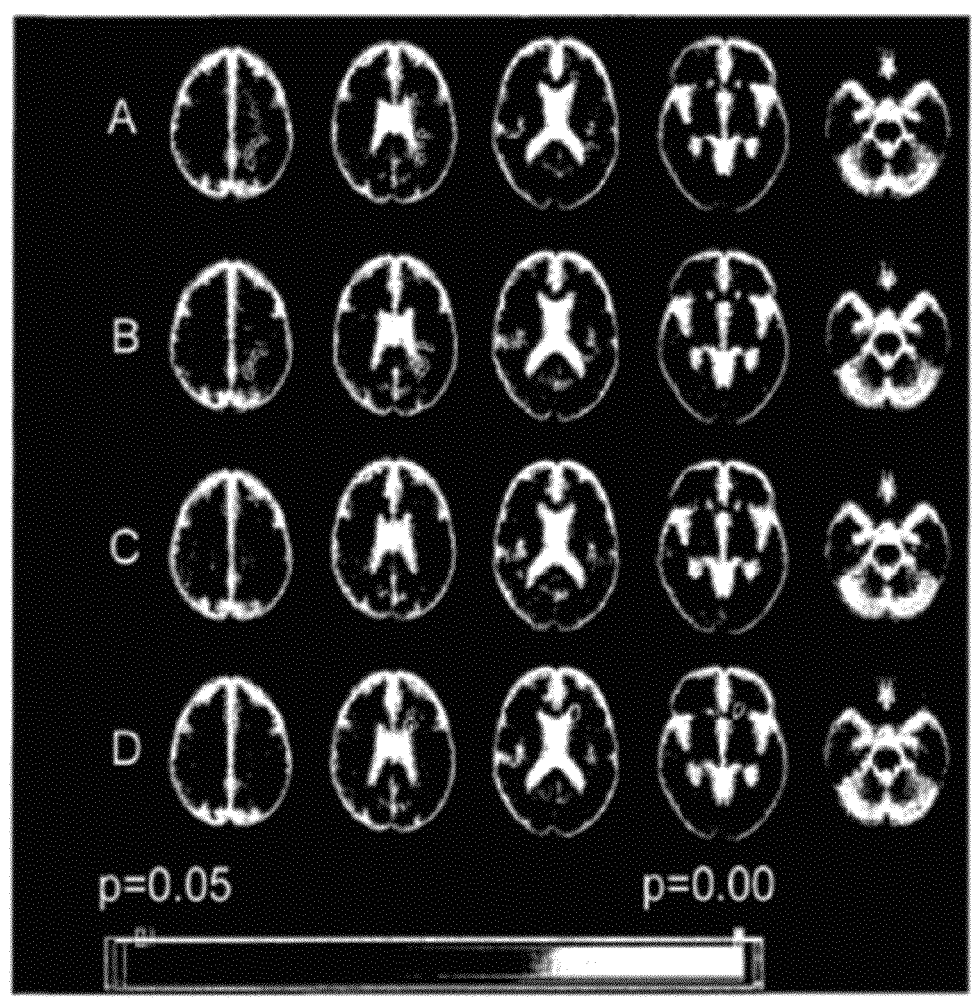
FIG. 3 depicts MRI data maps showing clusterwise (t=2) associations of lesion presence with genotype, on a background of the common brain image. The cluster colour bar indicates clusterwise p-value, with the range indicated by the colour bar; only clusters with p<0.05 are shown. A: rs2213584 (HLA-DRA gene); B: rs2227139 (HLA-DRA gene); C: rs2076530 (BTNL2 gene); D: rs876493 (PNMT gene).

FIG. 3 shows maps of clusterwise (t=2) associations of lesion presence with genotype, on a background of the common brain image. The cluster colour bar indicates clusterwise p-value, with the range indicated by the colour bar; only clusters with p<0.05 are shown. These data have been correlated to genotype data. The results show significant associations for four SNPs to brain lesions. A: rs2213584 (HLA-DRA gene); B: rs2227139 (HLA-DRA gene); C: rs2076530 (BTNL2 gene); D: rs876493 (PNMT gene).

Example 2A

Identification of SNPs Associated with T2 Brain Lesions

Further investigation was carried out essentially as described in Example 2. Additionally, lesions were manually outlined on Magnetic Resonance Imaging scans and binary lesion masks were produced and registered to a common space. Using Randomise software, the lesion masks were related to genotype using a voxelwise nonparametric General Linear Model approach, followed by clusterwise analysis. The results show significant associations for eight SNPs to brain lesions: rs9808753 (IFNGR2 gene), rs2074897 (NDUFS7 gene), rs762550 (CRYAB gene), rs2076530 (BTNL2 gene), rs2234978 (FAS gene), rs3781202 (FAS gene), rs2107538 (CCL5 gene), rs659366 (UCP2 gene).

Example 3

Identification of SNPs Associated with MS Severity Phenotypes

Patient Characteristics:

One hundred and fifty patients were included in the analysis. The patient group reflects a representative MS population, with approximately 35% men and 20% primary progressive MS patients (see Table 4). The majority of patients (132/150) demonstrated abnormalities on the spinal cord MRI scan, while all patients had abnormalities on the brain MRI scan.

TABLE 4

Patient characteristics

|  | All | RR | SP | PP |
|---|---|---|---|---|
| Total n | 150 | 88 | 32 | 30 |
| Gender (n; % M) | 55 (36.7%) | 26 (29.5%) | 17 (53.1%) | 12 (40%) |
| Age at MRI (mean) | 41.4 | 36.1 | 46.5 | 51.2 |
| Disease duration mean (range) | 7.1 (0.0-33.0) | 4.36 (0.0-32.0) | 12.8 (2.0-33.0) | 9.2 (0.0-28.0) |
| EDSS (median) | 3.5 | 2.0 | 5.5 | 4.0 |
| T2 lesionload (ml) (mean) | 7.7 | 4.9 | 16.2 | 7.0 |
| Number of focal lesions in the spinal cord (mean) | 3.4 | 3.3 | 4.5 | 2.8 |
| Percentage of patients with diffuse abnormalities (%) | 13.3 | 10.2 | 18.8 | 16.7 |

Genotyping:

In total 80 SNPs in 44 genes were selected on the MSchip. Twelve SNPs were excluded from further analysis: five were monomorphic and seven SNPs had a minor allele frequency below five percent (see Table). Hardy Weinberg equilibrium was calculated for all SNPs. Values are noted in table 5.

TABLE 5

Results analysis of the correlation SNPs and MRI parameters.

| Clinical/MRI parameter correlated with SNPs: | Rs-number SNP | Gene | Uncorrected p-value Kruskal Wallis test: | FDR-corrected p-value |
|---|---|---|---|---|
| Number of focal lesion in the spinal cord | rs3135388 | MHC II | 0.00082 | 0.03 |
|  | rs2395182* | MHC II | 0.00107 | 0.03 |
|  | rs2239802* | MHC II | 0.00122 | 0.03 |
|  | rs2227139** | MHC II | 0.00169 | 0.03 |
|  | rs2213584** | MHC II | 0.00330 | 0.05 |
|  | rs3087456 | MHC II TransActivator | 0.00900 | 0.10 |
| T2 lesion load in the brain | rs2107538 | CCL5 | 0.001 | 0.07 |

* and ** LD values still need to be calculated.

Correlation Between Clinical Parameters and MRI Features:

The EDSS showed a mild correlation with the number of focal lesions in the spinal cord (p=0.043, r=0.165, Pearson correlation), with the number of segments involved (p=0.006, r=0.224, Pearson correlation) and a moderate correlation with T2 lesion load in the brain (p<0.001, r=0.395). A weak correlation was present between the number of focal spinal cord lesions and T2 lesion load in the brain (p=0.063, r=0.152).

Disease duration was found to be related to number of segments of the spinal cord involved (p=0.017, r=0.195).

The T2 lesion load in the brain was closely related to the PASAT score (p=0.000, r=−0.581) and 9 Hole Peg Test of the dominant hand (p=0.001, r=0.306).

Correlation Between Lesion Load in the Brain and Genotypes:

In the univariate analysis on T2 lesion load in the brain and the MS-chip, the only 'trend' correlation was rs2107538 (CCL5) (see Table 5).

Figure 4:
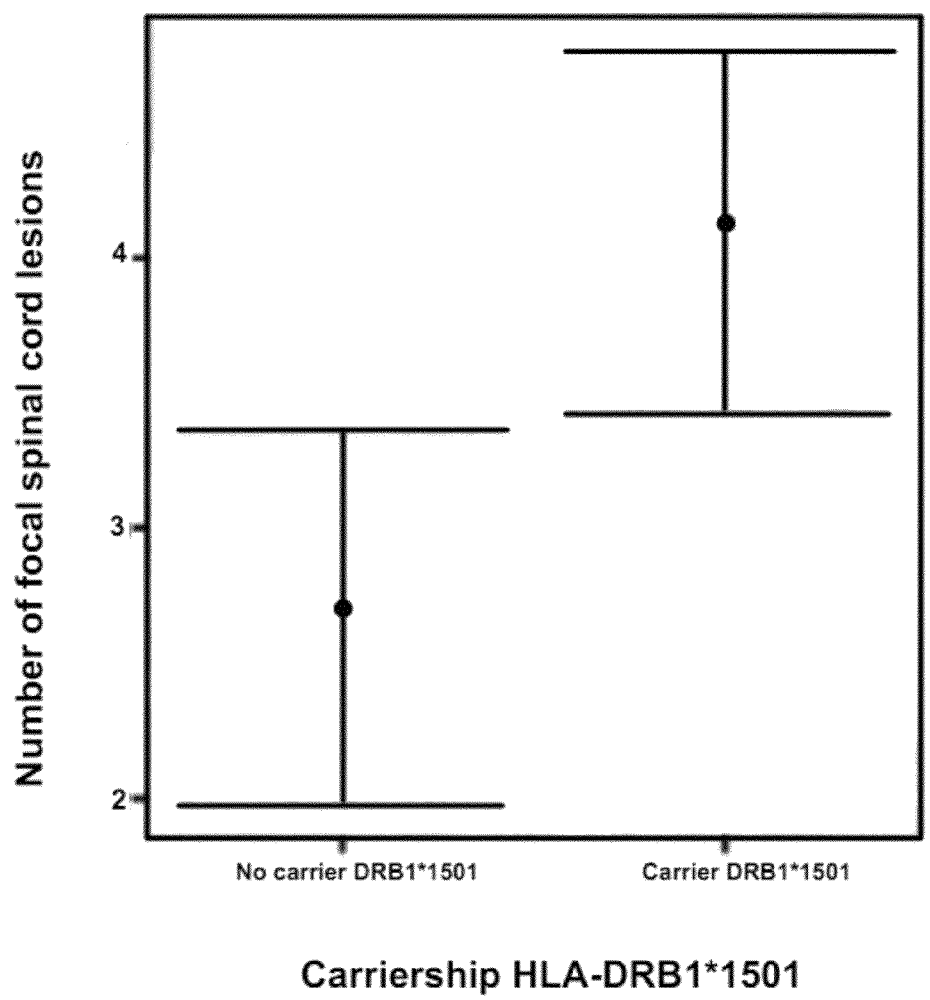
FIG. 4 is a graph showing the mean number of focal spinal cord lesions in patients who carry HLA-DRB1*1501 (measured as presence of A-allele of rs3135388). Difference between carriers and non-carriers p<0.001, Maim Whitney U test. Error bars show 95% confidence interval of mean.

Correlation Between Spinal Cord Abnormalities and Genotypes:

Several HLA SNPs were found to be related to the number of focal spinal cord abnormalities (see Table 5). The most significant is SNP rs3135388. Carriership of the A-allele (surrogate marker for HLA-DRB1*1501) was associated with a significantly higher number of lesions in the spinal cord (FIG. 4).

When corrected for multiple testing, five SNPs within the MHC region (rs3135388, rs2395182, rs2239802, rs2227139 and rs2213584), remained significant and one SNP within the MHC-2TA gene (Major Histocompatibility Complex Class II Transactivator) showed a trend towards a correlation. The five HLA SNPs are in high linkage disequilibrium.

A linear model has been developed using multiple linear regression to predict the number of focal lesions in the spinal cord. This method uses three of these SNPs rs3135388, rs3087456, and rs2227139. A model including the combination of these three SNPs improves the use of one single SNP (rs3135388) for prediction of number of focal lesions in the spinal cord. Corrected Rsquared for model using only one SNP=0.064. Corrected Rsquared for model using combination of three SNPs=0.112. The combination of these three SNPs or any SNP in linkage disequilibrium with any of these three SNPs improves prediction of number of focal lesions in the spinal cord over the use of one single SNP.

No interactions between the SNPs and the clinical variables were present. No association was observed between the presence of diffuse abnormalities and the evaluated SNPs.

Example 4

Identification of Additional SNPs Associated with MRI Parameters: Number of Focal Lesion in the Spinal Cord, T2 Lesion Load in the Brain and Presence of Diffuse Abnormalities In order to determine whether certain additional SNPs are associated with MRI parameters, a similar analysis to Example 3 was performed using different SNPs on one hundred and fifty patients. Results of the correlation of additional SNPs and MRI parameters are shown in table 5A.

In our study cohort of 150 MS patients with MRI data, MRI data are significantly correlated with MS severity given by MSSS (p=0.023). It can thus be assumed that identification of SNPs associated with MRI parameters allows inferring MS severity.

TABLE 5A

Results of analysis of the correlation of additional SNPs and MRI parameters.

| Clinical/MRI parameter correlated with SNPs: | Rs-number SNP | Gene | Uncorrected p-value Kruskal Wallis test: |
|---|---|---|---|
| Number of focal lesion in | rs10492972 | KIF1B | 0.0063 |
|  | rs12202350 | IGF2R | 0.005 |

TABLE 5A-continued

Results of analysis of the correlation of additional SNPs and MRI parameters.

| Clinical/MRI parameter correlated with SNPs: | Rs-number SNP | Gene | Uncorrected p-value Kruskal Wallis test: |
|---|---|---|---|
| the spinal cord T2 lesion load in the brain | rs8049651 | GRIN2A | 0.0023 |
|  | rs8702 | KLC1 | 5.00E−04 |
|  | rs987107 | IL7R | 0.0091 |
|  | rs12861247 | STS | 0.005 |
|  | rs2074897 | NDUFS7 | 0.006 |
|  | rs7995215 | GPC6 | 0.006 |
| Presence of diffuse abnormalities | rs1350666 | EREG | 0.008 |
|  | rs3808585 | ADRA1A | 0.003 |
|  | rs4128767 | IL16 | 0.006 |
|  | rs6457594 | MHC II | 0.005 |
|  | rs7208257 | ARRB2 | 0.006 |
|  | rs7956189 | NTF3 | 0.008 |

TABLE 6

SNPs included in the analyses; HWE = Hardy-Weinberg Equilibrium in our sample; MAF = minor allele frequency in our sample

| Gene | rs-nr | Chromosome | Polymorphism | HWE* | MAF |
|---|---|---|---|---|---|
| ADAMTS14 | rs4747075 | 10q22 | A/G | 7.74* | 0.30 |
| ADAMTS14 | rs7081273 | 10q22 | C/G | 1.2 | 0.34 |
| ADAMTS14 | rs4746060 | 10q22 | C/T | 1.05 | 0.08 |
| Apo I/Fas | rs1800682 | 10q23 | C/T | 0.02 | 0.47 |
| Apo I/Fas | rs3781202 | 10q23 | C/T | 7.41* | 0.40 |
| Apo I/Fas | rs2234978 | 10q23 | C/T | 0.43 | 0.31 |
| BTNL2 | rs2076530 | 6p21.3 | A/G | 29.78* | 0.26 |
| CACNG4 | rs4790896 | 17q24 | A/G | 0.36 | 0.41 |
| CCR5 | rs333 | 3p21 | −/+ | 0.02 | 0.11 |
| CD24 | rs8734 | 6q21 | C | NA | 0.00** |
| CNTF | rs1800169 | 11q12 | A/G | 0.80 | 0.12 |
| CRYAB | rs14133 | 11q21-q23 | C/G | 0.08 | 0.27 |
| CRYAB | rs762550 | 11q21-q23 | A/G | 0.14 | 0.42 |
| CRYAB | rs2234702 | 11q21-q23 | C | NA | 0.00** |
| CTLA4 | rs231775 | 2q33 | A/G | 1.03 | 0.37 |
| CTLA4 | rs5742909 | 2q33 | C/T | 0.45 | 0.09 |
| EBF | rs1368297 | 5q34 | A/T | 0.06 | 0.38 |
| GABBRA1 | rs1805057 | 6p22 | C | NA | 0.00** |
| HELZ | rs2363846 | 17q24 | C/T | 2.23 | 0.48 |
| HLA | rs2395166 | 6p21.3 | C/T | 3.46 | 0.47 |
| HLA | rs2213584 | 6p21.3 | A/G | 3.61 | 0.40 |
| HLA | rs2227139 | 6p21.3 | C/T | 2.89 | 0.40 |
| HLA | rs3135388 | 6p21.3 | A/G | 0.97 | 0.33 |
| HLA | rs9268458 | 6p21.3 | A/C | 1.29 | 0.20 |
| HLA | rs6457594 | 6p21.3 | A/G | 35.65* | 0.40 |
| HLA-DRA | rs2395182 | 6p21.3 | G/T | 1.04 | 0.38 |
| HLA-DRA | rs2239802 | 6p21.3 | C/G | 1.34 | 0.38 |
| IFNAR1 | rs2257167 | 21q22 | C/G | 0.00 | 0.08 |
| IFNGR2 | rs9808753 | 21q22 | A/G | 0.00 | 0.14 |
| IKBL | rs3130062 | 6p21.3. | C/T | 1.14 | 0.18 |
| IL-10 | rs1800896 | 1q32 | A/G | 0.56 | 0.46 |
| IL1B | rs1799916 | 2q14 | A | NA | 0.00** |
| IL1B | rs1143627 | 2q14 | A/G | 5.32* | 0.34 |
| IL-1B | rs1143634 | 2q14 | C/T | 0.01 | 0.23 |
| IL-1RN | rs419598 | 2q12-q14 | C/T | 0.53 | 0.31 |
| IL-1RN | 2073 Intron2 C/T (rs423904) | 2q12-q14 | C/T | 0.72 | 0.30 |
| IL-2 | rs2069763 | 4q26 | G/T | 0.75 | 0.36 |
| IL-2 | rs2069762 | 4q26 | G/T | 0.31 | 0.27 |
| IL-4R | rs1801275 | 16p12 | A/G | 0.37 | 0.20 |
| IL7R | rs11567685 | 5p13 | C/T | 0.68 | 0.25 |
| IL7R | rs7718919 | 5p13 | G/T | 0.22 | 0.13 |
| IL7R | rs11567686 | 5p13 | A/G | 1.44 | 0.34 |
| MC1R | rs1805009 | 16q24 | C/G | 0.02 | 0.01** |
| MC1R | rs1805006 | 16q24 | A/C | 0.00 | 0.00** |
| MEFV | rs28940577 | 16p13.3 | A | NA | 0.00** |
| MGC33887 | rs987931 | 17q24 | G/T | 0.39 | 0.32 |
| MHC2TA | rs3087456 | 16p13 | A/G | 0.13 | 0.26 |
| MOG | rs3130250 | 6p22 | A/G | 0.01 | 0.19 |
| MOG | rs3130253 | 6p22 | A/G | 0.80 | 0.12 |
| NDUFA7 | rs2288414 | 19p13.2 | C/G | 7.90* | 0.03** |
| NDUFA7 | rs561 | 19p13.2 | A/G | 0.04 | 0.21 |
| NDUFS5 | rs2889683 | 1p34.2 | C/T | 2.63 | 0.31 |
| NDUFS5 | rs6981 | 1p34.2 | A/G | 105.96* | 0.04** |
| NDUFS7 | rs2074897 | 19p13.3 | A/G | 6.21* | 0.47 |
| NOS2A | rs1137933 | 17q11.2 | A/G | 0.49 | 0.25 |
| NOS2A | rs2779248 | 17q11.2 | C/T | 0.00 | 0.39 |
| NOTCH4 | rs367398 | 6p21.3 | A/G | 0 | 0.16 |
| PD-1 | rs11568821 | 2q37 | G/A | 6.24* | 0.11 |
| PITPNC1 | rs1318 | 17q24 | A/G | 0.01 | 0.21 |
| PITPNC1 | rs2365403 | 17q24 | C/G | 0.55 | 0.18 |
| PNMT | rs876493 | 17q11-q23 | A/G | 0.70 | 0.39 |
| PRKCA | rs7220007 | 17q24 | A/G | 0.10 | 0.49 |
| PRKCA | rs887797 | 17q24 | C/T | 0.50 | 0.30 |
| PRKCA | rs2078153 | 17q24 | C/G | 0.91 | 0.23 |
| PRKCA | rs3890137 | 17q24 | A/G | 0.44 | 0.37 |
| PTPN22 | rs2476601 | 1p13 | A/G | 2.29 | 0.11 |
| PTPRC | rs17612648 | 1q31 | C/G | 0.11 | 0.03** |
| PTPRC | rs4915154 | 1q31 | A/G | 0.00 | 0.00** |
| CCL5 | rs2280788 | 17q11.2-q12 | C/G | 0.06 | 0.02** |
| CCL5 | rs2107538 | 17q11.2-q12 | C/T | 0.00 | 0.18 |
| Spp1 | rs1126616 | 4q21 | C/T | 0.01 | 0.23 |
| Spp1 | rs1126772 | 4q21 | A/G | 0.23 | 0.18 |
| Spp1 | rs2853744 | 4q21 | G/T | 0.48 | 0.05 |
| Spp1 | rs9138 | 4q21 | A/C | 0.03 | 0.24 |
| Spp1 | rs4754 | 4q21 | C/T | 0.07 | 0.24 |
| TNF-alpha | rs1800629 | 6p21.3 | A/G | 2.02 | 0.17 |
| TRAIL | rs1131568 | 3q26 | C/T | 1.53 | 0.32 |
| UCP2 | rs659366 | 11q13 | C/T | 0.15 | 0.37 |
| VDR | rs1544410 | 12q13 | A/G | 1.27 | 0.48 |
| VDR | rs731236 | 12q13 | A/G | 0.39 | 0.48 |

*ChiSquare value. A value >3.84 indicates deviation from Hardy-Weinberg Equilibrium (p < 0.05).
**Excluded due to minor allele frequency <0.05)

TABLE 6A

Additional SNPs included in the analyses

| Gene | rs-nr |
|---|---|
| KIF1B | rs10492972 |
| IGF2R | rs12202350 |
| GRIN2A | rs8049651 |
| KLC1 | rs8702 |
| IL7R | rs987107 |
| STS | rs12861247 |
| GPC6 | rs7995215 |
| EREG | rs1350666 |
| ADRA1A | rs3808585 |
| IL16 | rs4128767 |
| ARRB2 | rs7208257 |
| NTF3 | rs7956189 |
| IL12A | rs4680534 |
| SLC6A4 | rs1042173 |

TABLE 7

Examples of Probes Used in SNP Analysis

| Gene Symbol | Gene Name | rs ID | SNP | Oligonucleotide sequence (5' > 3') | SEQ ID NO: |
|---|---|---|---|---|---|
| EBF1 | Early B-cell Factor 1 | rs1368297 | intron 7 (271,440) A/T | TAAAGTTAGTC A GTTCTATGCTT | 1 |
| | | | | TAAAGTTAGTC T GTTCTATGCTT | 2 |
| | | | | AAGCATAGAAC T GACTAACTTTA | 3 |
| | | | | AAGCATAGAAC A GACTAACTTTA | 4 |
| RANTES/ CCL5 | chemokine (C-C motif) ligand 5 | rs2280788 | -28C/G | GGGATGCCCCT C AACTGGCCCTA | 5 |
| | | | | GGGATGCCCCT G AACTGGCCCTA | 6 |
| | | | | TAGGGCCAGTT G AGGGGCATCCC | 7 |
| | | | | TAGGGCCAGTT C AGGGGCATCCC | 8 |
| RANTES/ CCL5 | chemokine (C-C motif) ligand 5 | rs2107538 | -403G/A | AGGGAAAGGAG G TAAGATCTGTA | 9 |
| | | | | AGGGAAAGGAG A TAAGATCTGTA | 10 |
| | | | | TACAGATCTTA C CTCCTTTCCCT | 11 |
| | | | | TACAGATCTTA T CTCCTTTCCCT | 12 |
| TGFB1 | transforming growth factor, beta 1 | rs17851976 | L10P G869A | GTAGCAGCAGC G GCAGCAGCCGC | 13 |
| | | | | GTAGCAGCAGC A GCAGCAGCCGC | 14 |
| | | | | GCGGCTGCTGC C GCTGCTGCTAC | 15 |
| | | | | GCGGCTGCTGC T GCTGCTGCTAC | 16 |
| UPC2 | uncoupling protein 2 | rs659366 | -866G/A | GGGGTAACTGA C GCGTGAACAGC | 17 |
| | | | | GGGGTAACTGA T GCGTGAACAGC | 18 |
| | | | | GCTGTTCACGC G TCAGTTACCCC | 19 |
| | | | | GCTGTTCACGC A TCAGTTACCCC | 20 |
| IKBL | inhibitory kappaB-like | rs3130062 | C224R; 738T/C | CAGAGGGATCC C GTCGACCCCCA | 21 |
| | | | | CAGAGGGATCC T GTCGACCCCCA | 22 |
| | | | | TGGGGGTCGAC G GGATCCCTCTG | 23 |
| | | | | TGGGGGTCGAC A GGATCCCTCTG | 24 |
| Apo I/Fas (CD 95) | tumor necrosis factor receptor superfamily | rs1800682 | -671A/G | GTCCATTCCAG A AACGTCTGTGA | 25 |
| | | | | GTCCATTCCAG G AACGTCTGTGA | 26 |
| | | | | TCACAGACGTT T CTGGAATGGAC | 27 |
| | | | | TCACAGACGTT C CTGGAATGGAC | 28 |
| Apo I/Fas (CD 95) | tumor necrosis factor receptor superfamily | rs3781202 | A/T (735)G/C intron 4 | ATAAAATTTTC C TAGCAAATAAA | 29 |
| | | | | ATAAAATTTTC T TAGCAAATAAA | 30 |
| | | | | TTTATTTGCTA G GAAAATTTTAT | 31 |
| | | | | TTTATTTGCTA A GAAAATTTTAT | 32 |
| IL2 | interleukin 2 | rs2069763 | 114G/T | GAGCATTTACT G CTGGATTTACA | 33 |
| | | | | GAGCATTTACT T CTGGATTTACA | 34 |
| | | | | TGTAAATCCAG C AGTAAATGCTC | 35 |
| | | | | TGTAAATCCAG A AGTAAATGCTC | 36 |
| IL2 | interleukin 2 | rs2069762 | -385A/C | TTTTCTTTGTC A TAAAACTACAC | 37 |
| | | | | TTTTCTTTGTC C TAAAACTACAC | 38 |
| | | | | TTCAGTGTAGTTTTA T GACAAAGAAAATTTT | 39 |
| | | | | TTCAGTGTAGTTTTA G GACAAAGAAAATTTT | 40 |
| IL10 | interleukin 10 | rs1800896 | -1082G/A | GCTTCTTTGGGAAGGGGAAGTAGGG | 41 |
| | | | | GCTTCTTTGGGAGGGGGAAGTAGGG | 42 |
| | | | | CCCTACTTCCCCTTCCCAAAGAAGC | 43 |
| | | | | CCCTACTTCCCCCTCCCAAAGAAGC | 44 |
| IL4R | interleukin 4 receptor | rs1801275 | Q551R | CAGTGGCTATC G GGAGTTTGTAC | 45 |
| | | | | CAGTGGCTATC A GGAGTTTGTAC | 46 |
| | | | | TACAAACTCC C GATAGCCACT | 47 |
| | | | | TACAAACTCC T GATAGCCACT | 48 |
| PTPRC | protein tyrosine phosphatase, receptor type, C | rs17612648 | C77G | GCATTCTCACC C GCAAGCACCTT | 49 |
| | | | | GCATTCTCACC G GCAAGCACCTT | 50 |
| | | | | AAGGTGCTTGC G GGTGAGAATGC | 51 |
| | | | | AAGGTGCTTGC C GGTGAGAATGC | 52 |
| PTPRC | protein tyrosine phosphatase, receptor type, C | rs4915154 | A138G | TCACAGCGAAC G CCTCAGGTCTG | 53 |
| | | | | TCACAGCGAAC A CCTCAGGTCTG | 54 |
| | | | | CAGACCTGAGG C GTTCGCTGTGA | 55 |
| | | | | CAGACCTGAGG T GTTCGCTGTGA | 56 |
| PD-1/PDCD1 | programmed cell death 1 | rs11568821 | G7146A | AGCCCACCTGC G GTCTCCGGGGG | 57 |
| | | | | AGCCCACCTGC A GTCTCCGGGGG | 58 |
| | | | | CCCCCGGAGAC C GCAGGTGGGCT | 59 |
| | | | | CCCCCGGAGAC T GCAGGTGGGCT | 60 |
| CRYAB | crystallin, alpha B | rs14133 | -C249G | TGAAACAAGAC C ATGACAAGTCA | 61 |
| | | | | TGAAACAAGAC G ATGACAAGTCA | 62 |
| | | | | TGACTTGTCAT G GTCTTGTTTCA | 63 |
| | | | | TGACTTGTCAT C GTCTTGTTTCA | 64 |
| CRYAB | crystallin, alpha B | rs762550 | -A652G | GAGCCACATAGAACGAAAGATGC | 65 |
| | | | | GAGCCACATAGGACGAAAGATGC | 66 |
| | | | | GCATCTTTCGTTCTATGTGGCTC | 67 |
| | | | | CATCTTTCGT C CTATGTGGCT | 68 |
| CRYAB | crystallin, alpha B | rs2234702 | -C650G | GCCACATAGAA C GAAAGATGCAA | 69 |
| | | | | GCCACATAGAA G GAAAGATGCAA | 70 |
| | | | | TTGCATCTTTC G TTCTATGTGGC | 71 |
| | | | | TTGCATCTTTC C TTCTATGTGGC | 72 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| NDUFS5 | NADH dehydrogenase (ubiquinone) Fe-S protein 5 | rs2889683 | -5649T/C | ACAACAGCAGA A ATAATAATCAA | 73 |
| | | | | ACAACAGCAGA G ATAATAATCAA | 74 |
| | | | | TTGATTATTAT T TCTGCTGTTGT | 75 |
| | | | | TTGATTATTAT C TCTGCTGTTGT | 76 |
| NDUFS5 | NADH dehydrogenase (ubiquinone) Fe-S protein 5 | rs6981 | 3' UTR 5789 A/G | CAGCTGCTGAT A TCTGGAGGCTG | 77 |
| | | | | CAGCTGCTGAT G TCTGGAGGCTG | 78 |
| | | | | CAGCCTCCAGA T ATCAGCAGCTG | 79 |
| | | | | CAGCCTCCAGA C ATCAGCAGCTG | 80 |
| NDUFS7 | NADH dehydrogenase (ubiquinone) Fe-S protein 7 | rs2074897 | intron 6 (6 + 71) A/G | GCCCTGATGGC A CTTATCAAAAG | 81 |
| | | | | GCCCTGATGGC G CTTATCAAAAG | 82 |
| | | | | CTTTTGATAAG T GCCATCAGGGC | 83 |
| | | | | CTTTTGATAAG C GCCATCAGGGC | 84 |
| NDUFA7 | NADH dehydrogenase (ubiquinone) 1 alpha | rs2288414 | intron 2 (2 + 89) C/G | ATGTCAGCCCT C CGTTTCAGGGG | 85 |
| | | | | ATGTCAGCCCT G CGTTTCAGGGG | 86 |
| | | | | CCCCTGAAACG G AGGGCTGACAT | 87 |
| | | | | CCCCTGAAACG C AGGGCTGACAT | 88 |
| NDUFA7 | NADH dehydrogenase (ubiquinone) 1 alpha | rs561 | 9825 A/G | CCACCTCTTTAT A GGAGGAGCTGGA | 89 |
| | | | | CCACCTCTTTAT G GGAGGAGCTGGA | 90 |
| | | | | CCAGCTCCTCC T ATAAAGAGGTG | 91 |
| | | | | CCAGCTCCTCC C ATAAAGAGGTG | 92 |
| ADAMTS14 | ADAM metallopeptidase with thrombospondin type 1 | rs4747075 | intron 2 16860 A/G | CCCAGATGATG A CATTCGCCTTC | 93 |
| | | | | CCCAGATGATG G CATTCGCCTTC | 94 |
| | | | | GAAGGCGAATG T CATCATCTGGG | 95 |
| | | | | GAAGGCGAATG C CATCATCTGGG | 96 |
| ADAMTS14 | ADAM metallopeptidase with thrombospondin type 1 | rs7081273 | intron 2 24479 C/G | CATTTGGCAAA C GTAGGCTGGTC | 97 |
| | | | | CATTTGGCAAA G GTAGGCTGGTC | 98 |
| | | | | GACCAGCCTAC G TTTGCCAAATG | 99 |
| | | | | GACCAGCCTAC C TTTGCCAAATG | 100 |
| ADAMTS14 | ADAM metallopeptidase with thrombospondin type 1 | rs4746060 | intron 4 44225 C/T | GCACATCTATA C TGGGTCATCTT | 101 |
| | | | | GCACATCTATA T TGGGTCATCTT | 102 |
| | | | | AAGATGACCCA G TATAGATGTGC | 103 |
| | | | | AAGATGACCCA A TATAGATGTGC | 104 |
| NFKBIA | nuclear factor of kappa light polypeptide gene enhancer in B-cells inhibitor, alpha | rs11569591 | -708ins8 | GCGTGGGGGGG T GGGGGCGAAGC | 105 |
| | | | | GGGTGGGGGGG A GGGGGCGAAGC | 106 |
| | | | | GCTTCGCCCCC A CCCCCCCACGC | 107 |
| | | | | GCTTCGCCCCC T CCCCCCCACCC | 108 |
| NFKBIA | nuclear factor of kappa light polypeptide gene enhancer in B-cells inhibitor, alpha | rs11569591 | -708ins8 | CGTGGGGGGG T GGGGGCGAAG | 109 |
| | | | | GGTGGGGGGG A GGGGGCGAAG | 110 |
| | | | | CTTCGCCCCC A CCCCCCCACG | 111 |
| | | | | CTTCGCCCCC T CCCCCCCACC | 112 |
| NFKBIA | nuclear factor of kappa light polypeptide gene enhancer in B-cells inhibitor, alpha | rs11569591 | -708ins8 | TGCGTGGGGGGG T GGGGGCGAAGCT | 113 |
| | | | | GGGGTGGGGGGG A GGGGGCGAAGCT | 114 |
| | | | | AGCTTCGCCCCC A CCCCCCCACGCA | 115 |
| | | | | AGCTTCGCCCCC T CCCCCCCACCCC | 116 |
| SPP1 | secreted phosphoprotein 1 | rs28357094 | -66[G/T] | GACACAATCTC G CCGCCTCCCTG | 117 |
| | | | | GACACAATCTC T CCGCCTCCCTG | 118 |
| | | | | CAGGGAGGCGG C GAGATTGTGTC | 119 |
| | | | | CAGGGAGGCGG A GAGATTGTGTC | 120 |
| HLA-DR*1501 | major histocompatibility complex, class II, DR | rs367398 | -25 A/G (NOTCH4) | CTCCAAGCCCC A GTCCCTGTCCC | 121 |
| | | | | CTCCAAGCCCC G GTCCCTGTCCC | 122 |
| | | | | GGGACAGGGAC T GGGGCTTGGAG | 123 |
| | | | | GGGACAGGGAC C GGGGCTTGGAG | 124 |
| HLA-DR*1501 | major histocompatibility complex, class II, DR | rs1800629 | -308G > A (TNF-alpha) | TGAGGGGCATG A GGACGGGGTTC | 125 |
| | | | | TGAGGGGCATG G GGACGGGGTTC | 126 |
| | | | | _AACCCCGTCC T CATGCCCCTC_ | 127 |
| | | | | _AACCCCGTCC C CATGCCCCTC_ | 128 |
| IL7R | interleukin 7 receptor | rs11567685 | -504T/C | GCATTTGCCTGCAGTCCTAGCTA | 129 |
| | | | | GCATTTGCCTGTAGTCCTAGCTA | 130 |
| | | | | TAGCTAGGACTGCAGGCAAATGC | 131 |
| | | | | TAGCTAGGACTACAGGCAAATGC | 132 |
| IL7R | interleukin 7 receptor | rs7718919 | -1085G/T | CACAAATGGGT G AGGCTGTATTC | 133 |
| | | | | CACAAATGGGT T AGGCTGTATTC | 134 |
| | | | | GAATACAGCCT C ACCCATTTGTG | 135 |
| | | | | GAATACAGCCT A ACCCATTTGTG | 136 |
| IL7R | interleukin 7 receptor | rs11567686 | -449A/G | CCTGGGAGGTG A AAATTGCAGTG | 137 |
| | | | | CCTGGGAGGTG G AAATTGCAGTG | 138 |
| | | | | CACTGCAATTT T CACCTCCCAGG | 139 |
| | | | | CACTGCAATTT C CACCTCCCAGG | 140 |
| IFNAR1 | interferon (alpha, beta and omega) receptor 1 | rs2257167 | V168L (G18417C) | ACATATAGCTTA C TTATCTGGAAAA | 141 |
| | | | | ACATATAGCTTA G TTATCTGGAAAA | 142 |
| | | | | TTTTCCAGATAA G TAAGCTATATGT | 143 |
| | | | | TTTTCCAGATAA C TAAGCTATATGT | 144 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| IFNAR2 | interferon (alpha, beta and omega) receptor 2 | rs7279064 | F10V (11876T > G) | ATGCCTTCATC G TCAGATCACTT | 145 |
| | | | | ATGCCTTCATC T TCAGATCACTT | 146 |
| | | | | AAGTGATCTGA C GATGAAGGCAT | 147 |
| | | | | AAGTGATCTGA A GATGAAGGCAT | 148 |
| IL1B | interleukin 1, beta proprotein | rs1799916 | -511 A/C | AAGAGAATCCC A GAGCAGCCTGT | 149 |
| | | | | AAGAGAATCCC C GAGCAGCCTGT | 150 |
| | | | | ACAGGCTGCTC T GGGATTCTCTT | 151 |
| | | | | ACAGGCTGCTC G GGGATTCTCTT | 152 |
| IFNGR2 | interferon gamma receptor 2 (interferon gamma transducer 1) | rs9808753 | Q64R | TGTTGTCTACC A AGTGCAGTTTA | 153 |
| | | | | TGTTGTCTACC G AGTGCAGTTTA | 154 |
| | | | | TAAACTGCACT T GGTAGACAACA | 155 |
| | | | | TAAACTGCACT C GGTAGACAACA | 156 |
| Apo I/Fas (CD 95) | tumor necrosis factor receptor superfamily | rs2234978 | E7(74) C > T | GAATCTCCAAC C TTAAATCCTGT | 157 |
| | | | | GAATCTCCAAC T TTAAATCCTGT | 158 |
| | | | | ACAGGATTAA G GTTGGAGATTC | 159 |
| | | | | ACAGGATTAA A GTTGGAGATTC | 160 |
| CD24 | CD24 antigen precursor | rs8734 | V57A (226T > C) | CACCACCAAGG T GGCTGGTGGTG | 161 |
| | | | | CACCACCAAGG C GGCTGGTGGTG | 162 |
| | | | | CACCACCAGCC A CCTTGGTGGTG | 163 |
| | | | | CACCACCAGCC G CCTTGGTGGTG | 164 |
| MEFV | Mediterranean fever protein | rs28940577 | M694V | GGGTGGTGATA A TGATGAAGGAA | 165 |
| | | | | GGGTGGTGATA G TGATGAAGGAA | 166 |
| | | | | TTCCTTCATCA T TATCACCACCC | 167 |
| | | | | TTCCTTCATCA C TATCACCACCC | 168 |
| CTLA4 | cytotoxic T-lymphocyte-associated antigen 4 | rs231775 | +49A/G | TGAACCTGGCT A CCAGGACCTGG | 169 |
| | | | | TGAACCTGGCT G CCAGGACCTGG | 170 |
| | | | | CCAGGTCCTGG T AGCCAGGTTCA | 171 |
| | | | | CCAGGTCCTGG C AGCCAGGTTCA | 172 |
| CNTF | ciliary neurotrophic factor | rs1800169 | intron 1 | CCTGTATCCTC A GCCAGGTGAAG | 173 |
| | | | | (2-7) A/G | CCTGTATCCTC G GCCAGGTGAAG | 174 |
| | | | | CTTCACCTGGC T GAGGATACAGG | 175 |
| | | | | CTTCACCTGGC C GAGGATACAGG | 176 |
| MHC2TA | class II, major histocompatibility complex, transactivator | rs3087456 | -168A/G | TTCAGAGGTGT A GGGAGGGCTTA | 177 |
| | | | | TTCAGAGGTGT G GGGAGGGCTTA | 178 |
| | | | | TAAGCCCTCCC T ACACCTCTGAA | 179 |
| | | | | TAAGCCCTCCC C ACACCTCTGAA | 180 |
| VDR | vitamin D receptor | rs1544410 | 33062 A/G Intron | GACAGGCCTGC A CATTCCCAATA | 181 |
| | | | | GACAGGCCTGC G CATTCCCAATA | 182 |
| | | | | ATTGGGAATG T GCAGGCCTG | 183 |
| | | | | TTGGGAATG C GCAGGCCTG | 184 |
| PRKCA | protein kinase C, alpha | rs7220007 | intron 3 264550 A/G | CCCCTGCTGGC A GATTGTTGCTA | 185 |
| | | | | CCCCTGCTGGC G GATTGTTGCTA | 186 |
| | | | | TAGCAACAATC T GCCAGCAGGGG | 187 |
| | | | | TAGCAACAATC C GCCAGCAGGGG | 188 |
| PRKCA | protein kinase C, alpha | rs887797 | intron 3 280475 C/T | GTCTTTTTAATA G CTGTAGACATCT | 189 |
| | | | | GTCTTTTTAATA A CTGTAGACATCT | 190 |
| | | | | GTCTTTTTAATA G CTGTAGACATCT | 191 |
| | | | | GTCTTTTTAATA A CTGTAGACATCT | 192 |
| PRKCA | protein kinase C, alpha | rs2078153 | intron 3 252845 C/G | AGTTACAGGGA C AAGAAGCCTTT | 193 |
| | | | | AGTTACAGGGA G AAGAAGCCTTT | 194 |
| | | | | AAAGGCTTCTT G TCCCTGTAACT | 195 |
| | | | | AAAGGCTTCTT C TCCCTGTAACT | 196 |
| CTLA4 | cytotoxic T-lymphocyte-associated protein 4 | rs5742909 | -318C/T | ATCCAGATCCT C AAAGTGAACAT | 197 |
| | | | | ATCCAGATCCT T AAAGTGAACAT | 198 |
| | | | | ATGTTCACTTT G AGGATCTGGAT | 199 |
| | | | | ATGTTCACTTT A AGGATCTGGAT | 200 |
| MGC33887 | coiled-coil domain containing 46 | rs987931 | intron 21 413506 G/T | GCAGCAGTTT G CCCTGTGAGT | 201 |
| | | | | GCAGCAGTTT T CCCTGTGAGT | 202 |
| | | | | ACTCACAGGG C AAACTGCTGC | 203 |
| | | | | ACTCACAGGG A AAACTGCTGC | 204 |
| CACNG4 | calcium channel, voltage-dependent, gamma subunit 4 | rs4790896 | intron 1 15546 C/T | GACTCCGATGA A GTTTGAGCAGA | 205 |
| | | | | GACTCCGATGA G GTTTGAGCAGA | 206 |
| | | | | TCTGCTCAAAC T TCATCGGAGTC | 207 |
| | | | | TCTGCTCAAAC C TCATCGGAGTC | 208 |
| HELZ | helicase with zinc finger | rs2363846 | intron 18 68091 C/T | TCAATAATAAA C ATCATCTGACC | 209 |
| | | | | TCAATAATAAA T ATCATCTGACC | 210 |
| | | | | GGTCAGATGAT G TTTATTATTGA | 211 |
| | | | | GGTCAGATGAT A TTTATTATTGA | 212 |
| PITPNC1 | phosphatidylinositol transfer protein, cytoplasmic 1 | rs1318 | C/T | TGGGTGGTGTA A ATATTCCTTTA | 213 |
| | | | | TGGGTGGTGTA G ATATTCCTTTA | 214 |
| | | | | GCTAAAGGAATAT T TACACCACCCACC | 215 |
| | | | | GCTAAAGGAATAT C TACACCACCCACC | 216 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| PITPNC1 | phosphatidylinositol transfer protein, cytoplasmic 1 | rs2365403 | C/G | ACTGACTTTCT C TGCCTAATGTA | 217 |
| | | | | ACTGACTTTCT G TGCCTAATGTA | 218 |
| | | | | TACATTAGGCA G AGAAAGTCAGT | 219 |
| | | | | TACATTAGGCA C AGAAAGTCAGT | 220 |
| MC1R | melanocortin 1 receptor | rs1805009 | 294 D/H | ATGCCATCATC C ACCCCCTCATC | 221 |
| | | | | ATGCCATCATC G ACCCCCTCATC | 222 |
| | | | | GATGAGGGGGT G GATGATGGCAT | 223 |
| | | | | GATGAGGGGGT C GATGATGGCAT | 224 |
| MC1R | melanocortin 1 receptor | rs1805006 | 84 Asp/Glu | GCCTTGTCGGA A CTGCTGGTGAG | 225 |
| | | | | GCCTTGTCGGA C CTGCTGGTGAG | 226 |
| | | | | CTCACCAGCAG T TCCGACAAGGC | 227 |
| | | | | CTCACCAGCAG G TCCGACAAGGC | 228 |
| PRKCA | protein kinase C, alpha | rs1010544 | intron 8 388476 C/T | TAAAAAGGTGC A TGTATCTGTGT | 229 |
| | | | | TAAAAAGGTGC G TGTATCTGTGT | 230 |
| | | | | ACACAGATACA T GCACCTTTTTA | 231 |
| | | | | ACACAGATACA C GCACCTTTTTA | 232 |
| PRKCA | protein kinase C, alpha | rs3890137 | intron 8 427857 A/G | GGCTGGCTTT A CCACAGACTG | 233 |
| | | | | TGGCTGGCTTT G CCACAGACTGT | 234 |
| | | | | CAGTCTGTGG T AAAGCCAGCC | 235 |
| | | | | ACAGTCTGTGG C AAAGCCAGCCA | 236 |
| BTNL2 (DRb1*15) | butyrophilin-like 2 | rs2076530 | 11084C/T | TGAAGGTGGTA A GTAAGAATTCT | 237 |
| | | | | TGAAGGTGGTA G GTAAGAATTCT | 238 |
| | | | | AGAATTCTTAC T TACCACCTTCA | 239 |
| | | | | AGAATTCTTAC C TACCACCTTCA | 240 |
| PNMT | phenylethanolamine N-methyltransferase | rs876493 | -184G/A | CACTCACCTCC A GTGTGTCTGCA | 241 |
| | | | | CACTCACCTCC G GTGTGTCTGCA | 242 |
| | | | | CACTCACCTCC A GTGTGTCTGCA | 243 |
| | | | | CACTCACCTCC G GTGTGTCTGCA | 244 |
| PNMT | phenylethanolamine N-methyltransferase | rs3764351 | -390G/A | ATGGCTGCGGG A GGCTGGAGAAG | 245 |
| | | | | ATGGCTGCGGG G GGCTGGAGAAG | 246 |
| | | | | CTTCTCCAGCC T CCCGCAGCCAT | 247 |
| | | | | CTTCTCCAGCC C CCCGCAGCCAT | 248 |
| TRAIL/ TNFSF10 | tumor necrosis factor (ligand) superfamily, member 10 | rs9880164 (rs1131568 in v. 37.1) | 1595C/T | GCTAATTTTTG C ACTTTCAGTAG | 249 |
| | | | | GCTAATTTTTG T ACTTTCAGTAG | 250 |
| | | | | CTACTGAAAGT G CAAAAATTAGC | 251 |
| | | | | CTACTGAAAGT A CAAAAATTAGC | 252 |
| PTPN22 | protein tyrosine phosphatase, non-receptor type 22 | rs2476601 | 1858C/T: (620 W/R) | TTCAGGTGTCC A TACAGGAAGTG | 253 |
| | | | | TTCAGGTGTCC G TACAGGAAGTG | 254 |
| | | | | CACTTCCTGTA T GGACACCTGAA | 255 |
| | | | | CACTTCCTGTA C GGACACCTGAA | 256 |
| MOG | myelin oligodendrocyte glycoprotein | rs3130250 | 15G/A [S5S] | GCAAGCTTATC A AGACCCTCTCT | 257 |
| | | | | GCAAGCTTATC G AGACCCTCTCT | 258 |
| | | | | AGAGAGGGTCT T GATAAGCTTGC | 259 |
| | | | | AGAGAGGGTCT C GATAAGCTTGC | 260 |
| MOG | myelin oligodendrocyte glycoprotein | rs3130253 | 520G/A [V145I] | CTGTTGGCCTC A TCTTCCTCTGC | 261 |
| | | | | CTGTTGGCCTC G TCTTCCTCTGC | 262 |
| | | | | GCAGAGGAAGA T GAGGCCAACAG | 263 |
| | | | | GCAGAGGAAGA C GAGGCCAACAG | 264 |
| SPP1 | secreted phosphoprotein 1 | rs9138 | 1286 A/C | ATTTATGTAGA A GCAAACAAAT | 265 |
| | | | | ATTTATGTAGA C GCAAACAAAT | 266 |
| | | | | ATTTTGTTTGC T TCTACATAAAT | 267 |
| | | | | ATTTTGTTTGC G TCTACATAAAT | 268 |
| SPP1 | secreted phosphoprotein 1 | rs4754 | 282T/C | GAAGATGATGA C GACCATGTGGA | 269 |
| | | | | GAAGATGATGA T GACCATGTGGA | 270 |
| | | | | TCCACATGGTC G TCATCATCTTC | 271 |
| | | | | TCCACATGGTC A TCATCATCTTC | 272 |
| SPP1 | secreted phosphoprotein 1 | rs1126616 | 750C/T | AAGCGGAAAGC C AATGATGAGAG | 273 |
| | | | | AAGCGGAAAGC T AATGATGAGAG | 274 |
| | | | | CTCATCATT G GCTTTCCGC | 275 |
| | | | | CTCATCATT A GCTTTCCGC | 276 |
| SPP1 | secreted phosphoprotein 1 | rs1126772 | 1083A/G | TGGAAATAACT A ATGTGTTTGAT | 277 |
| | | | | TGGAAATAACT G ATGTGTTTGAT | 278 |
| | | | | ATCAAACACAT T AGTTATTTCCA | 279 |
| | | | | ATCAAACACAT C AGTTATTTCCA | 280 |
| HLA-DRA | major histocompatibility complex, class II, DR alpha | rs2395182 | G/T | AGATGCCTATT G TATTACCGAGA | 281 |
| | | | | AGATGCCTATT T TATTACCGAGA | 282 |
| | | | | TCTCGGTAATA C AATAGGCATCT | 283 |
| | | | | TCTCGGTAATA A AATAGGCATCT | 284 |
| HLA | major histocompatibility complex | rs2395166 | C/T | ATAAGGTGAAA C AGAAACAGATC | 285 |
| | | | | ATAAGGTGAAA T AGAAACAGATC | 286 |
| | | | | GATCTGTTTCT G TTTCACCTTAT | 287 |
| | | | | GATCTGTTTCT A TTTCACCTTAT | 288 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| HLA | major histocompatibility complex | rs2213584 | A/G | TGAGCAAAGAG A TTGGACACTGA | 289 |
|  |  |  |  | TGAGCAAAGAG G TTGGACACTGA | 290 |
|  |  |  |  | TCAGTGTCCAA T CTCTTTGCTCA | 291 |
|  |  |  |  | TCAGTGTCCAA C CTCTTTGCTCA | 292 |
| HLA | major histocompatibility complex | rs2227139 | C/T | CAACAGTTCAT C GTGTTTCAAAT | 293 |
|  |  |  |  | CAACAGTTCAT T GTGTTTCAAAT | 294 |
|  |  |  |  | ATATTTGAAACTC G ATGAACTGTTGCT | 295 |
|  |  |  |  | ATATTTGAAACTC A ATGAACTGTTGCT | 296 |
| IL1RN | interleukin 1 receptor antagonist | rs419598 | 2018 T/C | CCAACTAGTTGCTGGATACTTGCAA | 297 |
|  |  |  |  | CCAACTAGTTGCCGGATACTTGCAA | 298 |
|  |  |  |  | TTGCAAGTATCCAGCAACTAGTTGG | 299 |
|  |  |  |  | TTGCAAGTATCCGGCAACTAGTTGG | 300 |
| IL1RN | interleukin 1 receptor antagonist | 2073 intron2 C/T (rs423904) | 2073 C/T Intron2 | TGCCAGGAAAG C CAATGTATGTG | 301 |
|  |  |  |  | TTGCCAGGAAAG T CAATGTATGTGG | 302 |
|  |  |  |  | CCACATACATTG G CTTTCCTGGCAA | 303 |
|  |  |  |  | CCACATACATTG A CTTTCCTGGCAA | 304 |
| NOS2A | nitric oxide synthase 2A isoform 1 | rs1137933 | exon 10 C/T, D346D | TAGCGCTGGAC A TCACAGAAGTC | 305 |
|  |  |  |  | TAGCGCTGGAC G TCACAGAAGTC | 306 |
|  |  |  |  | GACTTCTGTGA T GTCCAGCGCTA | 307 |
|  |  |  |  | GACTTCTGTGA C GTCCAGCGCTA | 308 |
| GABBRA1 | gamma-aminobutyric acid (GABA) B receptor 1 | rs1805057 | G1465A (489 G/S) | ACCAGAACGGC C GCCTCCTCCAG | 309 |
|  |  |  |  | ACCAGAACGGC T GCCTCCTCCAG | 310 |
|  |  |  |  | CTGGAGGAGGC G GCCGTTCTGGT | 311 |
|  |  |  |  | CTGGAGGAGGC A GCCGTTCTGGT | 312 |
| VDR | vitamin D receptor | rs731236 | Taq 1 | TGGATGGCCTC A ATCAGCGCGGC | 313 |
|  |  |  |  | TGGATGGCCTC G ATCAGCGCGGC | 314 |
|  |  |  |  | GCCGCGCTGAT T GAGGCCATCCA | 315 |
|  |  |  |  | GCCGCGCTGAT C GAGGCCATCCA | 316 |
| NOS2A | nitric oxide synthase 2A isoform 1 | rs2779248 | −277 A/G | GGCTGCTAAGA C AGAGGCACCAC | 317 |
|  |  |  |  | GGCTGCTAAGA T AGAGGCACCAC | 318 |
|  |  |  |  | GTGGTGCCTCT G TCTTAGCAGCC | 319 |
|  |  |  |  | GTGGTGCCTCT A TCTTAGCAGCC | 320 |
| IL1B | interleukin 1, beta | rs1143627 | −31 Tata | CTTTTGAAAGC T ATAAAAACAGC | 321 |
|  |  |  |  | CTTTTGAAAGC C ATAAAAACAGC | 322 |
|  |  |  |  | CTTTTGAAAGC T ATAAAAACAGC | 323 |
|  |  |  |  | CTTTTGAAAGC C ATAAAAACAGC | 324 |
| HLA-DRA | major histocompatibility complex, class II, DR alpha | rs2239802 | intron 4 4118 C/G | CCAGATGATAC C AATGTCTGATT | 325 |
|  |  |  |  | CCAGATGATAC G AATGTCTGATT | 326 |
|  |  |  |  | AATCAGACATT G GTATCATCTGG | 327 |
|  |  |  |  | AATCAGACATT C GTATCATCTGG | 328 |
| IL1B | interleukin 1, beta | rs1143634 | +3953-4 | CCTATCTTCTT C GACACATGGGA | 329 |
|  |  |  |  | CCTATCTTCTT T GACACATGGGA | 330 |
|  |  |  |  | TCCCATGTGTC G AAGAAGATAGG | 331 |
|  |  |  |  | TCCCATGTGTC A AAGAAGATAGG | 332 |
| SPP1 | secreted phosphoprotein 1 | rs2853744 | −616G/T | GCAGTCATCCT G CTCTCAGTCAG | 333 |
|  |  |  |  | GCAGTCATCCT T CTCTCAGTCAG | 334 |
|  |  |  |  | CTGACTGAGAG C AGGATGACTGC | 335 |
|  |  |  |  | CTGACTGAGAG A AGGATGACTGC | 336 |
| CCR5 | chemokine (C-C motif) receptor 5 | rs333 | CCR5*D32 | TTTTCCATACAGTCAGTATCAAT | 337 |
|  |  |  |  | TTTTCCATACATTAAAGATAGTC | 338 |
|  |  |  |  | ATTGATACTGACTGTATGGAAAA | 339 |
|  |  |  |  | GACTATCTTTAATGTATGGAAAA | 340 |
| HLA-DRA | major histocompatibility complex, class II, DR alpha | rs3135388 | 3' UTR 5323 C/T | CCTAAAGTGGG A TTGGTTTGTTG | 341 |
|  |  |  |  | CCTAAAGTGGG G TTGGTTTGTTG | 342 |
|  |  |  |  | CAACAAACCAA T CCCACTTTAGG | 343 |
|  |  |  |  | CAACAAACCAA C CCCACTTTAGG | 344 |
| HLA | major histocompatibility complex | rs9268458 | A/C | AAAGTGCTCGG A TGTTGGGATTA | 345 |
|  |  |  |  | AAAGTGCTCGG C TGTTGGGATTA | 346 |
|  |  |  |  | TAATCCCAACA T CCGAGCACTTT | 347 |
|  |  |  |  | TAATCCCAACA G CCGAGCACTTT | 348 |
| HLA | major histocompatibility complex | rs6457594 | A/G | TCCACACATAC A GGTTTGTCACT | 349 |
|  |  |  |  | TCCACACATAC G GGTTTGTCACT | 350 |
|  |  |  |  | AGTGACAAACC T GTATGTGTGGA | 351 |
|  |  |  |  | AGTGACAAACC C GTATGTGTGGA | 352 |
| HLA | major histocompatibility complex | rs7451962 | A/G | GGCAGGAATTC A GAATCCCTCAT | 353 |
|  |  |  |  | GGCAGGAATTC G GAATCCCTCAT | 354 |
|  |  |  |  | ATGAGGGATTC T GAATTCCTGCC | 355 |
|  |  |  |  | ATGAGGGATTC C GAATTCCTGCC | 356 |
| HLA | major histocompatibility complex | rs7451962 | A/G | GGGCAGGAATTC A GAATCCCTCATC | 357 |
|  |  |  |  | GGGCAGGAATTC G GAATCCCTCATC | 358 |
|  |  |  |  | GATGAGGGATTC T GAATTCCTGCCC | 359 |
|  |  |  |  | GATGAGGGATTC C GAATTCCTGCCC | 360 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| HLA | major histocompatibility complex | rs7451962 | A/G | GCAGGAATTC A GAATCCCTCA | 361 |
| | | | | GCAGGAATTC G GAATCCCTCA | 362 |
| | | | | TGAGGGATTC T GAATTCCTGC | 363 |
| | | | | TGAGGGATTC C GAATTCCTGC | 364 |
| PNMT | phenylethanolamine N-methyltransferase | rs3764351 | -390G/A | ATGGCTGCGGG A GGCTGGAGAAG | 365 |
| | | | | ATGGCTGCGGG G GGCTGGAGAAG | 366 |
| | | | | TTCTCCAGCC T CCCGCAGCCA | 367 |
| | | | | TTCTCCAGCC C CCCGCAGCCA | 368 |
| KIF1B | kinesin family member 18 | rs10492972 | C/T | CGCTACAATTCT C CTGGTCAGGTTT | 369 |
| | | | | CGCTACAATTCT T CTGGTCAGGTTT | 370 |
| | | | | AAACCTGACCAG G AGAATTGTAGCG | 371 |
| | | | | AAACCTGACCAG A AGAATTGTAGCG | 372 |
| IGF2R | Immunoglobulin G Fc Receptor II | rs12202350 | C/T | GATAACTTCACA C AGATTGAAATGT | 373 |
| | | | | GATAACTTCACA T AGATTGAAATGT | 374 |
| | | | | ACATTTCAATCT G TGTGAAGTTATC | 375 |
| | | | | ACATTTCAATCT A TGTGAAGTTATC | 376 |
| GRIN2A | glutamate receptor, ionotropic, N-methyl D-aspartate 2A | rs8049651 | C/T | ACACGTCTCGGT C AGGGGGTCTATG | 377 |
| | | | | ACACGTCTCGGT T AGGGGGTCTATG | 378 |
| | | | | CATAGACCCCCT G ACCGAGACGTGT | 379 |
| | | | | CATAGACCCCCT A ACCGAGACGTGT | 380 |
| KLC1 | kinesin light chain 1 | rs8702 | C/G | ACATGCCTTGCT C TAAGGCTTAGTT | 381 |
| | | | | ACATGCCTTGCT G TAAGGCTTAGTT | 382 |
| | | | | AACTAAGCCTTA G AGCAAGGCATGT | 383 |
| | | | | AACTAAGCCTTA C AGCAAGGCATGT | 384 |
| IL7R | interleukin 7 receptor | rs987107 | C/T | TCTCTTTACTGA C AGCAACTCTGGC | 385 |
| | | | | TCTCTTTACTGA T AGCAACTCTGGC | 386 |
| | | | | GCCAGAGTTGCT G TCAGTAAAGAGA | 387 |
| | | | | GCCAGAGTTGCT A TCAGTAAAGAGA | 388 |
| STS | STS steroid sulfatase, isozyme S | rs12861247 | A/G | CAGGGAGGAATG A ACCTGGATTCCT | 389 |
| | | | | CAGGGAGGAATG A ACCTGGATTCCT | 390 |
| | | | | AGGAATCCAGGT T CATTCCTCCCTG | 391 |
| | | | | AGGAATCCAGGT C CATTCCTCCCTG | 392 |
| GPC6 | glypican 6 | rs7995215 | A/G | TGCACACTTCAG A ATGTTTGGCACC | 393 |
| | | | | TGCACACTTCAG G ATGTTTGGCACC | 394 |
| | | | | GGTGCCAAACAT T CTGAAGTGTGCA | 395 |
| | | | | GGTGCCAAACAT C CTGAAGTGTGCA | 396 |
| EREG | epiregulin | rs1350666 | C/T | TGGCTATTGTTT C ATTGCATTCACT | 397 |
| | | | | TGGCTATTGTTT T ATTGCATTCACT | 398 |
| | | | | AGTGAATGCAAT G AAACAATAGCCA | 399 |
| | | | | AGTGAATGCAAT A AAACAATAGCCA | 400 |
| ADRA1A | adrenergic, alpha-1A-, receptor | rs3808585 | C/T | GGGGTAGAGGGG C CGGTATAAAACC | 401 |
| | | | | GGGGTAGAGGGG T CGGTATAAAACC | 402 |
| | | | | GGTTTTATACCG G CCCCTCTACCCC | 403 |
| | | | | GGTTTTATACCG A CCCCTCTACCCC | 404 |
| IL16 | interleukin 16 | rs4128767 | C/T | GCTGTACCATAG C TTTTCTGAGAAA | 405 |
| | | | | GCTGTACCATAG T TTTTCTGAGAAA | 406 |
| | | | | TTTCTCAGAAAA G CTATGGTACAGC | 407 |
| | | | | TTTCTCAGAAAA A CTATGGTACAGC | 408 |
| ARRB2 | arrestin, beta 2 | rs7208257 | C/T | TGAAGTCTTCTC C TTCCTCCGCCAC | 409 |
| | | | | TGAAGTCTTCTC T TTCCTCCGCCAC | 410 |
| | | | | GTGGCGGAGGAA G GAGAAGACTTCA | 411 |
| | | | | GTGGCGGAGGAA A GAGAAGACTTCA | 412 |
| NTF3 | neurotrophin-3 | rs7956189 | A/G | TAAGTAAGTGGC A GAGTGAAGATTG | 413 |
| | | | | TAAGTAAGTGGC G GAGTGAAGATTG | 414 |
| | | | | CAATCTTCACTC T GCCACTTACTTA | 415 |
| | | | | CAATCTTCACTC C GCCACTTACTTA | 416 |
| IL12A | interleukin-12 subunit alpha | rs4680534 | C/T | ATCTATGTGTGT C TGTACATGAATA | 417 |
| | | | | ATCTATGTGTGT T TGTACATGAATA | 418 |
| | | | | TATTCATGTACA G ACACACATAGAT | 419 |
| | | | | TATTCATGTACA A ACACACATAGAT | 420 |
| SLC6A4 | solute carrier family 6, member 4 | rs1042173 | G/T | GAGTAGCATATA G AATTTTATTGCT | 421 |
| | | | | GAGTAGCATATA T AATTTTATTGCT | 422 |
| | | | | AGCAATAAAATT C TATATGCTACTC | 423 |
| | | | | AGCAATAAAATT A TATATGCTACTC | 424 |
| FLJ34870 | FLJ34870 | rs7577925 | A/G | TCCTTGACTGTT A GACACCAAGGAG | 425 |
| | | | | TCCTTGACTGTT G GACACCAAGGAG | 426 |
| | | | | CTCCTTGGTGTC T AACAGTCAAGGA | 427 |
| | | | | CTCCTTGGTGTC C AACAGTCAAGGA | 428 |
| FCRL3 | Fc receptor-like 3 | rs7528684 | nearGene-5' A/G | ATGTACAGATCA A GGACTTCCCGTA | 429 |
| | | | | ATGTACAGATCA G GGACTTCCCGTA | 430 |
| | | | | TACGGGAAGTCC T TGATCTGTACAT | 431 |
| | | | | TACGGGAAGTCC C TGATCTGTACAT | 432 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| IGF2R | insulin-like growth factor 2 receptor | rs6917747 | A/G | CTGGGAGAGACT A GCTCACACAGCT | 433 |
| | | | | CTGGGAGAGACT G GCTCACACAGCT | 434 |
| | | | | AGCTGTGTGAGC T AGTCTCTCCCAG | 435 |
| | | | | AGCTGTGTGAGC C AGTCTCTCCCAG | 436 |
| LOC729293 | LOC729293 | rs6570426 | A/T | CCCTTCCAAATA A CCAATCATACAC | 437 |
| | | | | CCCTTCCAAATA T CCAATCATACAC | 438 |
| | | | | GTGTATGATTGG T TATTTGGAAGGG | 439 |
| | | | | GTGTATGATTGG A TATTTGGAAGGG | 440 |
| SNAP25 | synaptosomal-associated protein, 25 kDa | rs6077690 | A/T | CACTTTGGAAAA A ATTCTGACTACA | 441 |
| | | | | CACTTTGGAAAA T ATTCTGACTACA | 442 |
| | | | | TGTAGTCAGAAT T TTTTCCAAAGTG | 443 |
| | | | | TGTAGTCAGAAT A TTTTCCAAAGTG | 444 |
| MORF4 | mortality factor 4 | rs4473631 | A/C | CAGAGGACAATT A TCTTGGAAAGCA | 445 |
| | | | | CAGAGGACAATT C TCTTGGAAAGCA | 446 |
| | | | | TGCTTTCCAAGA T AATTGTCCTCTG | 447 |
| | | | | TGCTTTCCAAGA G AATTGTCCTCTG | 448 |
| SNAP25 | synaptosomal-associated protein, 25 kDa | rs3787283 | C/T | AATTCCAGAAAA C GAATGATTCCCA | 449 |
| | | | | AATTCCAGAAAA T GAATGATTCCCA | 450 |
| | | | | TGGGAATCATTC G TTTTCTGGAATT | 451 |
| | | | | TGGGAATCATTC A TTTTCTGGAATT | 452 |
| LOC728594 | hypothetical protein LOC728594 | rs3756450 | C/T | CCACAATGATAA C AAAGCCGACTTG | 453 |
| | | | | CCACAATGATAA T AAAGCCGACTTG | 454 |
| | | | | CAAGTCGGCTTT G TTATCATTGTGG | 455 |
| | | | | CAAGTCGGCTTT A TTATCATTGTGG | 456 |
| SLC6A2 | solute carrier family 6 member 2 | rs28386840 | A/T | GGGCTGAGCACC A GTTTCCCCAGCA | 457 |
| | | | | GGGCTGAGCACC T GTTTCCCCAGCA | 458 |
| | | | | TGCTGGGGAAAC T GGTGCTCAGCCC | 459 |
| | | | | TGCTGGGGAAAC A GGTGCTCAGCCC | 460 |
| ZNF544 | zinc finger protein 544 | rs260461 | A/G | ATCAATGTCACT A GATCAAAATCAA | 461 |
| | | | | ATCAATGTCACT G GATCAAAATCAA | 462 |
| | | | | TTGATTTTGATC T AGTGACATTGAT | 463 |
| | | | | TTGATTTTGATC C AGTGACATTGAT | 464 |
| MHC II/ HLA-DQA1 | major histocompatibility complex, class II, DQ alpha 1 | rs2187668 | A/G | AGCTGAGAGTAA A TGAGGACCATGT | 465 |
| | | | | AGCTGAGAGTAA A TGAGGACCATGT | 466 |
| | | | | ACATGGTCCTCA C TTACTCTCAGCT | 467 |
| | | | | ACATGGTCCTCA T TTACTCTCAGCT | 468 |
| SLC6A4 | solute carrier family 6, member 4 | rs2066713 | C/T | GCATTTCCCTTC C GTAGACCCTCTG | 469 |
| | | | | GCATTTCCCTTC T GTAGACCCTCTG | 470 |
| | | | | CAGAGGGTCTAC G GAAGGGAAATGC | 471 |
| | | | | CAGAGGGTCTAC A GAAGGGAAATGC | 472 |
| CSMD1 | CUB and Sushi multiple domains 1 | rs2049306 | A/C | GTTCTGAAAGCA A ACATTTAAATAT | 473 |
| | | | | GTTCTGAAAGCA C ACATTTAAATAT | 474 |
| | | | | ATATTTAAATGT T TGCTTTCAGAAC | 475 |
| | | | | ATATTTAAATGT G TGCTTTCAGAAC | 476 |
| SLC1A3 | solute carrier family 1 member 3 | rs2032893 | A/G | ATAAATAAATAT A CAGAAGCATTGG | 477 |
| | | | | ATAAATAAATAT G CAGAAGCATTGG | 478 |
| | | | | CCAATGCTTCTG T ATATTTATTTAT | 479 |
| | | | | CCAATGCTTCTG C ATATTTATTTAT | 480 |
| LOC647094 | LOC647094 | rs2028455 | A/G | ACATGCCTGCCT A GAATGATTACTT | 481 |
| | | | | ACATGCCTGCCT G GAATGATTACTT | 482 |
| | | | | AAGTAATCATTC T AGGCAGGCATGT | 483 |
| | | | | AAGTAATCATTC C AGGCAGGCATGT | 484 |
| DMRT2 | doublesex and mab-3 related transcription factor 2 | rs17641078 | C/G | AAGATCAGCAAA C AAAACACCAGGC | 485 |
| | | | | AAGATCAGCAAA G AAAACACCAGGC | 486 |
| | | | | GCCTGGTGTTTT G TTTGCTGATCTT | 487 |
| | | | | GCCTGGTGTTTT C TTTGCTGATCTT | 488 |
| DBH | dopamine beta-hydroxylase (dopamine beta-monooxygenase) | rs1611115 | C/T | TCAGTCTACTTG C GGGAGAGGACAG | 489 |
| | | | | TCAGTCTACTTG T GGGAGAGGACAG | 490 |
| | | | | CTGTCCTCTCCC G CAAGTAGACTGA | 491 |
| | | | | CTGTCCTCTCCC A CAAGTAGACTGA | 492 |
| MMP24 | MMP24 matrix metallopeptidase 24 | rs1555322 | A/G | CACGCACTTCAC A TGTATCTTATTC | 493 |
| | | | | CACGCACTTCAC G TGTATCTTATTC | 494 |
| | | | | GAATAAGATACA T GTGAAGTGCGTG | 495 |
| | | | | GAATAAGATACA C GTGAAGTGCGTG | 496 |
| DSEL | DSEL | rs13353224 | A/G | ATCAGAGTTAAT A AACTTCCCTATT | 497 |
| | | | | ATCAGAGTTAAT G AACTTCCCTATT | 498 |
| | | | | AATAGGGAAGTT T ATTAACTCTGAT | 499 |
| | | | | AATAGGGAAGTT C ATTAACTCTGAT | 500 |
| C1orf125 | chromosome 1 open reading frame 125 | rs12047808 | A/G | AATGAGAGGGT A ACACACATTATG | 501 |
| | | | | AATGAGAGGGGT G ACACACATTATG | 502 |
| | | | | CATAATGTGTGT T ACCCCTCTCATT | 503 |
| | | | | CATAATGTGTGT C ACCCCTCTCATT | 504 |
| GPC5 | glypican 5 | rs10492503 | A/T | TGGATAACTGCT A CAATTATAGTTT | 505 |
| | | | | TGGATAACTGCT T CAATTATAGTTT | 506 |

TABLE 7-continued

Examples of Probes Used in SNP Analysis

| Gene Symbol | Gene Name | rs ID | SNP | Oligonucleotide sequence (5' > 3') | SEQ ID NO: |
|---|---|---|---|---|---|
| C1GALT1 | core 1 synthase, glycoprotein-N-acetylgalactosamine 3-beta-galactosyltransferase, 1 | rs10259085 | C/T | AAACTATAATTG T AGCAGTTATCCA | 507 |
| | | | | AAACTATAATTG A AGCAGTTATCCA | 508 |
| | | | | TAAAAACAATTA C GTAACACCAAGA | 509 |
| | | | | TAAAAACAATTA G GTAACACCAAGA | 510 |
| | | | | TCTTGGTGTTAC G TAATTGTTTTTA | 511 |
| | | | | TCTTGGTGTTAC A TAATTGTTTTTA | 512 |
| MET | met proto-oncogene (hepatocyte growth factor receptor) | rs10243024 | A/G | TATTTTTACTCC A AATACTGTTTCA | 513 |
| | | | | TATTTTTACTCC G AATACTGTTTCA | 514 |
| | | | | TGAAACAGTATT T GGAGTAAAAATA | 515 |
| | | | | TGAAACAGTATT C GGAGTAAAAATA | 516 |
| ICOS | inducible T-cell co-stimulator | rs4404254 | C/T | TTACAAGTTTAG C TCTTTTTGTAGA | 517 |
| | | | | TTACAAGTTTAG T TCTTTTTGTAGA | 518 |
| | | | | TCTACAAAAGA G CTAAACTTGTAA | 519 |
| | | | | TCTACAAAAGA C CTAAACTTGTAA | 520 |
| OAS1 | 2',5'-oligoadenylate synthetase 1 | rs3741981/ rs1131454 | A/G | CAGTTGACTGGC A GCTATAAACCTA | 521 |
| | | | | CAGTTGACTGGC G GCTATAAACCTA | 522 |
| | | | | TAGGTTTATAGC T GCCAGTCAACTG | 523 |
| | | | | TAGGTTTATAGC C GCCAGTCAACTG | 524 |

TABLE 8

Examples of Forward Primers Used in SNP Analysis

| SNP # | Gene Symbol | rs ID | Forward Primers (sequence 5' > 3') | SEQ ID NO: |
|---|---|---|---|---|
| 1 | EBF1 | rs1368297 | CCAAATCTTGGTTTTCAGTGC | 525 |
| 2 | RANTES/CCL5 | rs2280788 | TATGATACCGGCCAATGCTT | 526 |
| 3 | RANTES/CCL5 | rs2107538 | CACCTCCTTTGGGGACTGTA | 527 |
| 4 | TGFB1 | rs17851976 | TCGATAGTCTTGCAGGTGGA | 528 |
| 6 | UPC2 | rs659366 | TTCGCCTTTAATTGGCTGAC | 529 |
| 7 | IKBL | rs3130062 | TGAGTCCTTCTCAGCCTGGT | 530 |
| 8 | Apo I/Fas (CD 95) | rs1800682 | CCTATGGCGCAACATCTGTA | 531 |
| 9 | Apo I/Fas (CD 95) | rs3781202 | CCAATGCCTACCTAGCCTGT | 532 |
| 10 | IL2 | rs2069763 | GCATTGCACTAAGTCTTGCAC | 533 |
| 11 | IL2 | rs2069762 | ACCCCCAAAGACTGACTGAA | 534 |
| 12 | IL10 | rs1800896 | ATGGAGGCTGGATAGGAGGT | 535 |
| 13 | IL4R | rs1801275 | CAACCTGAGCCAGAAACCTG | 536 |
| 14 | PTPRC | rs17612648 | ATGCCCAGTGTTCCACTTTC | 537 |
| 15 | PTPRC | rs4915154 | GCAGATGTCCCAGGAGAGAG | 538 |
| 16 | PD-1/PDCD1 | rs11568821 | TATAGCCAGGACCCCACCTC | 539 |
| 17 | CRYAB | rs14133 | TGCTTGGGATTCCTGACTCT | 540 |
| 18 | CRYAB | rs762550 | GCACCCAATTCCTAAAGCAC | 541 |
| 19 | CRYAB | rs2234702 | GCACCCAATTCCTAAAGCAC | 542 |
| 20 | NDUFS5 | rs2889683 | TTGCTCAACTTTAGTTTTTCAGTCA | 543 |
| 21 | NDUFS5 | rs6981 | GCAGCGGGATAAGCTGATAA | 544 |
| 22 | NDUFS7 | rs2074897 | GGTCTCCAGGGACAGACGTA | 545 |
| 24 | NDUFA7 | rs2288414 | CGCTGAGCACTGCAAATCTA | 546 |
| 25 | NDUFA7 | rs561 | CCAAGGAGGCAAAGTAGTCG | 547 |
| 26 | ADAMTS14 | rs4747075 | TCCATTGTGGGGATTTTTGT | 548 |
| 27 | ADAMTS14 | rs7081273 | GCCTTGGAAGGAGAAAGGAG | 549 |
| 28 | ADAMTS14 | rs4746060 | CTGGGGAGGTGCTATGGAT | 550 |
| 29 | NFKBIA | rs11569591 | AGGCTTTTCACTCCTCCAAA | 551 |
| 29 | NFKBIA | rs11569591 | AGGCTTTTCACTCCTCCAAA | 552 |
| 29 | NFKBIA | rs11569591 | AGGCTTTTCACTCCTCCAAA | 553 |
| 30 | SPP1 | rs28357094 | TGTGTGTGTGCGTTTTTGTTT | 554 |
| 31 | HLA-DR*1501 | rs367398 | TGAGACACATAGCAGCAGCA | 555 |
| 32 | HLA-DR*1501 | rs1800629 | GCCCCTCCCAGTTCTAGTTC | 556 |
| 34 | IL7R | rs11567685 | GCAGGCAGATCACTTGAGGT | 557 |
| 35 | IL7R | rs7718919 | GCTCTGCCATTGTTGCATAA | 558 |
| 36 | IL7R | rs11567686 | CCGTCTCCACTGAAAACACA | 559 |
| 37 | IFNAR1 | rs2257167 | GCTCAGATTGGTCCTCCAGA | 560 |
| 38 | IFNAR2 | rs7279064 | TCTTGTCTTTGCTCCCATTTT | 561 |
| 39 | IL1B | rs1799916 | GGCAGAGAGACAGAGAGACTCC | 562 |
| 40 | IFNGR2 | rs9808753 | TGTACAACGCAGAGCAGGTC | 563 |
| 41 | Apo I/Fas (CD 95) | rs2234978 | TGCAGAAAGCACAGAAAGGA | 564 |
| 42 | CD24 | rs8734 | ACCCACGCAGATTTATTCCA | 565 |
| 43 | MEFV | rs28940577 | TTGGAGACAAGACAGCATGG | 566 |
| 44 | CTLA4 | rs231775 | GGATCCTGAAAGGTTTTGCTC | 567 |
| 45 | CNTF | rs1800169 | GACACTGGGGTGATGACAGA | 568 |
| 46 | MHC2TA | rs3087456 | AGGTTCCCCAACAGACTTTT | 569 |
| 47 | VDR | rs1544410 | CCTCACTGCCCTTAGCTCTG | 570 |
| 48 | PRKCA | rs7220007 | AGCTGAGTGTTGTGCAGTGG | 571 |

TABLE 8-continued

Examples of Forward Primers Used in SNP Analysis

| SNP # | Gene Symbol | rs ID | Forward Primers (sequence 5' > 3') | SEQ ID NO: |
|---|---|---|---|---|
| 49 | PRKCA | rs887797 | AACCCCTGCATTTCAGAATTT | 572 |
| 50 | PRKCA | rs2078153 | AAACAACTCCACCCAGGTTC | 573 |
| 51 | CTLA4 | rs5742909 | TGGTTAAGGATGCCCAGAAG | 574 |
| 52 | MGC33887 | rs987931 | CTTCGATAAATAGTGCTGGGAAA | 575 |
| 53 | CACNG4 | rs4790896 | CTTAATCGGAAAGCTGTGTCG | 576 |
| 54 | HELZ | rs2363846 | GGAAAACACCAACACTCTCCA | 577 |
| 55 | PITPNC1 | rs1318 | TCAGTTGCAAAGCTACGATGA | 578 |
| 56 | PITPNC1 | rs2365403 | ACGCCTTTGGAACAACAATC | 579 |
| 57 | MC1R | rs1805009 | AACCTCTTTCTCGCCCTCAT | 580 |
| 58 | MC1R | rs1805006 | TGCACTCACCCATGTACTGC | 581 |
| 59 | PRKCA | rs1010544 | ACCAGCTTGCAGTCTCTGCT | 582 |
| 60 | PRKCA | rs3890137 | AGCCAGGAGACCTGAGACTG | 583 |
| 61 | BTNL2 (DRb1*15) | rs2076530 | TACTCAGTGCCAGACCTTCG | 584 |
| 62 | PNMT | rs876493 | TAAAGATTGTGGGGGTGAGG | 585 |
| 63 | PNMT | rs3764351 | AAAGGGCCTAATTCCCCAGT | 586 |
| 64 | TRAIL/TNFSF10 | rs9880164 (rs1131568 in v. 37.1) | ACTACAGGCATGTGCCAACA | 587 |
| 65 | PTPN22 | rs2476601 | TGCCCATCCCACACTTTATT | 588 |
| 66 | MOG | rs3130250 | TCTGTCCCAGGAACAGTAGA | 589 |
| 67 | MOG | rs3130253 | ATGCTGAGTGTTGGGGATTC | 590 |
| 68 | SPP1 | rs9138 | GCTTCATGGAAACTCCCTGT | 591 |
| 69 | SPP1 | rs4754 | AGACCCTTCCAAGTAAGTCCAA | 592 |
| 70 | SPP1 | rs1126616 | AGAGTGCTGAAACCCACAGC | 593 |
| 71 | SPP1 | rs1126772 | GAACATGAAATGCTTCTTTCTCAG | 594 |
| 72 | HLA-DRA | rs2395182 | GACTGGCCTTACCCATTCTG | 595 |
| 73 | HLA | rs2395166 | CGCTTTCCATAGAAACCTTGG | 596 |
| 74 | HLA | rs2213584 | CATTGCAGGATTTACATATCAACA | 597 |
| 75 | HLA | rs2227139 | CAGCCAAGATGAAACCCAAG | 598 |
| 76 | IL1RN | rs419598 | ACAAGTTCTGGGGGACACAG | 599 |
| 77 | IL1RN | 2073 Intron2 C/T (rs423904) | ACAAGTTCTGGGGGACACAG | 600 |
| 78 | NOS2A | rs1137933 | CAGAGTGATAGCGGCGAGT | 601 |
| 79 | GABBRA1 | rs1805057 | TGGTCGGTAATGGTCTGGTT | 602 |
| 80 | VDR | rs731236 | AGGTCGGCTAGCTTCTGGAT | 603 |
| 81 | NOS2A | rs2779248 | CTCTGTGTGGTGCCTCTTCA | 604 |
| 82 | IL1B | rs1143627 | CAGTTTCTCCCTCGCTGTTT | 605 |
| 83 | HLA-DRA | rs2239802 | TGATCAAGGTGCCCGTCTAT | 606 |
| 84 | IL1B | rs1143634 | ATGCTCAGGTGTCCTCCAAG | 607 |
| 85 | SPP1 | rs2853744 | ACACAGCGGAATTCAGAACC | 608 |
| 87 | CCR5 | rs333 | CGTCTCTCCCAGGAATCATC | 609 |
| 88 | HLA-DRA | rs3135388 | CATTTGGGCTTGGTCTCATT | 610 |
| 89 | HLA | rs9268458 | AATGGGGCCTCACTATGTTG | 611 |
| 90 | HLA | rs6457594 | TGAATTCTGGGGGCTTACTG | 612 |
| 91 | HLA | rs7451962 | GCCAGCTCAGTGAGGTCAGTA | 613 |
| 92 | HLA | rs7451962 | GCCAGCTCAGTGAGGTCAGTA | 614 |
| 93 | HLA | rs7451962 | GCCAGCTCAGTGAGGTCAGTA | 615 |
| 94 | PNMT | rs3764351 | AAAGGGCCTAATTCCCCAGT | 616 |
| 95 | KIF1B | rs10492972 | TGACCTCACATTGGCTATTGG | 617 |
| 96 | IGF2R | rs12202350 | ATAGGCATAAGCCACCATGC | 618 |
| 97 | GRIN2A | rs8049651 | AGCATTCCTGCCACTCACTT | 619 |
| 98 | KLC1 | rs8702 | AGAAAAGCAGAATGCCCAAA | 620 |
| 99 | IL7R | rs987107 | ACCTCTGGGAAAAAGCCCTA | 621 |
| 100 | STS | rs12861247 | TAAACAAGGAAGGGCACTGG | 622 |
| 101 | GPC6 | rs7995215 | CAGCAGTGTCCATGAGAATCA | 623 |
| 102 | EREG | rs1350666 | TTGGGGGCTATTTAAGTTCA | 624 |
| 103 | ADRA1A | rs3808585 | CTCGGGCAAAGACTCTTGTT | 625 |
| 104 | IL16 | rs4128767 | ATGATCACACCACTGCATCC | 626 |
| 105 | ARRB2 | rs7208257 | CAGCGTCTCCAGCCTCTTAG | 627 |
| 106 | NTF3 | rs7956189 | AATCCTTTGAGGGAGCCAGT | 628 |
| 107 | IL12A | rs4680534 | TCAGGTTTTCCTCCTACTTCAAA | 629 |
| 108 | SLC6A4 | rs1042173 | AAACTGCGTAGGAGAACAGG | 630 |
| 109 | FLJ34870 | rs7577925 | TGGGAGCAAAGTGAAAGTCA | 631 |
| 110 | FCRL3 | rs7528684 | TCACACAGCCTTTGGTTCTG | 632 |
| 111 | IGF2R | rs6917747 | TTCCTGGTGGTGGTTTTCTC | 633 |
| 112 | LOC729293 | rs6570426 | CATTTCTGGAACTGCCTTGG | 634 |
| 113 | SNAP25 | rs6077690 | CCTCCTCCATTCCTTCACAA | 635 |
| 114 | MORF4 | rs4473631 | TCATATGCTGGCAGTTTACA | 636 |
| 115 | SNAP25 | rs3787283 | AGGGCTGCTACCAGCATAAA | 637 |
| 116 | LOC728594 | rs3756450 | TTGGAGACAGCAGTCAGTGG | 638 |
| 117 | SLC6A2 | rs28386840 | GCGGCCTTCATGGATAAATA | 639 |
| 118 | ZNF544 | rs260461 | GAGGCACAAGTCCAAAATC | 640 |
| 119 | MHC II/HLA-DQA1 | rs2187668 | CTTAGCCACATGCCCATTTT | 641 |
| 120 | SLC6A4 | rs2066713 | CTTCTGAGATGGACCGCATT | 642 |
| 121 | CSMD1 | rs2049306 | TTGCCACTAGTTCTGAAAGCA | 643 |
| 122 | SLC1A3 | rs2032893 | ATCCCTATCAGGGGCAGACT | 644 |
| 123 | LOC647094 | rs2028455 | GCATAATGCCACAGGACCTT | 645 |

TABLE 8-continued

Examples of Forward Primers Used in SNP Analysis

| SNP # | Gene Symbol | rs ID | Forward Primers (sequence 5' > 3') | SEQ ID NO: |
|---|---|---|---|---|
| 124 | DMRT2 | rs17641078 | GCCTCACACTCCTGAGATCC | 646 |
| 125 | DBH | rs1611115 | ACAGGAGGGAAAAGGAAGGA | 647 |
| 126 | MMP24 | rs1555322 | CAACAGCTGCCATTCTGTGT | 648 |
| 127 | DSEL | rs13353224 | TGGGGGTGCTAAGACAGTTT | 649 |
| 128 | C1orf125 | rs12047808 | GGCAAATCAAATCCAGCAGT | 650 |
| 129 | GPC5 | rs10492503 | GCGGAAGATTGGATAACTGC | 651 |
| 130 | C1GALT1 | rs10259085 | AGTCATAAGGCCGGAGTCCT | 652 |
| 131 | MET | rs10243024 | AGCGATTTCTGGAAGCATGT | 653 |
| 132 | ICOS | rs4404254 | CCCGGAATTGAAAGCAAAT | 654 |
| 133 | OAS1 | rs3741981/rs1131454 | GGATCAGGAATGGACCTCAA | 655 |

TABLE 9

Examples of Reverse Primers Used in SNP Analysis

| SNP # | Gene Symbol | rs ID | Reverse Primers (sequence 5' > 3') | SEQ ID NO: |
|---|---|---|---|---|
| 1 | EBF1 | rs1368297 | CTGCCCAGTGCTTTTCATTT | 656 |
| 2 | RANTES/CCL5 | rs2280788 | GAGGGCAGTAGCAATGAGGA | 657 |
| 3 | RANTES/CCL5 | rs2107538 | GGAGTGGCAGTTAGGACAGG | 658 |
| 4 | TGFB1 | rs17851976 | ACCACACCAGCCCTGTTC | 659 |
| 6 | UPC2 | rs659366 | AGTCCCTTCTGCTGGTGAAA | 660 |
| 7 | IKBL | rs3130062 | CTCTCACGCAGCTCTTCCTC | 661 |
| 8 | Apo I/Fas (CD 95) | rs1800682 | AGTTGGGGAGGTCTTGAAGG | 662 |
| 9 | Apo I/Fas (CD 95) | rs3781202 | AAGGGCCTTGTCTTTTAGGC | 663 |
| 10 | IL2 | rs2069763 | TCCTGGTGAGTTTGGGATTC | 664 |
| 11 | IL2 | rs2069762 | TCTTGCTCTTGTCCACCACA | 665 |
| 12 | IL10 | rs1800896 | CTTCCCCAGGTAGAGCAACA | 666 |
| 13 | IL4R | rs1801275 | CCACATTTCTCTGGGGACAC | 667 |
| 14 | PTPRC | rs17612648 | CTTTTGTGTGCCAACCTGTG | 668 |
| 15 | PTPRC | rs4915154 | AACTGAAGACACTACTAGAGCAGCA | 669 |
| 16 | PD-1/PDCD1 | rs11568821 | AGGCAGGCACACACATGG | 670 |
| 17 | CRYAB | rs14133 | GACTTGTGATCCGGGATTTG | 671 |
| 18 | CRYAB | rs762550 | GGTCAACATGTCAGCACCAG | 672 |
| 19 | CRYAB | rs2234702 | GGTCAACATGTCAGCACCAG | 673 |
| 20 | NDUFS5 | rs2889683 | AGTGGCAGACCATCCACATC | 674 |
| 21 | NDUFS5 | rs6981 | CTTTGACAAGGAGGTTTGTCG | 675 |
| 22 | NDUFS7 | rs2074897 | AGGAATCGTTCTGGGGAGAG | 676 |
| 24 | NDUFA7 | rs2288414 | GCTCTGTCCTTTCTCCACCA | 677 |
| 25 | NDUFA7 | rs561 | AGAAAGTCCCTGTGGGTGTG | 678 |
| 26 | ADAMTS14 | rs4747075 | CTGGCTTCTCTGGGAGGAAT | 679 |
| 27 | ADAMTS14 | rs7081273 | GCTTGGCTCTCAGGAGACAG | 680 |
| 28 | ADAMTS14 | rs4746060 | GCTTCAAAGTGCTCAAATGGT | 681 |
| 29 | NFKBIA | rs11569591 | AAGGACGCACTGTGGTTAGG | 682 |
| 29 | NFKBIA | rs11569591 | AAGGACGCACTGTGGTTAGG | 683 |

TABLE 9-continued

Examples of Reverse Primers Used in SNP Analysis

| SNP # | Gene Symbol | rs ID | Reverse Primers (sequence 5' > 3') | SEQ ID NO: |
|---|---|---|---|---|
| 29 | NFKBIA | rs11569591 | AAGGACGCACTGTGGTTAGG | 684 |
| 30 | SPP1 | rs28357094 | CCAAGCCCTCCCAGAATTTA | 685 |
| 31 | HLA-DR*1501 | rs367398 | CAGGAAACAGCTCAGACGTG | 686 |
| 32 | HLA-DR*1501 | rs1800629 | AAAGTTGGGGACACACAAGC | 687 |
| 34 | IL7R | rs11567685 | GCCCAGGCTGGAGTACAATA | 688 |
| 35 | IL7R | rs7718919 | CACACCACAGTAGGCATTCAA | 689 |
| 36 | IL7R | rs11567686 | GCCCAGGCTGGAGTACAATA | 690 |
| 37 | IFNAR1 | rs2257167 | TTCGCCTAATTTTTCTCTCACA | 691 |
| 38 | IFNAR2 | rs7279064 | GACTTCCTGCCAGTGCTCTC | 692 |
| 39 | IL1B | rs1799916 | AAACAGCGAGGGAGAAACTG | 693 |
| 40 | IFNGR2 | rs9808753 | TGTTTCCCACGGGTTTGATA | 694 |
| 41 | Apo I/Fas (CD 95) | rs2234978 | CTGGGCTATGGAGCAAGACT | 695 |
| 42 | CD24 | rs8734 | ACCACGAAGAGACTGGCTGT | 696 |
| 43 | MEFV | rs28940577 | GCTTGGGAGGCTCCTTTATT | 697 |
| 44 | CTLA4 | rs231775 | CCTCCTCCATCTTCATGCTC | 698 |
| 45 | CNTF | rs1800169 | GCCAACAAAACATGGAAGGT | 699 |
| 46 | MHC2TA | rs3087456 | CAAGCTAAGCCAACATGCAA | 700 |
| 47 | VDR | rs1544410 | CAGGAATGTTGAGCCCAGTT | 701 |
| 48 | PRKCA | rs7220007 | GCATAGCCTCGGAGACAGAC | 702 |
| 49 | PRKCA | rs887797 | TCCCGGGTATATGATCTCCA | 703 |
| 50 | PRKCA | rs2078153 | TCACCTAAGGACAGTCTAAAATTGC | 704 |
| 51 | CTLA4 | rs5742909 | AGCCGTGGGTTAGCTGTTA | 705 |
| 52 | MGC33887 | rs987931 | GCTTGGAAGTTGCCATTCAT | 706 |
| 53 | CACNG4 | rs4790896 | AGCTTGCCACAGGACAGTTT | 707 |
| 54 | HELZ | rs2363846 | TTGAGTTGTTGCAGCAGAGATT | 708 |
| 55 | PITPNC1 | rs1318 | TGCCTTTTGATGACTGGGTTA | 709 |
| 56 | PITPNC1 | rs2365403 | AGCAGGGAAGCACTTGAAGA | 710 |
| 57 | MC1R | rs1805009 | GGTCACACAGGAACCAGACC | 711 |
| 58 | MC1R | rs1805006 | TGCAGGTGATCACGTCAATG | 712 |
| 59 | PRKCA | rs1010544 | CCCCAAACCCTGACTTTCAT | 713 |
| 60 | PRKCA | rs3890137 | TACTGATTGAGCCCCCTTGT | 714 |
| 61 | BTNL2 (DRb1*15) | rs2076530 | TTAAAGTGGCAGGAGCAGGT | 715 |
| 62 | PNMT | rs876493 | CCCATTCATCCATCTCCCTTA | 716 |
| 63 | PNMT | rs3764351 | CCTCACCCCACAATCTTTA | 717 |
| 64 | TRAIL/TNFSF10 | rs9880164 (rs1131568 in v. 37.1) | CGAGATCAAGAGATCAAGACCA | 718 |
| 65 | PTPN22 | rs2476601 | TGGATAGCAACTGCTCCAAG | 719 |
| 66 | MOG | rs3130250 | GCTGGAAGACACTTGGAGGA | 720 |
| 67 | MOG | rs3130253 | TCCAAGAAGCCAGCTCATTT | 721 |

TABLE 9-continued

Examples of Reverse Primers Used in SNP Analysis

| SNP # | Gene Symbol | rs ID | Reverse Primers (sequence 5' > 3') | SEQ ID NO: |
|---|---|---|---|---|
| 68 | SPP1 | rs9138 | CACACCACAAAAAGATAATCACAA | 722 |
| 69 | SPP1 | rs4754 | CATCAGACTGGTGAGAATCATC | 723 |
| 70 | SPP1 | rs1126616 | ATTCACGGCTGACTTTGGAA | 724 |
| 71 | SPP1 | rs1126772 | TGAACATAGACATAACCCTGAAGC | 725 |
| 72 | HLA-DRA | rs2395182 | TCCACTCAAAGACACATCTTCAA | 726 |
| 73 | HLA | rs2395166 | TGTGTCAGGCAATGAGGCTA | 727 |
| 74 | HLA | rs2213584 | GGCATCTGAGACTATGTCTAACAGAA | 728 |
| 75 | HLA | rs2227139 | GGGTTGGGGAGAAAGATATGA | 729 |
| 76 | IL1RN | rs419598 | ATTGCACCTAGGGTTTGTGC | 730 |
| 77 | IL1RN | 2073 Intron2 C/T (rs423904) | ATTGCACCTAGGGTTTGTGC | 731 |
| 78 | NOS2A | rs1137933 | CCCTTCAATGGCTGGTACAT | 732 |
| 79 | GABBRA1 | rs1805057 | TGGCCTATGATGCCATCTG | 733 |
| 80 | VDR | rs731236 | CTGAGAGCTCCTGTGCCTTC | 734 |
| 81 | NOS2A | rs2779248 | CAGCTTCCTGGACTCCTGTC | 735 |
| 82 | IL1B | rs1143627 | TTTGCTACTCCTTGCCCTTC | 736 |
| 83 | HLA-DRA | rs2239802 | TGTAAGGCACATGGAGGTGA | 737 |
| 84 | IL1B | rs1143634 | GTGATCGTACAGGTGCATCG | 738 |
| 85 | SPP1 | rs2853744 | GCTTGTTACTTAGACAAATGGCACT | 739 |
| 87 | CCR5 | rs333 | TGTAGGGAGCCCAGAAGAGA | 740 |
| 88 | HLA-DRA | rs3135388 | TCCATACCTTGGGGTTTCAG | 741 |
| 89 | HLA | rs9268458 | TGCAGGGTTTTGATACATGG | 742 |
| 90 | HLA | rs6457594 | ATTTCTCCTCCACCCTCTGC | 743 |
| 91 | HLA | rs7451962 | GAACGGTCCTCTCACTTCTCA | 744 |
| 92 | HLA | rs7451962 | GAACGGTCCTCTCACTTCTCA | 745 |
| 93 | HLA | rs7451962 | GAACGGTCCTCTCACTTCTCA | 746 |
| 94 | PNMT | rs3764351 | CCTCACCCCACAATCTTTA | 747 |
| 95 | KIF1B | rs10492972 | CACATTGGAATTTGGGAAGAA | 748 |
| 96 | IGF2R | rs12202350 | AGGTGAGGGGCTGAAGAAGT | 749 |
| 97 | GRIN2A | rs8049651 | GTCCTTCTCCGACTGTGAGC | 750 |
| 98 | KLC1 | rs8702 | CATGACGGTGACCTGTTGAC | 751 |
| 99 | IL7R | rs987107 | CCCCACTTCCACCAAAATTA | 752 |
| 100 | STS | rs12861247 | GGATTGGCTGAACATTTTGG | 753 |
| 101 | GPC6 | rs7995215 | AATGGGTGGGGTGTTATTT | 754 |
| 102 | EREG | rs1350666 | GACTGAGTGCAATGCCAAAA | 755 |
| 103 | ADRA1A | rs3808585 | CGCTTTTTCCACCAGGTTT | 756 |
| 104 | IL16 | rs4128767 | CTGGGCTCTGCTTGTTTCTC | 757 |
| 105 | ARRB2 | rs7208257 | AGCTGTTCCTCCCGTACCTT | 758 |

TABLE 9-continued

Examples of Reverse Primers Used in SNP Analysis

| SNP # | Gene Symbol | rs ID | Reverse Primers (sequence 5' > 3') | SEQ ID NO: |
|---|---|---|---|---|
| 106 | NTF3 | rs7956189 | AGACTAGTGCCGAGGGTTCA | 759 |
| 107 | IL12A | rs4680534 | TCGTGCAAAATCAAGGTTCA | 760 |
| 108 | SLC6A4 | rs1042173 | CAAGCTTGCATGGACACACT | 761 |
| 109 | FLJ34870 | rs7577925 | ATCTTGGCATCTCCTTGGTG | 762 |
| 110 | FCRL3 | rs7528684 | TGAGAAGGGCTTTGGCTTTA | 763 |
| 111 | IGF2R | rs6917747 | CCCTAAGAAAGGTGCCATGA | 764 |
| 112 | LOC729293 | rs6570426 | AAATGGTGCTGGGAAAACTG | 765 |
| 113 | SNAP25 | rs6077690 | GAATAGGGGAAAGGGGTTT | 766 |
| 114 | MORF4 | rs4473631 | CTTGAAGGATGCTTTCCAAGA | 767 |
| 115 | SNAP25 | rs3787283 | AGTTTGGTTTCCCCACACTG | 768 |
| 116 | LOC728594 | rs3756450 | TTTGCCCTAAATGCCAAGTC | 769 |
| 117 | SLC6A2 | rs28386840 | AGGGAAGGAAACCAGGAGAA | 770 |
| 118 | ZNF544 | rs260461 | GGAGAAAGGCAGAGGGAGAT | 771 |
| 119 | MHC II/HLA-DQA1 | rs2187668 | TCTCCGGTGGTAGATCTTGG | 772 |
| 120 | SLC6A4 | rs2066713 | TCCTGACCTCACATGATCCA | 773 |
| 121 | CSMD1 | rs2049306 | TTCACTTCGACCAGGATATTCA | 774 |
| 122 | SLC1A3 | rs2032893 | TCGGGCATTCACAATGTTTA | 775 |
| 123 | LOC647094 | rs2028455 | AATCAGTGCTGCTGCTTGTG | 776 |
| 124 | DMRT2 | rs17641078 | TCAGGACCCGATTTGTCAGT | 777 |
| 125 | DBH | rs1611115 | ACAGGACCTTTGCCATCATC | 778 |
| 126 | MMP24 | rs1555322 | GATCCTGAGGGTGGAACTGA | 779 |
| 127 | DSEL | rs13353224 | CATGAGGCTGGGAGTTAGGA | 780 |
| 128 | C1orf125 | rs12047808 | GGCAGGCAATACACACACAC | 781 |
| 129 | GPC5 | rs10492503 | CATCCCATGGATTTGTAGCC | 782 |
| 130 | C1GALT1 | rs10259085 | GCAAGGCATCTATCCTGGAG | 783 |
| 131 | MET | rs10243024 | GATGGGTCCCCATTTTTCTT | 784 |
| 132 | ICOS | rs4404254 | GCTCTACCCCATGAGAATGC | 785 |
| 133 | OAS1 | rs3741981/rs1131454 | GGAGAACTCGCCCTCTTTCT | 786 |

Table 10 shows SNPs and associated risk alleles for MS disease severity. Presence of one or more risk alleles as indicated in Table 10 at the specified SNPs is associated with a higher probability that the subject has a greater severity of MS disease phenotype, for example: a multiple sclerosis severity score (MSSS) of 2.5 or greater; an increase in size and/or distribution of T2 brain lesions; an increased number of focal lesions in the spinal cord; an increased T2 lesion load in the brain; and/or the presence of diffuse abnormalities in the spinal cord.

TABLE 10

| Marker | RS | Risk allele |
|---|---|---|
| PGK_317 | rs2107538 | T |
| PGK_309 | rs1137933 | G |
| PGK_324 | rs1318 | A |
| PGK_066 | rs2069763 | G |
| PGK_027 | rs423904 | C |
| PGK_321 | rs876493 | A |
| PGK_169 | rs10243024 | G |
| PGK_156 | rs10259085 | G |

TABLE 10-continued

| Marker | RS | Risk allele |
|---|---|---|
| PGK_310 | rs1042173 | A |
| PGK_268 | rs10492503 | T |
| KIF1B | rs10492972 | G |
| PGK_014 | rs12047808 | G |
| PGK_154 | rs12202350 | A |
| PGK_377 | rs12861247 | G |
| PGK_332 | rs13353224 | A |
| PGK_059 | rs1350666 | G |
| PGK_358 | rs1555322 | A |
| PGK_202 | rs1611115 | A |
| PGK_186 | rs17641078 | G |
| PGK_302 | rs1805009 | G |
| PGK_328 | rs2028455 | G |
| PGK_097 | rs2032893 | A |
| PGK_176 | rs2049306 | A |
| PGK_312 | rs2066713 | A |
| NDUFS7 | rs2074897 | A |
| BTNL2 | rs2076530 | G |
| PGK_134 | rs2187668 | A |
| MHC II | rs2213584 | A |
| MHC II | rs2227139 | C |
| FAS | rs2234978 | T |
| MHC II | rs2239802 | G |
| MHC II | rs2395182 | G |
| PGK_350 | rs260461 | A |
| PGK_289 | rs28386840 | A |
| MHC2TA | rs3087456 | G |
| MHC II | rs3135388 | A |
| PGK_256 | rs3741981 in NCBI db SNP build 129; *Homo sapiens* build 36.3 (rs1131454 in NCBI db SNP build 131; *Homo sapiens* build 37.1) | A |
| PGK_086 | rs3756450 | A |
| FAS | rs3781202 | CT heterozygosity |
| PGK_355 | rs3787283 | A |
| PGK_181 | rs3808585 | A |
| PGK_280 | rs4128767 | G |
| PGK_036 | rs4404254 | G |
| PGK_070 | rs4473631 | C |
| PGK_051 | rs4680534 | A |
| PGK_352 | rs6077690 | T |
| HLA_M9001 | rs6457594 | A |
| PGK_150 | rs6570426 | T |
| UCP2 | rs659366 | C |
| PGK_155 | rs6917747 | G |
| PGK_304 | rs7208257 | A |
| PGK_011 | rs7528684 | G |
| PGK_030 | rs7577925 | A |
| CRYAB | rs762550 | A |
| PGK_234 | rs7956189 | G |
| GPC6 | rs7995215 | G |
| PGK_285 | rs8049651 | A |
| KLC1 | rs8702 | G |
| IFNGR2 | rs9808753 | G |
| IL7R | rs987107 | A |

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety, particularly for the disclosure referenced herein.

---

The invention claimed is:

1. A method of treating a human subject having multiple sclerosis (MS), the method comprising:
   obtaining a DNA sample from the subject;
   detecting in the DNA sample the presence of at least one T allele at single nucleotide polymorphism (SNP) rs2107538, at least one G allele at SNP rs1137933, and at least one A allele at SNP rs1318;
   correlating the presence of said at least one T allele at SNP rs2107538, at least one G allele at SNP rs1137933, and at least one A allele at SNP rs1318 with an increased MS disease severity, wherein the increased MS disease severity is measured by multiple sclerosis severity score or increased size and/or distribution of T2 brain lesions; and
   administering an MS therapeutic comprising interferon-beta or glatiramer acetate to the subject when at least one T allele at SNP rs2107538, at least one G allele at SNP rs1137933, and at least one A allele at SNP rs1318 is present.

2. The method according to claim 1, wherein the method comprises:
   detecting the presence of the TT genotype at SNP rs2107538, the GG genotype at SNP rs1137933 and the AA genotype at SNP rs1318; and
   correlating the presence of said TT genotype at SNP rs2107538, GG genotype at SNP rs1137933 and AA genotype at SNP rs1318 with the increased MS disease severity.

3. The method according to claim 1, wherein said increased MS disease severity is a multiple sclerosis severity score (MSSS) of 2.5 or greater.

4. The method according to claim 1, wherein the method further comprises the measurement of at least one clinical variable.

5. The method according to claim 4, wherein the at least one clinical variable is selected from: age of the subject at onset of multiple sclerosis, gender of the subject and type of multiple sclerosis at onset of multiple sclerosis.

6. The method according to claim 1, wherein detecting in the DNA sample the presence of at least one T allele at SNP rs2107538, at least one G allele at SNP rs1137933, and at least one A allele at SNP rs1318 comprises:
   (i) extracting and/or amplifying DNA from the sample that has been obtained from the subject; and
   (ii) contacting the DNA with an array comprising at least one probe suitable for determining the identity of at least one allele at each of SNP rs2107538, SNP rs1137933, and SNP rs1318.

7. The method according to claim 6, wherein the array is a DNA array, a DNA microarray or a bead array.

8. The method according to claim 6, wherein:
   said at least one probe for determining the identity of at least one allele at SNP rs2107538 is selected from the group consisting of AGGGAAAGGAGGTAAGATCT-GTA (SEQ ID NO: 9), AGGGAAAGGAGATAA-GATCTGTA (SEQ ID NO: 10), TACAGATCTTAC-CTCCTTTCCCT (SEQ ID NO: 11) and TACAGATCTTATCTCCTTTCCCT (SEQ ID NO: 12);
   said at least one probe for determining the identity of at least one allele at SNP rs1137933 is selected from the group consisting of TAGCGCTGGACATCACA-GAAGTC (SEQ ID NO: 305), TAGCGCTGGACGT-CACAGAAGTC (SEQ ID NO: 306), GACTTCTGT-GATGTCCAGCGCTA (SEQ ID NO: 307) and GACTTCTGTGACGTCCAGCGCTA (SEQ ID NO: 308); and
   said at least one probe for determining the identity of at least one allele at SNP rs1318 is selected from the group consisting of TGGGTGGTGTAAATATTCCTTTA (SEQ ID NO: 213), TGGGTGGTGTAGATATTC-CTTTA (SEQ ID NO: 214), GCTAAAGGAATATTTA-CACCACCCACC (SEQ ID NO: 215), and GCTAAAG-GAATATCTACACCACCCACC (SEQ ID NO: 216).

9. The method according to claim 1, wherein the method comprises amplifying DNA from a sample that has been obtained from the subject, and wherein said amplifying comprises contacting the DNA with at least one forward primer selected from CACCTCCTTTGGGGACTGTA (SEQ ID NO: 527), CAGAGTGATAGCGGCGAGT (SEQ ID NO: 601) and TCAGTTGCAAAGCTACGATGA (SEQ ID NO: 578).

10. The method according to claim 1, wherein the method comprises amplifying DNA from a sample that has been obtained from the subject, and wherein said amplifying comprises contacting the DNA with at least one reverse primer selected from GGAGTGGCAGTTAGGACAGG (SEQ ID NO: 658), CCCTTCAATGGCTGGTACAT (SEQ ID NO: 732) and TGCCTTTTGATGACTGGGTTA (SEQ ID NO: 709).

* * * * *

SEQUENCE LISTING

<160> NUMBER OF SEQ ID NOS: 786

<210> SEQ ID NO 1
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 1
taaagttagt cagttctatg ctt                                            23

<210> SEQ ID NO 2
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 2
taaagttagt ctgttctatg ctt                                            23

<210> SEQ ID NO 3
<211> LENGTH: 23
<212> TYPE: DNA
<213> ORGANISM: Artificial sequence

```
<220> FEATURE:
<223> OTHER INFORMATION: Synthetic sequence: Oligonucleotide probe

<400> SEQUENCE: 3
aagcatagaa ctgactaact tta                                              23

<210> SEQ ID NO 4
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 4
aagcatagaa cagactaact tta                                              23

<210> SEQ ID NO 5
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 5
gggatgcccc tcaactggcc cta                                              23

<210> SEQ ID NO 6
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 6
gggatgcccc tgaactggcc cta                                              23

<210> SEQ ID NO 7
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 7
tagggccagt tgaggggcat ccc                                              23

<210> SEQ ID NO 8
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 8
tagggccagt tcaggggcat ccc                                              23

<210> SEQ ID NO 9
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 9
agggaaagga ggtaagatct gta                                              23
```

```
<210> SEQ ID NO 10
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 10
agggaaagga gataagatct gta                                              23

<210> SEQ ID NO 11
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 11
tacagatctt acctcctttc cct                                              23

<210> SEQ ID NO 12
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 12
tacagatctt atctcctttc cct                                              23

<210> SEQ ID NO 13
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 13
gtagcagcag cggcagcagc cgc                                              23

<210> SEQ ID NO 14
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 14
gtagcagcag cagcagcagc cgc                                              23

<210> SEQ ID NO 15
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 15
gcggctgctg ccgctgctgc tac                                              23

<210> SEQ ID NO 16
<211> LENGTH: 23
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 16
gcggctgctg ctgctgctgc tac                                              23

<210> SEQ ID NO 17
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 17
ggggtaactg acgcgtgaac agc                                              23

<210> SEQ ID NO 18
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 18
ggggtaactg atgcgtgaac agc                                              23

<210> SEQ ID NO 19
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 19
gctgttcacg cgtcagttac ccc                                              23

<210> SEQ ID NO 20
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 20
gctgttcacg catcagttac ccc                                              23

<210> SEQ ID NO 21
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 21
cagagggatc ccgtcgaccc cca                                              23

<210> SEQ ID NO 22
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 22
cagagggatc ctgtcgaccc cca                                              23

<210> SEQ ID NO 23
```

```
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 23
tgggggtcga cgggatccct ctg                                          23

<210> SEQ ID NO 24
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 24
tgggggtcga caggatccct ctg                                          23

<210> SEQ ID NO 25
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 25
gtccattcca gaaacgtctg tga                                          23

<210> SEQ ID NO 26
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 26
gtccattcca ggaacgtctg tga                                          23

<210> SEQ ID NO 27
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 27
tcacagacgt ttctggaatg gac                                          23

<210> SEQ ID NO 28
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 28
tcacagacgt tcctggaatg gac                                          23

<210> SEQ ID NO 29
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 29
```

-continued ataaaattttt cctagcaaat aaa                                          23

<210> SEQ ID NO 30
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 30 ataaaattttt cttagcaaat aaa                                          23

<210> SEQ ID NO 31
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 31
tttatttgct aggaaaattt tat                                           23

<210> SEQ ID NO 32
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 32
tttatttgct aagaaaattt tat                                           23

<210> SEQ ID NO 33
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 33
gagcatttac tgctggattt aca                                           23

<210> SEQ ID NO 34
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 34
gagcatttac ttctggattt aca                                           23

<210> SEQ ID NO 35
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 35
tgtaaatcca gcagtaaatg ctc                                           23

<210> SEQ ID NO 36
<211> LENGTH: 23
<212> TYPE: DNA

```
<213> ORGANISM: Artificial sequence
<220> FEATURE:
<223> OTHER INFORMATION: Synthetic sequence: Oligonucleotide probe

<400> SEQUENCE: 36
tgtaaatcca gaagtaaatg ctc                                          23

<210> SEQ ID NO 37
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 37 tttctttgt cataaaacta cac                                           23

<210> SEQ ID NO 38
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 38 tttctttgt cctaaaacta cac                                           23

<210> SEQ ID NO 39
<211> LENGTH: 31
<212> TYPE: DNA
<213> ORGANISM: Artificial sequence
<220> FEATURE:
<223> OTHER INFORMATION: Synthetic sequence: Oligonucleotide probe

<400> SEQUENCE: 39
ttcagtgtag ttttatgaca aagaaaattt t                                 31

<210> SEQ ID NO 40
<211> LENGTH: 31
<212> TYPE: DNA
<213> ORGANISM: Artificial sequence
<220> FEATURE:
<223> OTHER INFORMATION: Synthetic sequence: Oligonucleotide probe

<400> SEQUENCE: 40
ttcagtgtag ttttaggaca aagaaaattt t                                 31

<210> SEQ ID NO 41
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 41
gcttctttgg gaagggggaag taggg                                       25

<210> SEQ ID NO 42
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 42
gcttctttgg gagggggaag taggg                                        25
```

<210> SEQ ID NO 43
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 43
ccctacttcc ccttcccaaa gaagc                                    25

<210> SEQ ID NO 44
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 44
ccctacttcc ccctcccaaa gaagc                                    25

<210> SEQ ID NO 45
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 45
cagtggctat cgggagtttg tac                                      23

<210> SEQ ID NO 46
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 46
cagtggctat caggagtttg tac                                      23

<210> SEQ ID NO 47
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 47
tacaaactcc cgatagccac t                                        21

<210> SEQ ID NO 48
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 48
tacaaactcc tgatagccac t                                        21

<210> SEQ ID NO 49
<211> LENGTH: 23
<212> TYPE: DNA
<213> ORGANISM: Artificial sequence
<220> FEATURE:

```
<223> OTHER INFORMATION: Synthetic sequence: Oligonucleotide probe

<400> SEQUENCE: 49
gcattctcac ccgcaagcac ctt                                              23

<210> SEQ ID NO 50
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 50
gcattctcac cggcaagcac ctt                                              23

<210> SEQ ID NO 51
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 51
aaggtgcttg cgggtgagaa tgc                                              23

<210> SEQ ID NO 52
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 52
aaggtgcttg ccggtgagaa tgc                                              23

<210> SEQ ID NO 53
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 53
tcacagcgaa cgcctcaggt ctg                                              23

<210> SEQ ID NO 54
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 54
tcacagcgaa cacctcaggt ctg                                              23

<210> SEQ ID NO 55
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 55
cagacctgag gcgttcgctg tga                                              23
```

```
<210> SEQ ID NO 56
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 56
cagacctgag gtgttcgctg tga                                              23

<210> SEQ ID NO 57
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 57
agcccacctg cggtctccgg ggg                                              23

<210> SEQ ID NO 58
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 58
agcccacctg cagtctccgg ggg                                              23

<210> SEQ ID NO 59
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 59
cccccggaga ccgcaggtgg gct                                              23

<210> SEQ ID NO 60
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 60
cccccggaga ctgcaggtgg gct                                              23

<210> SEQ ID NO 61
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 61
tgaaacaaga ccatgacaag tca                                              23

<210> SEQ ID NO 62
<211> LENGTH: 23
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 62
tgaaacaaga cgatgacaag tca                                               23

<210> SEQ ID NO 63
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 63
tgacttgtca tggtcttgtt tca                                               23

<210> SEQ ID NO 64
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 64
tgacttgtca tcgtcttgtt tca                                               23

<210> SEQ ID NO 65
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 65
gagccacata gaacgaaaga tgc                                               23

<210> SEQ ID NO 66
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 66
gagccacata ggacgaaaga tgc                                               23

<210> SEQ ID NO 67
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 67
gcatctttcg ttctatgtgg ctc                                               23

<210> SEQ ID NO 68
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 68
catctttcgt cctatgtggc t                                                 21

<210> SEQ ID NO 69
<211> LENGTH: 23
```

```
<212> TYPE: DNA
<213> ORGANISM: Artificial sequence
<220> FEATURE:
<223> OTHER INFORMATION: Synthetic sequence: Oligonucleotide probe

<400> SEQUENCE: 69
gccacataga acgaaagatg caa                                         23

<210> SEQ ID NO 70
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 70
gccacataga aggaaagatg caa                                         23

<210> SEQ ID NO 71
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 71
ttgcatcttt cgttctatgt ggc                                         23

<210> SEQ ID NO 72
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 72
ttgcatcttt ccttctatgt ggc                                         23

<210> SEQ ID NO 73
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 73
acaacagcag aaataataat caa                                         23

<210> SEQ ID NO 74
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 74
acaacagcag agataataat caa                                         23

<210> SEQ ID NO 75
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 75
```
ttgattatta tttctgctgt tgt                                              23

<210> SEQ ID NO 76
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 76
ttgattatta tctctgctgt tgt                                              23

<210> SEQ ID NO 77
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 77
cagctgctga tatctggagg ctg                                              23

<210> SEQ ID NO 78
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 78
cagctgctga tgtctggagg ctg                                              23

<210> SEQ ID NO 79
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 79
cagcctccag atatcagcag ctg                                              23

<210> SEQ ID NO 80
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 80
cagcctccag acatcagcag ctg                                              23

<210> SEQ ID NO 81
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 81
gccctgatgg cacttatcaa aag                                              23

<210> SEQ ID NO 82
<211> LENGTH: 23
<212> TYPE: DNA
<213> ORGANISM: Artificial sequence

```
<220> FEATURE:
<223> OTHER INFORMATION: Synthetic sequence: Oligonucleotide probe

<400> SEQUENCE: 82
gccctgatgg cgcttatcaa aag                                              23

<210> SEQ ID NO 83
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 83
cttttgataa gtgccatcag ggc                                              23

<210> SEQ ID NO 84
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 84
cttttgataa gcgccatcag ggc                                              23

<210> SEQ ID NO 85
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 85
atgtcagccc tccgtttcag ggg                                              23

<210> SEQ ID NO 86
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 86
atgtcagccc tgcgtttcag ggg                                              23

<210> SEQ ID NO 87
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 87
cccctgaaac ggagggctga cat                                              23

<210> SEQ ID NO 88
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 88
cccctgaaac gcagggctga cat                                              23
```

<210> SEQ ID NO 89
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 89
ccacctcttt ataggaggag ctgga                                    25

<210> SEQ ID NO 90
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 90
ccacctcttt atgggaggag ctgga                                    25

<210> SEQ ID NO 91
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 91
ccagctcctc ctataaagag gtg                                      23

<210> SEQ ID NO 92
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 92
ccagctcctc ccataaagag gtg                                      23

<210> SEQ ID NO 93
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 93
cccagatgat gacattcgcc ttc                                      23

<210> SEQ ID NO 94
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 94
cccagatgat ggcattcgcc ttc                                      23

<210> SEQ ID NO 95
<211> LENGTH: 23
<212> TYPE: DNA
<213> ORGANISM: Artificial sequence
<220> FEATURE:
<223> OTHER INFORMATION: Synthetic sequence: Oligonucleotide probe

```
<400> SEQUENCE: 95
gaaggcgaat gtcatcatct ggg                                              23

<210> SEQ ID NO 96
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 96
gaaggcgaat gccatcatct ggg                                              23

<210> SEQ ID NO 97
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 97
catttggcaa acgtaggctg gtc                                              23

<210> SEQ ID NO 98
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 98
catttggcaa aggtaggctg gtc                                              23

<210> SEQ ID NO 99
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 99
gaccagccta cgtttgccaa atg                                              23

<210> SEQ ID NO 100
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 100
gaccagccta cctttgccaa atg                                              23

<210> SEQ ID NO 101
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 101
gcacatctat actgggtcat ctt                                              23

<210> SEQ ID NO 102
```

```
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 102
gcacatctat attgggtcat ctt                                          23

<210> SEQ ID NO 103
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 103
aagatgaccc agtatagatg tgc                                          23

<210> SEQ ID NO 104
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 104
aagatgaccc aatatagatg tgc                                          23

<210> SEQ ID NO 105
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 105
gcgtgggggg gtgggggcga agc                                          23

<210> SEQ ID NO 106
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 106
gggtgggggg gaggggggcga agc                                          23

<210> SEQ ID NO 107
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 107
gcttcgcccc caccccccca cgc                                          23

<210> SEQ ID NO 108
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 108
```

```
gcttcgcccc ctccccccca ccc                                              23
```

<210> SEQ ID NO 109
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 109

```
cgtggggggg tgggggcgaa g                                                21
```

<210> SEQ ID NO 110
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 110

```
ggtggggggg aggggggcgaa g                                               21
```

<210> SEQ ID NO 111
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 111

```
cttcgccccc acccccccac g                                                21
```

<210> SEQ ID NO 112
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 112

```
cttcgccccc tccccccac c                                                 21
```

<210> SEQ ID NO 113
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 113

```
tgcgtggggg ggtgggggcg aagct                                            25
```

<210> SEQ ID NO 114
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 114

```
ggggtggggg ggaggggggcg aagct                                           25
```

<210> SEQ ID NO 115
<211> LENGTH: 25
<212> TYPE: DNA

```
<213> ORGANISM: Artificial sequence
<220> FEATURE:
<223> OTHER INFORMATION: Synthetic sequence: Oligonucleotide probe

<400> SEQUENCE: 115
agcttcgccc ccaccccccc acgca                                              25

<210> SEQ ID NO 116
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 116
agcttcgccc cctcccccccc acccc                                             25

<210> SEQ ID NO 117
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 117
gacacaatct cgccgcctcc ctg                                                23

<210> SEQ ID NO 118
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 118
gacacaatct ctccgcctcc ctg                                                23

<210> SEQ ID NO 119
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 119
cagggaggcg gcgagattgt gtc                                                23

<210> SEQ ID NO 120
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 120
cagggaggcg gagagattgt gtc                                                23

<210> SEQ ID NO 121
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 121
ctccaagccc cagtccctgt ccc                                                23
```

<210> SEQ ID NO 122
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 122
ctccaagccc cggtccctgt ccc                                            23

<210> SEQ ID NO 123
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 123
gggacaggga ctggggcttg gag                                            23

<210> SEQ ID NO 124
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 124
gggacaggga ccggggcttg gag                                            23

<210> SEQ ID NO 125
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 125 tgagggcat gaggacgggg ttc                                             23

<210> SEQ ID NO 126
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 126 tgagggcat ggggacgggg ttc                                             23

<210> SEQ ID NO 127
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 127
aaccccgtcc tcatgcccct c                                              21

<210> SEQ ID NO 128
<211> LENGTH: 21
<212> TYPE: DNA
<213> ORGANISM: Artificial sequence
<220> FEATURE:

<223> OTHER INFORMATION: Synthetic sequence: Oligonucleotide probe

<400> SEQUENCE: 128
aaccccgtcc ccatgcccct c                                         21

<210> SEQ ID NO 129
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 129
gcatttgcct gcagtcctag cta                                       23

<210> SEQ ID NO 130
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 130
gcatttgcct gtagtcctag cta                                       23

<210> SEQ ID NO 131
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 131
tagctaggac tgcaggcaaa tgc                                       23

<210> SEQ ID NO 132
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 132
tagctaggac tacaggcaaa tgc                                       23

<210> SEQ ID NO 133
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 133
cacaaatggg tgaggctgta ttc                                       23

<210> SEQ ID NO 134
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 134
cacaaatggg ttaggctgta ttc                                       23

```
<210> SEQ ID NO 135
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 135
gaatacagcc tcacccattt gtg                                              23

<210> SEQ ID NO 136
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 136
gaatacagcc tacccattt gtg                                               23

<210> SEQ ID NO 137
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 137
cctgggaggt gaaaattgca gtg                                              23

<210> SEQ ID NO 138
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 138
cctgggaggt ggaaattgca gtg                                              23

<210> SEQ ID NO 139
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 139
cactgcaatt ttcacctccc agg                                              23

<210> SEQ ID NO 140
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 140
cactgcaatt tccacctccc agg                                              23

<210> SEQ ID NO 141
<211> LENGTH: 25
<212> TYPE: DNA
<213> ORGANISM: Artificial sequence
<220> FEATURE:
<223> OTHER INFORMATION: Synthetic sequence: Oligonucleotide probe
```

<400> SEQUENCE: 141
acatatagct tacttatctg gaaaa          25

<210> SEQ ID NO 142
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 142
acatatagct tagttatctg gaaaa          25

<210> SEQ ID NO 143
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 143
ttttccagat aagtaagcta tatgt          25

<210> SEQ ID NO 144
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 144
ttttccagat aactaagcta tatgt          25

<210> SEQ ID NO 145
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 145
atgccttcat cgtcagatca ctt          23

<210> SEQ ID NO 146
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 146
atgccttcat cttcagatca ctt          23

<210> SEQ ID NO 147
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 147
aagtgatctg acgatgaagg cat          23

<210> SEQ ID NO 148
<211> LENGTH: 23

```
<212> TYPE: DNA
<213> ORGANISM: Artificial sequence
<220> FEATURE:
<223> OTHER INFORMATION: Synthetic sequence: Oligonucleotide probe

<400> SEQUENCE: 148
aagtgatctg aagatgaagg cat                                              23

<210> SEQ ID NO 149
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 149
aagagaatcc cagagcagcc tgt                                              23

<210> SEQ ID NO 150
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 150
aagagaatcc ccgagcagcc tgt                                              23

<210> SEQ ID NO 151
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 151
acaggctgct ctgggattct ctt                                              23

<210> SEQ ID NO 152
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 152
acaggctgct cggggattct ctt                                              23

<210> SEQ ID NO 153
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 153
tgttgtctac caagtgcagt tta                                              23

<210> SEQ ID NO 154
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 154
```
tgttgtctac cgagtgcagt tta                                           23

<210> SEQ ID NO 155
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 155
taaactgcac ttggtagaca aca                                           23

<210> SEQ ID NO 156
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 156
taaactgcac tcggtagaca aca                                           23

<210> SEQ ID NO 157
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 157
gaatctccaa ccttaaatcc tgt                                           23

<210> SEQ ID NO 158
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 158
gaatctccaa ctttaaatcc tgt                                           23

<210> SEQ ID NO 159
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 159
acaggattta aggttggaga ttc                                           23

<210> SEQ ID NO 160
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 160
acaggattta agttggaga ttc                                            23

<210> SEQ ID NO 161
<211> LENGTH: 23
<212> TYPE: DNA
<213> ORGANISM: Artificial sequence

```
<220> FEATURE:
<223> OTHER INFORMATION: Synthetic sequence: Oligonucleotide probe

<400> SEQUENCE: 161
caccaccaag gtggctggtg gtg                                              23

<210> SEQ ID NO 162
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 162
caccaccaag gcggctggtg gtg                                              23

<210> SEQ ID NO 163
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 163
caccaccagc caccttggtg gtg                                              23

<210> SEQ ID NO 164
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 164
caccaccagc cgccttggtg gtg                                              23

<210> SEQ ID NO 165
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 165
gggtggtgat aatgatgaag gaa                                              23

<210> SEQ ID NO 166
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 166
gggtggtgat agtgatgaag gaa                                              23

<210> SEQ ID NO 167
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 167
ttccttcatc attatcacca ccc                                              23
```

<210> SEQ ID NO 168
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 168
ttccttcatc actatcacca ccc        23

<210> SEQ ID NO 169
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 169
tgaacctggc taccaggacc tgg        23

<210> SEQ ID NO 170
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 170
tgaacctggc tgccaggacc tgg        23

<210> SEQ ID NO 171
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 171
ccaggtcctg gtagccaggt tca        23

<210> SEQ ID NO 172
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 172
ccaggtcctg gcagccaggt tca        23

<210> SEQ ID NO 173
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 173
cctgtatcct cagccaggtg aag        23

<210> SEQ ID NO 174
<211> LENGTH: 23
<212> TYPE: DNA
<213> ORGANISM: Artificial sequence
<220> FEATURE:
<223> OTHER INFORMATION: Synthetic sequence: Oligonucleotide probe

```
<400> SEQUENCE: 174
cctgtatcct cggccaggtg aag                                               23

<210> SEQ ID NO 175
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 175
cttcacctgg ctgaggatac agg                                               23

<210> SEQ ID NO 176
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 176
cttcacctgg ccgaggatac agg                                               23

<210> SEQ ID NO 177
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 177
ttcagaggtg tagggagggc tta                                               23

<210> SEQ ID NO 178
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 178
ttcagaggtg tggggagggc tta                                               23

<210> SEQ ID NO 179
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 179
taagccctcc ctacacctct gaa                                               23

<210> SEQ ID NO 180
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 180
taagccctcc ccacacctct gaa                                               23

<210> SEQ ID NO 181
```

-continued

```
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 181
gacaggcctg cacattccca ata                                              23

<210> SEQ ID NO 182
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 182
gacaggcctg cgcattccca ata                                              23

<210> SEQ ID NO 183
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 183
attgggaatg tgcaggcctg t                                                21

<210> SEQ ID NO 184
<211> LENGTH: 19
<212> TYPE: DNA
<213> ORGANISM: Artificial sequence
<220> FEATURE:
<223> OTHER INFORMATION: Synthetic sequence: Oligonucleotide probe

<400> SEQUENCE: 184
ttgggaatgc gcaggcctg                                                   19

<210> SEQ ID NO 185
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 185
cccctgctgg cagattgttg cta                                              23

<210> SEQ ID NO 186
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 186
cccctgctgg cggattgttg cta                                              23

<210> SEQ ID NO 187
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 187
```

-continued tagcaacaat ctgccagcag ggg                        23

<210> SEQ ID NO 188
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 188
tagcaacaat ccgccagcag ggg                        23

<210> SEQ ID NO 189
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 189 gtcttttttaa tagctgtaga catct                     25

<210> SEQ ID NO 190
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 190 gtcttttttaa taactgtaga catct                     25

<210> SEQ ID NO 191
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 191 gtcttttttaa tagctgtaga catct                     25

<210> SEQ ID NO 192
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 192 gtcttttttaa taactgtaga catct                     25

<210> SEQ ID NO 193
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 193
agttacaggg acaagaagcc ttt                        23

<210> SEQ ID NO 194
<211> LENGTH: 23
<212> TYPE: DNA

```
<213> ORGANISM: Artificial sequence
<220> FEATURE:
<223> OTHER INFORMATION: Synthetic sequence: Oligonucleotide probe

<400> SEQUENCE: 194
agttacaggg agaagaagcc ttt                                              23

<210> SEQ ID NO 195
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 195
aaaggcttct tgtccctgta act                                              23

<210> SEQ ID NO 196
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 196
aaaggcttct tctccctgta act                                              23

<210> SEQ ID NO 197
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 197
atccagatcc tcaaagtgaa cat                                              23

<210> SEQ ID NO 198
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 198
atccagatcc ttaaagtgaa cat                                              23

<210> SEQ ID NO 199
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 199
atgttcactt tgaggatctg gat                                              23

<210> SEQ ID NO 200
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 200
atgttcactt taaggatctg gat                                              23
```

```
<210> SEQ ID NO 201
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 201
gcagcagttt gccctgtgag t                                              21

<210> SEQ ID NO 202
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 202
gcagcagttt tccctgtgag t                                              21

<210> SEQ ID NO 203
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 203
actcacaggg caaactgctg c                                              21

<210> SEQ ID NO 204
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 204
actcacaggg aaaactgctg c                                              21

<210> SEQ ID NO 205
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 205
gactccgatg aagtttgagc aga                                            23

<210> SEQ ID NO 206
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 206
gactccgatg aggtttgagc aga                                            23

<210> SEQ ID NO 207
<211> LENGTH: 23
<212> TYPE: DNA
<213> ORGANISM: Artificial sequence
<220> FEATURE:
```

```
<223> OTHER INFORMATION: Synthetic sequence: Oligonucleotide probe

<400> SEQUENCE: 207
tctgctcaaa cttcatcgga gtc                                          23

<210> SEQ ID NO 208
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 208
tctgctcaaa cctcatcgga gtc                                          23

<210> SEQ ID NO 209
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 209
tcaataataa acatcatctg acc                                          23

<210> SEQ ID NO 210
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 210
tcaataataa atatcatctg acc                                          23

<210> SEQ ID NO 211
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 211
ggtcagatga tgtttattat tga                                          23

<210> SEQ ID NO 212
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 212
ggtcagatga tatttattat tga                                          23

<210> SEQ ID NO 213
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 213
tgggtggtgt aaatattcct tta                                          23
```

```
<210> SEQ ID NO 214
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 214
tgggtggtgt agatattcct tta                                              23

<210> SEQ ID NO 215
<211> LENGTH: 27
<212> TYPE: DNA
<213> ORGANISM: Artificial sequence
<220> FEATURE:
<223> OTHER INFORMATION: Synthetic sequence: Oligonucleotide probe

<400> SEQUENCE: 215
gctaaaggaa tatttacacc acccacc                                          27

<210> SEQ ID NO 216
<211> LENGTH: 27
<212> TYPE: DNA
<213> ORGANISM: Artificial sequence
<220> FEATURE:
<223> OTHER INFORMATION: Synthetic sequence: Oligonucleotide probe

<400> SEQUENCE: 216
gctaaaggaa tatctacacc acccacc                                          27

<210> SEQ ID NO 217
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 217
actgactttc tctgcctaat gta                                              23

<210> SEQ ID NO 218
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 218
actgactttc tgtgcctaat gta                                              23

<210> SEQ ID NO 219
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 219
tacattaggc agagaaagtc agt                                              23

<210> SEQ ID NO 220
<211> LENGTH: 23
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 220
tacattaggc acagaaagtc agt                                              23

<210> SEQ ID NO 221
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 221
atgccatcat ccaccccctc atc                                              23

<210> SEQ ID NO 222
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 222
atgccatcat cgaccccctc atc                                              23

<210> SEQ ID NO 223
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 223
gatgaggggg tggatgatgg cat                                              23

<210> SEQ ID NO 224
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 224
gatgaggggg tcgatgatgg cat                                              23

<210> SEQ ID NO 225
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 225
gccttgtcgg aactgctggt gag                                              23

<210> SEQ ID NO 226
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 226
gccttgtcgg acctgctggt gag                                              23

<210> SEQ ID NO 227
<211> LENGTH: 23
```

```
<212> TYPE: DNA
<213> ORGANISM: Artificial sequence
<220> FEATURE:
<223> OTHER INFORMATION: Synthetic sequence: Oligonucleotide probe

<400> SEQUENCE: 227
ctcaccagca gttccgacaa ggc                                           23

<210> SEQ ID NO 228
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 228
ctcaccagca ggtccgacaa ggc                                           23

<210> SEQ ID NO 229
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 229
taaaaaggtg catgtatctg tgt                                           23

<210> SEQ ID NO 230
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 230
taaaaaggtg cgtgtatctg tgt                                           23

<210> SEQ ID NO 231
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 231
acacagatac atgcaccttt tta                                           23

<210> SEQ ID NO 232
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 232
acacagatac acgcaccttt tta                                           23

<210> SEQ ID NO 233
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 233
```

```
ggctggcttt accacagact g                                    21

<210> SEQ ID NO 234
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 234
tggctggctt tgccacagac tgt                                  23

<210> SEQ ID NO 235
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 235
cagtctgtgg taaagccagc c                                    21

<210> SEQ ID NO 236
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 236
acagtctgtg gcaaagccag cca                                  23

<210> SEQ ID NO 237
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 237
tgaaggtggt aagtaagaat tct                                  23

<210> SEQ ID NO 238
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 238
tgaaggtggt aggtaagaat tct                                  23

<210> SEQ ID NO 239
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 239
agaattctta cttaccacct tca                                  23

<210> SEQ ID NO 240
<211> LENGTH: 23
<212> TYPE: DNA
<213> ORGANISM: Artificial sequence
```

<220> FEATURE:
<223> OTHER INFORMATION: Synthetic sequence: Oligonucleotide probe

<400> SEQUENCE: 240
agaattctta cctaccacct tca                                               23

<210> SEQ ID NO 241
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 241
cactcacctc cagtgtgtct gca                                               23

<210> SEQ ID NO 242
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 242
cactcacctc cggtgtgtct gca                                               23

<210> SEQ ID NO 243
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 243
cactcacctc cagtgtgtct gca                                               23

<210> SEQ ID NO 244
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 244
cactcacctc cggtgtgtct gca                                               23

<210> SEQ ID NO 245
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 245
atggctgcgg gaggctggag aag                                               23

<210> SEQ ID NO 246
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 246
atggctgcgg ggggctggag aag                                               23

```
<210> SEQ ID NO 247
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 247
cttctccagc ctcccgcagc cat                                           23

<210> SEQ ID NO 248
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 248
cttctccagc cccccgcagc cat                                           23

<210> SEQ ID NO 249
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 249
gctaattttt gcactttcag tag                                           23

<210> SEQ ID NO 250
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 250
gctaattttt gtactttcag tag                                           23

<210> SEQ ID NO 251
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 251
ctactgaaag tgcaaaaatt agc                                           23

<210> SEQ ID NO 252
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 252
ctactgaaag tacaaaaatt agc                                           23

<210> SEQ ID NO 253
<211> LENGTH: 23
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 253
ttcaggtgtc catacaggaa gtg                                          23

<210> SEQ ID NO 254
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 254
ttcaggtgtc cgtacaggaa gtg                                          23

<210> SEQ ID NO 255
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 255
cacttcctgt atggacacct gaa                                          23

<210> SEQ ID NO 256
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 256
cacttcctgt acggacacct gaa                                          23

<210> SEQ ID NO 257
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 257
gcaagcttat caagaccctc tct                                          23

<210> SEQ ID NO 258
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 258
gcaagcttat cgagaccctc tct                                          23

<210> SEQ ID NO 259
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 259
agagagggtc ttgataagct tgc                                          23

<210> SEQ ID NO 260
```

```
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 260
agagagggtc tcgataagct tgc                                        23

<210> SEQ ID NO 261
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 261
ctgttggcct catcttcctc tgc                                        23

<210> SEQ ID NO 262
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 262
ctgttggcct cgtcttcctc tgc                                        23

<210> SEQ ID NO 263
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 263
gcagaggaag atgaggccaa cag                                        23

<210> SEQ ID NO 264
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 264
gcagaggaag acgaggccaa cag                                        23

<210> SEQ ID NO 265
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 265
atttatgtag aagcaaacaa aat                                        23

<210> SEQ ID NO 266
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 266
```

-continued atttatgtag acgcaaacaa aat                                              23

<210> SEQ ID NO 267
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 267
attttgtttg cttctacata aat                                              23

<210> SEQ ID NO 268
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 268
attttgtttg cgtctacata aat                                              23

<210> SEQ ID NO 269
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 269
gaagatgatg acgaccatgt gga                                              23

<210> SEQ ID NO 270
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 270
gaagatgatg atgaccatgt gga                                              23

<210> SEQ ID NO 271
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 271
tccacatggt cgtcatcatc ttc                                              23

<210> SEQ ID NO 272
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 272
tccacatggt catcatcatc ttc                                              23

<210> SEQ ID NO 273
<211> LENGTH: 23
<212> TYPE: DNA

<213> ORGANISM: Artificial sequence
<220> FEATURE:
<223> OTHER INFORMATION: Synthetic sequence: Oligonucleotide probe

<400> SEQUENCE: 273
aagcggaaag ccaatgatga gag                                              23

<210> SEQ ID NO 274
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 274
aagcggaaag ctaatgatga gag                                              23

<210> SEQ ID NO 275
<211> LENGTH: 19
<212> TYPE: DNA
<213> ORGANISM: Artificial sequence
<220> FEATURE:
<223> OTHER INFORMATION: Synthetic sequence: Oligonucleotide probe

<400> SEQUENCE: 275
ctcatcattg gctttccgc                                                   19

<210> SEQ ID NO 276
<211> LENGTH: 19
<212> TYPE: DNA
<213> ORGANISM: Artificial sequence
<220> FEATURE:
<223> OTHER INFORMATION: Synthetic sequence: Oligonucleotide probe

<400> SEQUENCE: 276
ctcatcatta gctttccgc                                                   19

<210> SEQ ID NO 277
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 277
tggaaataac taatgtgttt gat                                              23

<210> SEQ ID NO 278
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 278
tggaaataac tgatgtgttt gat                                              23

<210> SEQ ID NO 279
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 279
atcaaacaca ttagttattt cca                                              23

```
<210> SEQ ID NO 280
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 280
atcaaacaca tcagttattt cca                                            23

<210> SEQ ID NO 281
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 281
agatgcctat tgtattaccg aga                                            23

<210> SEQ ID NO 282
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 282
agatgcctat tttattaccg aga                                            23

<210> SEQ ID NO 283
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 283
tctcggtaat acaataggca tct                                            23

<210> SEQ ID NO 284
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 284
tctcggtaat aaaataggca tct                                            23

<210> SEQ ID NO 285
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 285
ataaggtgaa acagaaacag atc                                            23

<210> SEQ ID NO 286
<211> LENGTH: 23
<212> TYPE: DNA
<213> ORGANISM: Artificial sequence
<220> FEATURE:
```

-continued

<223> OTHER INFORMATION: Synthetic sequence: Oligonucleotide probe

<400> SEQUENCE: 286
ataaggtgaa atagaaacag atc                                           23

<210> SEQ ID NO 287
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 287
gatctgtttc tgtttcacct tat                                           23

<210> SEQ ID NO 288
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 288
gatctgtttc tatttcacct tat                                           23

<210> SEQ ID NO 289
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 289
tgagcaaaga gattggacac tga                                           23

<210> SEQ ID NO 290
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 290
tgagcaaaga ggttggacac tga                                           23

<210> SEQ ID NO 291
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 291
tcagtgtcca atctctttgc tca                                           23

<210> SEQ ID NO 292
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 292
tcagtgtcca acctctttgc tca                                           23

```
<210> SEQ ID NO 293
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 293
caacagttca tcgtgtttca aat                                              23

<210> SEQ ID NO 294
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 294
caacagttca ttgtgtttca aat                                              23

<210> SEQ ID NO 295
<211> LENGTH: 27
<212> TYPE: DNA
<213> ORGANISM: Artificial sequence
<220> FEATURE:
<223> OTHER INFORMATION: Synthetic sequence: Oligonucleotide probe

<400> SEQUENCE: 295
atatttgaaa ctcgatgaac tgttgct                                          27

<210> SEQ ID NO 296
<211> LENGTH: 27
<212> TYPE: DNA
<213> ORGANISM: Artificial sequence
<220> FEATURE:
<223> OTHER INFORMATION: Synthetic sequence: Oligonucleotide probe

<400> SEQUENCE: 296
atatttgaaa ctcaatgaac tgttgct                                          27

<210> SEQ ID NO 297
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 297
ccaactagtt gctggatact tgcaa                                            25

<210> SEQ ID NO 298
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 298
ccaactagtt gccggatact tgcaa                                            25

<210> SEQ ID NO 299
<211> LENGTH: 25
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 299
ttgcaagtat ccagcaacta gttgg                                            25

<210> SEQ ID NO 300
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 300
ttgcaagtat ccggcaacta gttgg                                            25

<210> SEQ ID NO 301
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 301
tgccaggaaa gccaatgtat gtg                                              23

<210> SEQ ID NO 302
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 302
ttgccaggaa agtcaatgta tgtgg                                            25

<210> SEQ ID NO 303
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 303
ccacatacat tggctttcct ggcaa                                            25

<210> SEQ ID NO 304
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 304
ccacatacat tgactttcct ggcaa                                            25

<210> SEQ ID NO 305
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 305
tagcgctgga catcacagaa gtc                                              23

<210> SEQ ID NO 306
<211> LENGTH: 23
```

```
<212> TYPE: DNA
<213> ORGANISM: Artificial sequence
<220> FEATURE:
<223> OTHER INFORMATION: Synthetic sequence: Oligonucleotide probe

<400> SEQUENCE: 306
tagcgctgga cgtcacagaa gtc                                    23

<210> SEQ ID NO 307
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 307
gacttctgtg atgtccagcg cta                                    23

<210> SEQ ID NO 308
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 308
gacttctgtg acgtccagcg cta                                    23

<210> SEQ ID NO 309
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 309
accagaacgg ccgcctcctc cag                                    23

<210> SEQ ID NO 310
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 310
accagaacgg ctgcctcctc cag                                    23

<210> SEQ ID NO 311
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 311
ctggaggagg cggccgttct ggt                                    23

<210> SEQ ID NO 312
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 312
```
ctggaggagg cagccgttct ggt                                           23

<210> SEQ ID NO 313
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 313
tggatggcct caatcagcgc ggc                                           23

<210> SEQ ID NO 314
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 314
tggatggcct cgatcagcgc ggc                                           23

<210> SEQ ID NO 315
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 315
gccgcgctga ttgaggccat cca                                           23

<210> SEQ ID NO 316
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 316
gccgcgctga tcgaggccat cca                                           23

<210> SEQ ID NO 317
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 317
ggctgctaag acagaggcac cac                                           23

<210> SEQ ID NO 318
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 318
ggctgctaag atagaggcac cac                                           23

<210> SEQ ID NO 319
<211> LENGTH: 23
<212> TYPE: DNA
<213> ORGANISM: Artificial sequence

```
<220> FEATURE:
<223> OTHER INFORMATION: Synthetic sequence: Oligonucleotide probe

<400> SEQUENCE: 319
gtggtgcctc tgtcttagca gcc                                              23

<210> SEQ ID NO 320
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 320
gtggtgcctc tatcttagca gcc                                              23

<210> SEQ ID NO 321
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 321
cttttgaaag ctataaaaac agc                                              23

<210> SEQ ID NO 322
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 322
cttttgaaag ccataaaaac agc                                              23

<210> SEQ ID NO 323
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 323
cttttgaaag ctataaaaac agc                                              23

<210> SEQ ID NO 324
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 324
cttttgaaag ccataaaaac agc                                              23

<210> SEQ ID NO 325
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 325
ccagatgata ccaatgtctg att                                              23
```

```
<210> SEQ ID NO 326
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 326
ccagatgata cgaatgtctg att                                      23

<210> SEQ ID NO 327
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 327
aatcagacat tggtatcatc tgg                                      23

<210> SEQ ID NO 328
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 328
aatcagacat tcgtatcatc tgg                                      23

<210> SEQ ID NO 329
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 329
cctatcttct tcgacacatg gga                                      23

<210> SEQ ID NO 330
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 330
cctatcttct ttgacacatg gga                                      23

<210> SEQ ID NO 331
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 331
tcccatgtgt cgaagaagat agg                                      23

<210> SEQ ID NO 332
<211> LENGTH: 23
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 332
tcccatgtgt caaagaagat agg                                               23

<210> SEQ ID NO 333
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 333
gcagtcatcc tgctctcagt cag                                               23

<210> SEQ ID NO 334
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 334
gcagtcatcc ttctctcagt cag                                               23

<210> SEQ ID NO 335
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 335
ctgactgaga gcaggatgac tgc                                               23

<210> SEQ ID NO 336
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 336
ctgactgaga gaaggatgac tgc                                               23

<210> SEQ ID NO 337
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 337
ttttccatac agtcagtatc aat                                               23

<210> SEQ ID NO 338
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 338
ttttccatac attaaagata gtc                                               23

<210> SEQ ID NO 339
```

```
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 339
attgatactg actgtatgga aaa                                              23

<210> SEQ ID NO 340
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 340
gactatcttt aatgtatgga aaa                                              23

<210> SEQ ID NO 341
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 341
cctaaagtgg gattggtttg ttg                                              23

<210> SEQ ID NO 342
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 342
cctaaagtgg ggttggtttg ttg                                              23

<210> SEQ ID NO 343
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 343
caacaaacca atcccacttt agg                                              23

<210> SEQ ID NO 344
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 344
caacaaacca accccacttt agg                                              23

<210> SEQ ID NO 345
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 345
```
aaagtgctcg gatgtttggga tta                                          23

<210> SEQ ID NO 346
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 346
aaagtgctcg gctgttggga tta                                           23

<210> SEQ ID NO 347
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 347
taatcccaac atccgagcac ttt                                           23

<210> SEQ ID NO 348
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 348
taatcccaac agccgagcac ttt                                           23

<210> SEQ ID NO 349
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 349
tccacacata caggtttgtc act                                           23

<210> SEQ ID NO 350
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 350
tccacacata cgggtttgtc act                                           23

<210> SEQ ID NO 351
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 351
agtgacaaac ctgtatgtgt gga                                           23

<210> SEQ ID NO 352
<211> LENGTH: 23
<212> TYPE: DNA

```
<213> ORGANISM: Artificial sequence
<220> FEATURE:
<223> OTHER INFORMATION: Synthetic sequence: Oligonucleotide probe

<400> SEQUENCE: 352
agtgacaaac ccgtatgtgt gga                                              23

<210> SEQ ID NO 353
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 353
ggcaggaatt cagaatccct cat                                              23

<210> SEQ ID NO 354
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 354
ggcaggaatt cggaatccct cat                                              23

<210> SEQ ID NO 355
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 355
atgagggatt ctgaattcct gcc                                              23

<210> SEQ ID NO 356
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 356
atgagggatt ccgaattcct gcc                                              23

<210> SEQ ID NO 357
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 357
gggcaggaat tcagaatccc tcatc                                            25

<210> SEQ ID NO 358
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 358
gggcaggaat tcggaatccc tcatc                                            25
```

<210> SEQ ID NO 359
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 359
gatgagggat tctgaattcc tgccc                25

<210> SEQ ID NO 360
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 360
gatgagggat tccgaattcc tgccc                25

<210> SEQ ID NO 361
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 361
gcaggaattc agaatccctc a                    21

<210> SEQ ID NO 362
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 362
gcaggaattc ggaatccctc a                    21

<210> SEQ ID NO 363
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 363
tgagggattc tgaattcctg c                    21

<210> SEQ ID NO 364
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 364
tgagggattc cgaattcctg c                    21

<210> SEQ ID NO 365
<211> LENGTH: 23
<212> TYPE: DNA
<213> ORGANISM: Artificial sequence
<220> FEATURE:

```
<223> OTHER INFORMATION: Synthetic sequence: Oligonucleotide probe

<400> SEQUENCE: 365
atggctgcgg gaggctggag aag                                          23

<210> SEQ ID NO 366
<211> LENGTH: 23
<212> TYPE: DNA
<213> ORGANISM: Artificial sequence
<220> FEATURE:
<223> OTHER INFORMATION: Synthetic sequence: Oligonucleotide probe

<400> SEQUENCE: 366
atggctgcgg ggggctggag aag                                          23

<210> SEQ ID NO 367
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 367
ttctccagcc tcccgcagcc a                                            21

<210> SEQ ID NO 368
<211> LENGTH: 21
<212> TYPE: DNA
<213> ORGANISM: Artificial sequence
<220> FEATURE:
<223> OTHER INFORMATION: Synthetic sequence: Oligonucleotide probe

<400> SEQUENCE: 368
ttctccagcc ccccgcagcc a                                            21

<210> SEQ ID NO 369
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 369
cgctacaatt ctcctggtca ggttt                                        25

<210> SEQ ID NO 370
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 370
cgctacaatt cttctggtca ggttt                                        25

<210> SEQ ID NO 371
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 371
aaacctgacc aggagaattg tagcg                                        25
```

```
<210> SEQ ID NO 372
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 372
aaacctgacc agaagaattg tagcg                                              25

<210> SEQ ID NO 373
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 373
gataacttca cacagattga aatgt                                              25

<210> SEQ ID NO 374
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 374
gataacttca catagattga aatgt                                              25

<210> SEQ ID NO 375
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 375
acatttcaat ctgtgtgaag ttatc                                              25

<210> SEQ ID NO 376
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 376
acatttcaat ctatgtgaag ttatc                                              25

<210> SEQ ID NO 377
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 377
acacgtctcg gtcaggggt ctatg                                               25

<210> SEQ ID NO 378
<211> LENGTH: 25
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 378
acacgtctcg gttaggggt ctatg                                          25

<210> SEQ ID NO 379
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 379
catagacccc ctgaccgaga cgtgt                                         25

<210> SEQ ID NO 380
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 380
catagacccc ctaaccgaga cgtgt                                         25

<210> SEQ ID NO 381
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 381
acatgccttg ctctaaggct tagtt                                         25

<210> SEQ ID NO 382
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 382
acatgccttg ctgtaaggct tagtt                                         25

<210> SEQ ID NO 383
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 383
aactaagcct tagagcaagg catgt                                         25

<210> SEQ ID NO 384
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 384
aactaagcct tacagcaagg catgt                                         25

<210> SEQ ID NO 385
<211> LENGTH: 25
```

```
<212> TYPE: DNA
<213> ORGANISM: Artificial sequence
<220> FEATURE:
<223> OTHER INFORMATION: Synthetic sequence: Oligonucleotide probe

<400> SEQUENCE: 385
tctctttact gacagcaact ctggc                                              25

<210> SEQ ID NO 386
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 386
tctctttact gatagcaact ctggc                                              25

<210> SEQ ID NO 387
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 387
gccagagttg ctgtcagtaa agaga                                              25

<210> SEQ ID NO 388
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 388
gccagagttg ctatcagtaa agaga                                              25

<210> SEQ ID NO 389
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 389
cagggaggaa tgaacctgga ttcct                                              25

<210> SEQ ID NO 390
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 390
cagggaggaa tggacctgga ttcct                                              25

<210> SEQ ID NO 391
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 391
```
aggaatccag gttcattcct ccctg                                    25

<210> SEQ ID NO 392
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 392
aggaatccag gtccattcct ccctg                                    25

<210> SEQ ID NO 393
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 393
tgcacacttc agaatgtttg gcacc                                    25

<210> SEQ ID NO 394
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 394
tgcacacttc aggatgtttg gcacc                                    25

<210> SEQ ID NO 395
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 395
ggtgccaaac attctgaagt gtgca                                    25

<210> SEQ ID NO 396
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 396
ggtgccaaac atcctgaagt gtgca                                    25

<210> SEQ ID NO 397
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 397
tggctattgt ttcattgcat tcact                                    25

<210> SEQ ID NO 398
<211> LENGTH: 25
<212> TYPE: DNA
<213> ORGANISM: Artificial sequence

```
<220> FEATURE:
<223> OTHER INFORMATION: Synthetic sequence: Oligonucleotide probe

<400> SEQUENCE: 398
tggctattgt tttattgcat tcact                                         25

<210> SEQ ID NO 399
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 399
agtgaatgca atgaaacaat agcca                                         25

<210> SEQ ID NO 400
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 400
agtgaatgca ataaaacaat agcca                                         25

<210> SEQ ID NO 401
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 401
ggggtagagg ggccggtata aaacc                                         25

<210> SEQ ID NO 402
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 402
ggggtagagg ggtcggtata aaacc                                         25

<210> SEQ ID NO 403
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 403
ggttttatac cggcccctct acccc                                         25

<210> SEQ ID NO 404
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 404
ggttttatac cgacccctct acccc                                         25
```

```
<210> SEQ ID NO 405
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 405
gctgtaccat agcttttctg agaaa                                           25

<210> SEQ ID NO 406
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 406
gctgtaccat agttttctg agaaa                                            25

<210> SEQ ID NO 407
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 407
tttctcagaa aagctatggt acagc                                           25

<210> SEQ ID NO 408
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 408
tttctcagaa aaactatggt acagc                                           25

<210> SEQ ID NO 409
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 409
tgaagtcttc tccttcctcc gccac                                           25

<210> SEQ ID NO 410
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 410
tgaagtcttc tctttcctcc gccac                                           25

<210> SEQ ID NO 411
<211> LENGTH: 25
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 411
gtggcggagg aaggagaaga cttca                                          25

<210> SEQ ID NO 412
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 412
gtggcggagg aaagagaaga cttca                                          25

<210> SEQ ID NO 413
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 413
taagtaagtg gcagagtgaa gattg                                          25

<210> SEQ ID NO 414
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 414
taagtaagtg gcggagtgaa gattg                                          25

<210> SEQ ID NO 415
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 415
caatcttcac tctgccactt actta                                          25

<210> SEQ ID NO 416
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 416
caatcttcac tccgccactt actta                                          25

<210> SEQ ID NO 417
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 417
atctatgtgt gtctgtacat gaata                                          25

<210> SEQ ID NO 418
```

```
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 418
atctatgtgt gtttgtacat gaata                                    25

<210> SEQ ID NO 419
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 419
tattcatgta cagacacaca tagat                                    25

<210> SEQ ID NO 420
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 420
tattcatgta caaacacaca tagat                                    25

<210> SEQ ID NO 421
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 421
gagtagcata tagaatttta ttgct                                    25

<210> SEQ ID NO 422
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 422
gagtagcata tataatttta ttgct                                    25

<210> SEQ ID NO 423
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 423
agcaataaaa ttctatatgc tactc                                    25

<210> SEQ ID NO 424
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 424
```
agcaataaaa ttatatatgc tactc                                           25

<210> SEQ ID NO 425
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 425
tccttgactg ttagacacca aggag                                           25

<210> SEQ ID NO 426
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 426
tccttgactg ttggacacca aggag                                           25

<210> SEQ ID NO 427
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 427
ctccttggtg tctaacagtc aagga                                           25

<210> SEQ ID NO 428
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 428
ctccttggtg tccaacagtc aagga                                           25

<210> SEQ ID NO 429
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 429
atgtacagat caaggacttc ccgta                                           25

<210> SEQ ID NO 430
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 430
atgtacagat cagggacttc ccgta                                           25

<210> SEQ ID NO 431
<211> LENGTH: 25
<212> TYPE: DNA

```
<213> ORGANISM: Artificial sequence
<220> FEATURE:
<223> OTHER INFORMATION: Synthetic sequence: Oligonucleotide probe

<400> SEQUENCE: 431
tacgggaagt ccttgatctg tacat                                              25

<210> SEQ ID NO 432
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 432
tacgggaagt ccctgatctg tacat                                              25

<210> SEQ ID NO 433
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 433
ctgggagaga ctagctcaca cagct                                              25

<210> SEQ ID NO 434
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 434
ctgggagaga ctggctcaca cagct                                              25

<210> SEQ ID NO 435
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 435
agctgtgtga gctagtctct cccag                                              25

<210> SEQ ID NO 436
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 436
agctgtgtga gccagtctct cccag                                              25

<210> SEQ ID NO 437
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 437
cccttccaaa taaccaatca tacac                                              25
```

<210> SEQ ID NO 438
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 438
cccttccaaa tatccaatca tacac                                   25

<210> SEQ ID NO 439
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 439
gtgtatgatt ggttatttgg aaggg                                   25

<210> SEQ ID NO 440
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 440
gtgtatgatt ggatatttgg aaggg                                   25

<210> SEQ ID NO 441
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 441
cactttggaa aaaattctga ctaca                                   25

<210> SEQ ID NO 442
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 442
cactttggaa aatattctga ctaca                                   25

<210> SEQ ID NO 443
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 443
tgtagtcaga atttttcca aagtg                                    25

<210> SEQ ID NO 444
<211> LENGTH: 25
<212> TYPE: DNA
<213> ORGANISM: Artificial sequence
<220> FEATURE:

<223> OTHER INFORMATION: Synthetic sequence: Oligonucleotide probe

<400> SEQUENCE: 444
tgtagtcaga atattttcca aagtg                                              25

<210> SEQ ID NO 445
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 445
cagaggacaa ttatcttgga aagca                                              25

<210> SEQ ID NO 446
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 446
cagaggacaa ttctcttgga aagca                                              25

<210> SEQ ID NO 447
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 447
tgctttccaa gataattgtc ctctg                                              25

<210> SEQ ID NO 448
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 448
tgctttccaa gagaattgtc ctctg                                              25

<210> SEQ ID NO 449
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 449
aattccagaa aacgaatgat tccca                                              25

<210> SEQ ID NO 450
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 450
aattccagaa aatgaatgat tccca                                              25

```
<210> SEQ ID NO 451
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 451
tgggaatcat tcgttttctg gaatt                                        25

<210> SEQ ID NO 452
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 452
tgggaatcat tcattttctg gaatt                                        25

<210> SEQ ID NO 453
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 453
ccacaatgat aacaaagccg acttg                                        25

<210> SEQ ID NO 454
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 454
ccacaatgat aataaagccg acttg                                        25

<210> SEQ ID NO 455
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 455
caagtcggct tgttatcat tgtgg                                         25

<210> SEQ ID NO 456
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 456
caagtcggct ttattatcat tgtgg                                        25

<210> SEQ ID NO 457
<211> LENGTH: 25
<212> TYPE: DNA
<213> ORGANISM: Artificial sequence
<220> FEATURE:
<223> OTHER INFORMATION: Synthetic sequence: Oligonucleotide probe
```

```
<400> SEQUENCE: 457
gggctgagca ccagtttccc cagca                                     25

<210> SEQ ID NO 458
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 458
gggctgagca cctgtttccc cagca                                     25

<210> SEQ ID NO 459
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 459
tgctggggaa actggtgctc agccc                                     25

<210> SEQ ID NO 460
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 460
tgctggggaa acaggtgctc agccc                                     25

<210> SEQ ID NO 461
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 461
atcaatgtca ctagatcaaa atcaa                                     25

<210> SEQ ID NO 462
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 462
atcaatgtca ctggatcaaa atcaa                                     25

<210> SEQ ID NO 463
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 463
ttgattttga tctagtgaca ttgat                                     25

<210> SEQ ID NO 464
<211> LENGTH: 25
```

```
<212> TYPE: DNA
<213> ORGANISM: Artificial sequence
<220> FEATURE:
<223> OTHER INFORMATION: Synthetic sequence: Oligonucleotide probe

<400> SEQUENCE: 464
ttgattttga tccagtgaca ttgat                                          25

<210> SEQ ID NO 465
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 465
agctgagagt aagtgaggac catgt                                          25

<210> SEQ ID NO 466
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 466
agctgagagt aaatgaggac catgt                                          25

<210> SEQ ID NO 467
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 467
acatggtcct cacttactct cagct                                          25

<210> SEQ ID NO 468
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 468
acatggtcct catttactct cagct                                          25

<210> SEQ ID NO 469
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 469
gcatttccct tccgtagacc ctctg                                          25

<210> SEQ ID NO 470
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 470
```

```
gcatttccct tctgtagacc ctctg                                          25

<210> SEQ ID NO 471
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 471
cagagggtct acggaaggga aatgc                                          25

<210> SEQ ID NO 472
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 472
cagagggtct acagaaggga aatgc                                          25

<210> SEQ ID NO 473
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 473
gttctgaaag caaacattta aatat                                          25

<210> SEQ ID NO 474
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 474
gttctgaaag cacacattta aatat                                          25

<210> SEQ ID NO 475
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 475
atatttaaat gtttgctttc agaac                                          25

<210> SEQ ID NO 476
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 476
atatttaaat gtgtgctttc agaac                                          25

<210> SEQ ID NO 477
<211> LENGTH: 25
<212> TYPE: DNA
<213> ORGANISM: Artificial sequence
```

```
<220> FEATURE:
<223> OTHER INFORMATION: Synthetic sequence: Oligonucleotide probe

<400> SEQUENCE: 477
ataaataaat atacagaagc attgg                                         25

<210> SEQ ID NO 478
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 478
ataaataaat atgcagaagc attgg                                         25

<210> SEQ ID NO 479
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 479
ccaatgcttc tgtatattta tttat                                         25

<210> SEQ ID NO 480
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 480
ccaatgcttc tgcatattta tttat                                         25

<210> SEQ ID NO 481
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 481
acatgcctgc ctagaatgat tactt                                         25

<210> SEQ ID NO 482
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 482
acatgcctgc ctggaatgat tactt                                         25

<210> SEQ ID NO 483
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 483
aagtaatcat tctaggcagg catgt                                         25
```

<210> SEQ ID NO 484
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 484
aagtaatcat tccaggcagg catgt                                              25

<210> SEQ ID NO 485
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 485
aagatcagca aacaaaacac caggc                                              25

<210> SEQ ID NO 486
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 486
aagatcagca agaaaacac caggc                                               25

<210> SEQ ID NO 487
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 487
gcctggtgtt ttgtttgctg atctt                                              25

<210> SEQ ID NO 488
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 488
gcctggtgtt ttctttgctg atctt                                              25

<210> SEQ ID NO 489
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 489
tcagtctact tgcgggagag gacag                                              25

<210> SEQ ID NO 490
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 490
tcagtctact tgtgggagag gacag                                              25

<210> SEQ ID NO 491
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 491
ctgtcctctc ccgcaagtag actga                                              25

<210> SEQ ID NO 492
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 492
ctgtcctctc ccacaagtag actga                                              25

<210> SEQ ID NO 493
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 493
cacgcacttc acatgtatct tattc                                              25

<210> SEQ ID NO 494
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 494
cacgcacttc acgtgtatct tattc                                              25

<210> SEQ ID NO 495
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 495
gaataagata catgtgaagt gcgtg                                              25

<210> SEQ ID NO 496
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 496
gaataagata cacgtgaagt gcgtg                                              25

<210> SEQ ID NO 497

-continued

```
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 497
atcagagtta ataaacttcc ctatt                                          25

<210> SEQ ID NO 498
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 498
atcagagtta atgaacttcc ctatt                                          25

<210> SEQ ID NO 499
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 499
aatagggaag tttattaact ctgat                                          25

<210> SEQ ID NO 500
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 500
aatagggaag ttcattaact ctgat                                          25

<210> SEQ ID NO 501
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 501
aatgagaggg gtaacacaca ttatg                                          25

<210> SEQ ID NO 502
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 502
aatgagaggg gtgacacaca ttatg                                          25

<210> SEQ ID NO 503
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 503
```

```
cataatgtgt gttaccccctc tcatt                                            25

<210> SEQ ID NO 504
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 504
cataatgtgt gtcaccccctc tcatt                                            25

<210> SEQ ID NO 505
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 505
tggataactg ctacaattat agttt                                             25

<210> SEQ ID NO 506
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 506
tggataactg cttcaattat agttt                                             25

<210> SEQ ID NO 507
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 507
aaactataat tgtagcagtt atcca                                             25

<210> SEQ ID NO 508
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 508
aaactataat tgaagcagtt atcca                                             25

<210> SEQ ID NO 509
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 509
taaaaacaat tacgtaacac caaga                                             25

<210> SEQ ID NO 510
<211> LENGTH: 25
<212> TYPE: DNA
```

```
<213> ORGANISM: Artificial sequence
<220> FEATURE:
<223> OTHER INFORMATION: Synthetic sequence: Oligonucleotide probe

<400> SEQUENCE: 510
taaaaacaat tatgtaacac caaga                                         25

<210> SEQ ID NO 511
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 511
tcttggtgtt acgtaattgt tttta                                         25

<210> SEQ ID NO 512
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 512
tcttggtgtt acataattgt tttta                                         25

<210> SEQ ID NO 513
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 513
tatttttact ccaaatactg tttca                                         25

<210> SEQ ID NO 514
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 514
tatttttact ccgaatactg tttca                                         25

<210> SEQ ID NO 515
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 515
tgaaacagta tttggagtaa aaata                                         25

<210> SEQ ID NO 516
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 516
tgaaacagta ttcggagtaa aaata                                         25
```

<210> SEQ ID NO 517
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 517
ttacaagttt agctctttt gtaga                                          25

<210> SEQ ID NO 518
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 518
ttacaagttt agttctttt gtaga                                          25

<210> SEQ ID NO 519
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 519
tctacaaaaa gagctaaact tgtaa                                         25

<210> SEQ ID NO 520
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 520
tctacaaaaa gaactaaact tgtaa                                         25

<210> SEQ ID NO 521
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 521
cagttgactg gcagctataa accta                                         25

<210> SEQ ID NO 522
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 522
cagttgactg gcggctataa accta                                         25

<210> SEQ ID NO 523
<211> LENGTH: 25
<212> TYPE: DNA
<213> ORGANISM: Artificial sequence
<220> FEATURE:

```
<223> OTHER INFORMATION: Synthetic sequence: Oligonucleotide probe

<400> SEQUENCE: 523
taggtttata gctgccagtc aactg                                              25

<210> SEQ ID NO 524
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 524
taggtttata gccgccagtc aactg                                              25

<210> SEQ ID NO 525
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 525
ccaaatcttg gttttcagtg c                                                  21

<210> SEQ ID NO 526
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 526
tatgataccg gccaatgctt                                                    20

<210> SEQ ID NO 527
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 527
cacctccttt ggggactgta                                                    20

<210> SEQ ID NO 528
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 528
tcgatagtct tgcaggtgga                                                    20

<210> SEQ ID NO 529
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis
```

<400> SEQUENCE: 529 ttcgcccttta attggctgac					20

<210> SEQ ID NO 530
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 530
tgagtccttc tcagcctggt					20

<210> SEQ ID NO 531
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 531
cctatggcgc aacatctgta					20

<210> SEQ ID NO 532
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 532
ccaatgccta cctagcctgt					20

<210> SEQ ID NO 533
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 533
gcattgcact aagtcttgca c					21

<210> SEQ ID NO 534
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 534
acccccaaag actgactgaa					20

<210> SEQ ID NO 535
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 535
atggaggctg gataggaggt                                                    20

<210> SEQ ID NO 536
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 536
caacctgagc cagaaacctg                                                    20

<210> SEQ ID NO 537
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 537
atgcccagtg ttccactttc                                                    20

<210> SEQ ID NO 538
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 538
gcagatgtcc caggagagag                                                    20

<210> SEQ ID NO 539
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 539
tatagccagg accccacctc                                                    20

<210> SEQ ID NO 540
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 540
tgcttgggat tcctgactct                                                    20

<210> SEQ ID NO 541
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 541

-continued gcacccaatt cctaaagcac                                              20

<210> SEQ ID NO 542
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 542
gcacccaatt cctaaagcac                                              20

<210> SEQ ID NO 543
<211> LENGTH: 25
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 543
ttgctcaact ttagtttttc agtca                                        25

<210> SEQ ID NO 544
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 544
gcagcgggat aagctgataa                                              20

<210> SEQ ID NO 545
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 545
ggtctccagg gacagacgta                                              20

<210> SEQ ID NO 546
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 546
cgctgagcac tgcaaatcta                                              20

<210> SEQ ID NO 547
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 547
ccaaggaggc aaagtagtcg                                              20

<210> SEQ ID NO 548
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 548
tccattgtgg ggattttttgt                                              20

<210> SEQ ID NO 549
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 549
gccttggaag gagaaaggag                                               20

<210> SEQ ID NO 550
<211> LENGTH: 19
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 550
ctggggaggt gctatggat                                                19

<210> SEQ ID NO 551
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 551
aggcttttca ctcctccaaa                                               20

<210> SEQ ID NO 552
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 552
aggcttttca ctcctccaaa                                               20

<210> SEQ ID NO 553
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 553
aggcttttca ctcctccaaa                                               20

<210> SEQ ID NO 554
<211> LENGTH: 21
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 554
tgtgtgtgtg cgtttttgtt t                                              21

<210> SEQ ID NO 555
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 555
tgagacacat agcagcagca                                                20

<210> SEQ ID NO 556
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 556
gcccctccca gttctagttc                                                20

<210> SEQ ID NO 557
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 557
gcaggcagat cacttgaggt                                                20

<210> SEQ ID NO 558
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 558
gctctgccat tgttgcataa                                                20

<210> SEQ ID NO 559
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 559
ccgtctccac tgaaaacaca                                                20

```
<210> SEQ ID NO 560
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 560
gctcagattg gtcctccaga                                                   20

<210> SEQ ID NO 561
<211> LENGTH: 22
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 561
tcttgtcttt gctcccattt tt                                                22

<210> SEQ ID NO 562
<211> LENGTH: 22
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 562
ggcagagaga cagagagact cc                                                22

<210> SEQ ID NO 563
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 563
tgtacaacgc agagcaggtc                                                   20

<210> SEQ ID NO 564
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 564
tgcagaaagc acagaaagga                                                   20

<210> SEQ ID NO 565
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 565
acccacgcag atttattcca                                                   20

<210> SEQ ID NO 566
```

```
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 566
ttggagacaa gacagcatgg                                                   20

<210> SEQ ID NO 567
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 567
ggatcctgaa aggttttgct c                                                 21

<210> SEQ ID NO 568
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 568
gacactgggg tgatgacaga                                                   20

<210> SEQ ID NO 569
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 569
aggttccccc aacagacttt                                                   20

<210> SEQ ID NO 570
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 570
cctcactgcc cttagctctg                                                   20

<210> SEQ ID NO 571
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 571
agctgagtgt tgtgcagtgg                                                   20

<210> SEQ ID NO 572
<211> LENGTH: 21
```

```
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 572
aacccctgca tttcagaatt t                                              21

<210> SEQ ID NO 573
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 573
aaacaactcc acccaggttc                                                20

<210> SEQ ID NO 574
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 574
tggttaagga tgcccagaag                                                20

<210> SEQ ID NO 575
<211> LENGTH: 23
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 575
cttcgataaa tagtgctggg aaa                                            23

<210> SEQ ID NO 576
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 576
cttaatcgga aagctgtgtc g                                              21

<210> SEQ ID NO 577
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 577
ggaaaacacc aacactctcc a                                              21

<210> SEQ ID NO 578
<211> LENGTH: 21
<212> TYPE: DNA
```

```
<213> ORGANISM: Artificial sequence
<220> FEATURE:
<223> OTHER INFORMATION: Synthetic sequence: Forward primer used in SNP
      analysis

<400> SEQUENCE: 578
tcagttgcaa agctacgatg a                                              21

<210> SEQ ID NO 579
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 579
acgcctttgg aacaacaatc                                                20

<210> SEQ ID NO 580
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 580
aacctctttc tcgccctcat                                                20

<210> SEQ ID NO 581
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 581
tgcactcacc catgtactgc                                                20

<210> SEQ ID NO 582
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 582
accagcttgc agtctctgct                                                20

<210> SEQ ID NO 583
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 583
agccaggaga cctgagactg                                                20

<210> SEQ ID NO 584
<211> LENGTH: 20
<212> TYPE: DNA
<213> ORGANISM: Artificial sequence
```

```
<220> FEATURE:
<223> OTHER INFORMATION: Synthetic sequence: Forward primer used in SNP
      analysis

<400> SEQUENCE: 584
tactcagtgc cagaccttcg                                                    20

<210> SEQ ID NO 585
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 585
taaagattgt gggggtgagg                                                    20

<210> SEQ ID NO 586
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 586
aaagggccta attccccagt                                                    20

<210> SEQ ID NO 587
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 587
actacaggca tgtgccaaca                                                    20

<210> SEQ ID NO 588
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 588
tgcccatccc acactttatt                                                    20

<210> SEQ ID NO 589
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 589
tctgtcccca ggaacagtag a                                                  21

<210> SEQ ID NO 590
<211> LENGTH: 20
<212> TYPE: DNA
<213> ORGANISM: Artificial sequence
<220> FEATURE:
```

```
<223> OTHER INFORMATION: Synthetic sequence: Forward primer used in SNP
      analysis

<400> SEQUENCE: 590
atgctgagtg ttggggattc                                                  20

<210> SEQ ID NO 591
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 591
gcttcatgga aactccctgt                                                  20

<210> SEQ ID NO 592
<211> LENGTH: 22
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 592
agacccttcc aagtaagtcc aa                                               22

<210> SEQ ID NO 593
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 593
agagtgctga aacccacagc                                                  20

<210> SEQ ID NO 594
<211> LENGTH: 24
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 594
gaacatgaaa tgcttctttc tcag                                             24

<210> SEQ ID NO 595
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 595
gactggcctt acccattctg                                                  20

<210> SEQ ID NO 596
<211> LENGTH: 21
<212> TYPE: DNA
<213> ORGANISM: Artificial sequence
<220> FEATURE:
<223> OTHER INFORMATION: Synthetic sequence: Forward primer used in SNP
``` analysis

<400> SEQUENCE: 596
cgctttccat agaaaccttg g                                              21

<210> SEQ ID NO 597
<211> LENGTH: 24
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 597
cattgcagga tttacatatc aaca                                           24

<210> SEQ ID NO 598
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 598
cagccaagat gaaacccaag                                                20

<210> SEQ ID NO 599
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 599
acaagttctg ggggacacag                                                20

<210> SEQ ID NO 600
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 600
acaagttctg ggggacacag                                                20

<210> SEQ ID NO 601
<211> LENGTH: 19
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 601
cagagtgata gcggcgagt                                                 19

<210> SEQ ID NO 602
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

```
<400> SEQUENCE: 602
tggtcggtaa tggtctggtt                                              20

<210> SEQ ID NO 603
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 603
aggtcggcta gcttctggat                                              20

<210> SEQ ID NO 604
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 604
ctctgtgtgg tgcctcttca                                              20

<210> SEQ ID NO 605
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 605
cagtttctcc ctcgctgttt                                              20

<210> SEQ ID NO 606
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 606
tgatcaaggt gcccgtctat                                              20

<210> SEQ ID NO 607
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 607
atgctcaggt gtcctccaag                                              20

<210> SEQ ID NO 608
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis
```

```
<400> SEQUENCE: 608
acacagcgga attcagaacc                                                  20

<210> SEQ ID NO 609
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 609
cgtctctccc aggaatcatc                                                  20

<210> SEQ ID NO 610
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 610
catttgggct tggtctcatt                                                  20

<210> SEQ ID NO 611
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 611
aatggggcct cactatgttg                                                  20

<210> SEQ ID NO 612
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 612
tgaattctgg gggcttactg                                                  20

<210> SEQ ID NO 613
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 613
gccagctcag tgaggtcagt a                                                21

<210> SEQ ID NO 614
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 614
```

```
gccagctcag tgaggtcagt a                                              21
```

<210> SEQ ID NO 615
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 615

```
gccagctcag tgaggtcagt a                                              21
```

<210> SEQ ID NO 616
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 616

```
aaagggccta attccccagt                                                20
```

<210> SEQ ID NO 617
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 617

```
tgacctcaca ttggctattg g                                              21
```

<210> SEQ ID NO 618
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 618

```
ataggcataa gccaccatgc                                                20
```

<210> SEQ ID NO 619
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 619

```
agcattcctg ccactcactt                                                20
```

<210> SEQ ID NO 620
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 620

```
agaaaagcag aatgcccaaa                                              20

<210> SEQ ID NO 621
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 621
acctctggga aaagcccta                                               20

<210> SEQ ID NO 622
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 622
taaacaagga agggcactgg                                              20

<210> SEQ ID NO 623
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 623
cagcagtgtc catgagaatc a                                            21

<210> SEQ ID NO 624
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 624
ttgggggcta tttaagttca                                              20

<210> SEQ ID NO 625
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 625
ctcgggcaaa gactcttgtt                                              20

<210> SEQ ID NO 626
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 626
atgatcacac cactgcatcc                                              20
```

<210> SEQ ID NO 627
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 627
cagcgtctcc agcctcttag                                              20

<210> SEQ ID NO 628
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 628
aatcctttga gggagccagt                                              20

<210> SEQ ID NO 629
<211> LENGTH: 23
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 629
tcaggttttc ctcctacttc aaa                                          23

<210> SEQ ID NO 630
<211> LENGTH: 22
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 630
aaactgcgta ggagagaaca gg                                           22

<210> SEQ ID NO 631
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 631
tgggagcaaa gtgaaagtca                                              20

<210> SEQ ID NO 632
<211> LENGTH: 20
<212> TYPE: DNA
<213> ORGANISM: Artificial sequence
<220> FEATURE:
<223> OTHER INFORMATION: Synthetic sequence: Forward primer used in SNP analysis

<400> SEQUENCE: 632
tcacacagcc tttggttctg                                              20

<210> SEQ ID NO 633
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 633
ttcctggtgg tggttttctc                                                  20

<210> SEQ ID NO 634
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 634
catttctgga actgccttgg                                                  20

<210> SEQ ID NO 635
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 635
cctcctccat tccttcacaa                                                  20

<210> SEQ ID NO 636
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 636
tcatatgcct ggcagtttac a                                                21

<210> SEQ ID NO 637
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 637
agggctgcta ccagcataaa                                                  20

<210> SEQ ID NO 638
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 638
ttggagacag cagtcagtgg                                                  20

```
<210> SEQ ID NO 639
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 639
gcggccttca tggataaata                                              20

<210> SEQ ID NO 640
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 640
gaggccacaa gtccaaaatc                                              20

<210> SEQ ID NO 641
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 641
cttagccaca tgcccatttt                                              20

<210> SEQ ID NO 642
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 642
cttctgagat ggaccgcatt                                              20

<210> SEQ ID NO 643
<211> LENGTH: 21
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 643
ttgccactag ttctgaaagc a                                            21

<210> SEQ ID NO 644
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 644
atccctatca ggggcagact                                              20

<210> SEQ ID NO 645
```

```
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 645
gcataatgcc acaggacctt                                              20

<210> SEQ ID NO 646
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 646
gcctcacact cctgagatcc                                              20

<210> SEQ ID NO 647
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 647
acaggaggga aaaggaagga                                              20

<210> SEQ ID NO 648
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 648
caacagctgc cattctgtgt                                              20

<210> SEQ ID NO 649
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 649
tgggggtgct aagacagttt                                              20

<210> SEQ ID NO 650
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 650
ggcaaatcaa atccagcagt                                              20

<210> SEQ ID NO 651
<211> LENGTH: 20
```

<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 651
gcggaagatt ggataactgc                                          20

<210> SEQ ID NO 652
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 652
agtcataagg ccggagtcct                                          20

<210> SEQ ID NO 653
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 653
agcgatttct ggaagcatgt                                          20

<210> SEQ ID NO 654
<211> LENGTH: 19
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 654
cccggaattg aaagcaaat                                           19

<210> SEQ ID NO 655
<211> LENGTH: 20
<212> TYPE: DNA
<213> ORGANISM: Artificial sequence
<220> FEATURE:
<223> OTHER INFORMATION: Synthetic sequence: Forward primer used in SNP
      analysis

<400> SEQUENCE: 655
ggatcaggaa tggacctcaa                                          20

<210> SEQ ID NO 656
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 656
ctgcccagtg cttttcattt                                          20

<210> SEQ ID NO 657
<211> LENGTH: 20
<212> TYPE: DNA

<213> ORGANISM: Artificial sequence
<220> FEATURE:
<223> OTHER INFORMATION: Synthetic sequence: Reverse primer used in SNP analysis

<400> SEQUENCE: 657
gagggcagta gcaatgagga        20

<210> SEQ ID NO 658
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 658
ggagtggcag ttaggacagg        20

<210> SEQ ID NO 659
<211> LENGTH: 18
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 659
accacaccag ccctgttc          18

<210> SEQ ID NO 660
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 660
agtcccttct gctggtgaaa        20

<210> SEQ ID NO 661
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 661
ctctcacgca gctcttcctc        20

<210> SEQ ID NO 662
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 662
agttggggag gtcttgaagg        20

<210> SEQ ID NO 663
<211> LENGTH: 20
<212> TYPE: DNA
<213> ORGANISM: Artificial sequence

```
<220> FEATURE:
<223> OTHER INFORMATION: Synthetic sequence: Reverse primer used in SNP
      analysis

<400> SEQUENCE: 663
aagggccttg tcttttaggc                                                    20

<210> SEQ ID NO 664
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 664
tcctggtgag tttgggattc                                                    20

<210> SEQ ID NO 665
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 665
tcttgctctt gtccaccaca                                                    20

<210> SEQ ID NO 666
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 666
cttccccagg tagagcaaca                                                    20

<210> SEQ ID NO 667
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 667
ccacatttct ctggggacac                                                    20

<210> SEQ ID NO 668
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 668
cttttgtgtg ccaacctgtg                                                    20

<210> SEQ ID NO 669
<211> LENGTH: 25
<212> TYPE: DNA
<213> ORGANISM: Artificial sequence
<220> FEATURE:
```

```
<223> OTHER INFORMATION: Synthetic sequence: Reverse primer used in SNP
      analysis

<400> SEQUENCE: 669
aactgaagac actactagag cagca                                           25

<210> SEQ ID NO 670
<211> LENGTH: 18
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 670
aggcaggcac acacatgg                                                   18

<210> SEQ ID NO 671
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 671
gacttgtgat ccgggatttg                                                 20

<210> SEQ ID NO 672
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 672
ggtcaacatg tcagcaccag                                                 20

<210> SEQ ID NO 673
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 673
ggtcaacatg tcagcaccag                                                 20

<210> SEQ ID NO 674
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 674
agtggcagac catccacatc                                                 20

<210> SEQ ID NO 675
<211> LENGTH: 21
<212> TYPE: DNA
<213> ORGANISM: Artificial sequence
<220> FEATURE:
<223> OTHER INFORMATION: Synthetic sequence: Reverse primer used in SNP
```

-continued analysis

<400> SEQUENCE: 675
ctttgacaag gaggtttgtc g                                              21

<210> SEQ ID NO 676
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 676
aggaatcgtt ctggggagag                                                20

<210> SEQ ID NO 677
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 677
gctctgtcct ttctccacca                                                20

<210> SEQ ID NO 678
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 678
agaaagtccc tgtgggtgtg                                                20

<210> SEQ ID NO 679
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 679
ctggcttctc tgggaggaat                                                20

<210> SEQ ID NO 680
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 680
gcttggctct caggagacag                                                20

<210> SEQ ID NO 681
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 681
gcttcaaagt gctcaaatgg t    21

<210> SEQ ID NO 682
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 682
aaggacgcac tgtggttagg    20

<210> SEQ ID NO 683
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 683
aaggacgcac tgtggttagg    20

<210> SEQ ID NO 684
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 684
aaggacgcac tgtggttagg    20

<210> SEQ ID NO 685
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 685
ccaagccctc ccagaattta    20

<210> SEQ ID NO 686
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 686
caggaaacag ctcagacgtg    20

<210> SEQ ID NO 687
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 687
aaagttgggg acacacaagc                                              20

<210> SEQ ID NO 688
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 688
gcccaggctg gagtacaata                                              20

<210> SEQ ID NO 689
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 689
cacaccacag taggcattca a                                            21

<210> SEQ ID NO 690
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 690
gcccaggctg gagtacaata                                              20

<210> SEQ ID NO 691
<211> LENGTH: 22
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 691
ttcgcctaat ttttctctca ca                                           22

<210> SEQ ID NO 692
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 692
gacttcctgc cagtgctctc                                              20

<210> SEQ ID NO 693
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 693
aaacagcgag ggagaaactg                                               20

<210> SEQ ID NO 694
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 694
tgtttcccac gggtttgata                                               20

<210> SEQ ID NO 695
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 695
ctgggctatg gagcaagact                                               20

<210> SEQ ID NO 696
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 696
accacgaaga gactggctgt                                               20

<210> SEQ ID NO 697
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 697
gcttgggagg ctcctttatt                                               20

<210> SEQ ID NO 698
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 698
cctcctccat cttcatgctc                                               20

<210> SEQ ID NO 699
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 699

```
gccaacaaaa catggaaggt                                              20

<210> SEQ ID NO 700
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 700
caagctaagc caacatgcaa                                              20

<210> SEQ ID NO 701
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 701
caggaatgtt gagcccagtt                                              20

<210> SEQ ID NO 702
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 702
gcatagcctc ggagacagac                                              20

<210> SEQ ID NO 703
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 703
tcccgggtat atgatctcca                                              20

<210> SEQ ID NO 704
<211> LENGTH: 25
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 704
tcacctaagg acagtctaaa attgc                                        25

<210> SEQ ID NO 705
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 705
agccgtgggt ttagctgtta                                              20
```

<210> SEQ ID NO 706
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 706
gcttggaagt tgccattcat                                              20

<210> SEQ ID NO 707
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 707
agcttgccac aggacagttt                                              20

<210> SEQ ID NO 708
<211> LENGTH: 22
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 708
ttgagttgtt gcagcagaga tt                                           22

<210> SEQ ID NO 709
<211> LENGTH: 21
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 709 tgcctttga tgactgggtt a                                             21

<210> SEQ ID NO 710
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 710
agcagggaag cacttgaaga                                              20

<210> SEQ ID NO 711
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 711
ggtcacacag gaaccagacc                                              20

<210> SEQ ID NO 712
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 712
tgcaggtgat cacgtcaatg                                              20

<210> SEQ ID NO 713
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 713 cccccaaaccc tgactttcat                                             20

<210> SEQ ID NO 714
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 714
tactgattga gcccccttgt                                              20

<210> SEQ ID NO 715
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 715
ttaaagtggc aggagcaggt                                              20

<210> SEQ ID NO 716
<211> LENGTH: 21
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 716
cccattcatc catctccctt a                                            21

<210> SEQ ID NO 717
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 717
cctcaccccc acaatcttta                                              20

<210> SEQ ID NO 718
<211> LENGTH: 22
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 718
cgagatcaag agatcaagac ca                                              22

<210> SEQ ID NO 719
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 719
tggatagcaa ctgctccaag                                                 20

<210> SEQ ID NO 720
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 720
gctggaagac acttggagga                                                 20

<210> SEQ ID NO 721
<211> LENGTH: 20
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 721
tccaagaagc cagctcattt                                                 20

<210> SEQ ID NO 722
<211> LENGTH: 24
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 722
cacaccacaa aaagataatc acaa                                            24

<210> SEQ ID NO 723
<211> LENGTH: 22
<212> TYPE: DNA
<213> ORGANISM: Artificial sequence
<220> FEATURE:
<223> OTHER INFORMATION: Synthetic sequence: Reverse primer used in SNP analysis

<400> SEQUENCE: 723
catcagactg gtgagaatca tc                                              22

<210> SEQ ID NO 724

```
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 724
attcacggct gactttggaa                                               20

<210> SEQ ID NO 725
<211> LENGTH: 24
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 725
tgaacataga cataaccctg aagc                                          24

<210> SEQ ID NO 726
<211> LENGTH: 23
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 726
tccactcaaa gacacatctt caa                                           23

<210> SEQ ID NO 727
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 727
tgtgtcaggc aatgaggcta                                               20

<210> SEQ ID NO 728
<211> LENGTH: 26
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 728
ggcatctgag actatgtcta acagaa                                        26

<210> SEQ ID NO 729
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 729
gggttgggga gaaagatatg a                                             21

<210> SEQ ID NO 730
<211> LENGTH: 20
```

```
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 730
attgcaccta gggtttgtgc                                                      20

<210> SEQ ID NO 731
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 731
attgcaccta gggtttgtgc                                                      20

<210> SEQ ID NO 732
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 732
cccttcaatg gctggtacat                                                      20

<210> SEQ ID NO 733
<211> LENGTH: 19
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 733
tggcctatga tgccatctg                                                       19

<210> SEQ ID NO 734
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 734
ctgagagctc ctgtgccttc                                                      20

<210> SEQ ID NO 735
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 735
cagcttcctg gactcctgtc                                                      20

<210> SEQ ID NO 736
<211> LENGTH: 20
<212> TYPE: DNA
```

```
<213> ORGANISM: Artificial sequence
<220> FEATURE:
<223> OTHER INFORMATION: Synthetic sequence: Reverse primer used in SNP
      analysis

<400> SEQUENCE: 736
tttgctactc cttgcccttc                                                     20

<210> SEQ ID NO 737
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 737
tgtaaggcac atggaggtga                                                     20

<210> SEQ ID NO 738
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 738
gtgatcgtac aggtgcatcg                                                     20

<210> SEQ ID NO 739
<211> LENGTH: 25
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 739
gcttgttact tagacaaatg gcact                                               25

<210> SEQ ID NO 740
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 740
tgtagggagc ccagaagaga                                                     20

<210> SEQ ID NO 741
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 741
tccatacctt ggggtttcag                                                     20

<210> SEQ ID NO 742
<211> LENGTH: 20
<212> TYPE: DNA
<213> ORGANISM: Artificial sequence
```

```
<220> FEATURE:
<223> OTHER INFORMATION: Synthetic sequence: Reverse primer used in SNP
      analysis

<400> SEQUENCE: 742
tgcagggttt tgatacatgg                                               20

<210> SEQ ID NO 743
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 743
atttctcctc caccctctgc                                               20

<210> SEQ ID NO 744
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 744
gaacggtcct ctcacttctc a                                             21

<210> SEQ ID NO 745
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 745
gaacggtcct ctcacttctc a                                             21

<210> SEQ ID NO 746
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 746
gaacggtcct ctcacttctc a                                             21

<210> SEQ ID NO 747
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 747
cctcaccccc acaatcttta                                               20

<210> SEQ ID NO 748
<211> LENGTH: 21
<212> TYPE: DNA
<213> ORGANISM: Artificial sequence
<220> FEATURE:
```

```
<223> OTHER INFORMATION: Synthetic sequence: Reverse primer used in SNP
      analysis

<400> SEQUENCE: 748
cacattggaa tttgggaaga a                                            21

<210> SEQ ID NO 749
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 749
aggtgagggg ctgaagaagt                                              20

<210> SEQ ID NO 750
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 750
gtccttctcc gactgtgagc                                              20

<210> SEQ ID NO 751
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 751
catgacggtg acctgttgac                                              20

<210> SEQ ID NO 752
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 752
ccccacttcc accaaaatta                                              20

<210> SEQ ID NO 753
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 753
ggattggctg aacattttgg                                              20

<210> SEQ ID NO 754
<211> LENGTH: 20
<212> TYPE: DNA
<213> ORGANISM: Artificial sequence
<220> FEATURE:
<223> OTHER INFORMATION: Synthetic sequence: Reverse primer used in SNP
``` analysis

<400> SEQUENCE: 754
aatgggtggg ggtgttattt                                             20

<210> SEQ ID NO 755
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 755
gactgagtgc aatgccaaaa                                             20

<210> SEQ ID NO 756
<211> LENGTH: 19
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 756 cgcttttcc accaggttt                                               19

<210> SEQ ID NO 757
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 757
ctgggctctg cttgtttctc                                             20

<210> SEQ ID NO 758
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 758
agctgttcct cccgtacctt                                             20

<210> SEQ ID NO 759
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 759
agactagtgc cgagggttca                                             20

<210> SEQ ID NO 760
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 760
tcgtgcaaaa tcaaggttca                                            20

<210> SEQ ID NO 761
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 761
caagcttgca tggacacact                                            20

<210> SEQ ID NO 762
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 762
atcttggcat ctccttggtg                                            20

<210> SEQ ID NO 763
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 763
tgagaagggc tttggcttta                                            20

<210> SEQ ID NO 764
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 764
ccctaagaaa ggtgccatga                                            20

<210> SEQ ID NO 765
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 765
aaatggtgct gggaaaactg                                            20

<210> SEQ ID NO 766
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

```
<400> SEQUENCE: 766 gaatagggggg aaagggggttt                                              20

<210> SEQ ID NO 767
<211> LENGTH: 21
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 767
cttgaaggat gctttccaag a                                              21

<210> SEQ ID NO 768
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 768
agtttggttt ccccacactg                                                20

<210> SEQ ID NO 769
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 769
tttgccctaa atgccaagtc                                                20

<210> SEQ ID NO 770
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 770
agggaaggaa accaggagaa                                                20

<210> SEQ ID NO 771
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 771
ggagaaaggc agagggagat                                                20

<210> SEQ ID NO 772
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 772
```
tctccggtgg tagatcttgg					20

<210> SEQ ID NO 773
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 773
tcctgacctc acatgatcca					20

<210> SEQ ID NO 774
<211> LENGTH: 22
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 774
ttcacttcga ccaggatatt ca				22

<210> SEQ ID NO 775
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 775
tcgggcattc acaatgttta					20

<210> SEQ ID NO 776
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 776
aatcagtgct gctgcttgtg					20

<210> SEQ ID NO 777
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 777
tcaggacccg atttgtcagt					20

<210> SEQ ID NO 778
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 778 acaggaccttt tgccatcatc                      20

<210> SEQ ID NO 779
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 779
gatcctgagg gtggaactga                      20

<210> SEQ ID NO 780
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 780
catgaggctg ggagttagga                      20

<210> SEQ ID NO 781
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 781
ggcaggcaat acacacacac                      20

<210> SEQ ID NO 782
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 782
catcccatgg atttgtagcc                      20

<210> SEQ ID NO 783
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 783
gcaaggcatc tatcctggag                      20

<210> SEQ ID NO 784
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 784
gatgggtccc cattttttctt                      20

```
<210> SEQ ID NO 785
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 785
gctctacccc atgagaatgc                                              20

<210> SEQ ID NO 786
<211> LENGTH: 20
<212> TYPE: DNA
<213> ORGANISM: Artificial sequence
<220> FEATURE:
<223> OTHER INFORMATION: Synthetic sequence: Reverse primer used in SNP
      analysis

<400> SEQUENCE: 786
ggagaactcg ccctctttct                                              20
```